United States Patent
Nishimura et al.

(10) Patent No.: US 11,219,697 B2
(45) Date of Patent: Jan. 11, 2022

(54) OSTEOADSORPTIVE FLUOROGENIC SUBSTRATE OF CATHEPSIN K FOR IMAGING OSTEOCLAST ACTIVITY AND MIGRATION

(71) Applicants: The Regents of the University of California, Oakland, CA (US); UNIVERSITY OF SOUTHERN CALIFORNIA, Los Angeles, CA (US)

(72) Inventors: Ichiro Nishimura, Venice, CA (US); Akishige Hokugo, Los Angeles, CA (US); Kenzo Morinaga, Los Angeles, CA (US); Charles E. McKenna, Pacific Palisades, CA (US); Boris A Kashemirov, Los Angeles, CA (US); Eric T. Richard, Los Angeles, CA (US)

(73) Assignees: The Regents of the University of California, Oakland, CA (US); University of Southern California, Los Angeles, CA (US)

( * ) Notice: Subject to any disclaimer, the term of this patent is extended or adjusted under 35 U.S.C. 154(b) by 162 days.

(21) Appl. No.: 16/623,740

(22) PCT Filed: Jul. 13, 2018

(86) PCT No.: PCT/US2018/042132
§ 371 (c)(1),
(2) Date: Dec. 17, 2019

(87) PCT Pub. No.: WO2019/018238
PCT Pub. Date: Jan. 24, 2019

(65) Prior Publication Data
US 2020/0215205 A1 Jul. 9, 2020

Related U.S. Application Data

(60) Provisional application No. 62/533,025, filed on Jul. 15, 2017.

(51) Int. Cl.
| | |
|---|---|
| *A61K 49/00* | (2006.01) |
| *A61K 47/54* | (2017.01) |
| *A61K 47/64* | (2017.01) |
| *A61K 9/00* | (2006.01) |
| *A61K 38/23* | (2006.01) |
| *A61K 38/29* | (2006.01) |

(52) U.S. Cl.
CPC .......... *A61K 49/0056* (2013.01); *A61K 9/007* (2013.01); *A61K 9/0014* (2013.01); *A61K 9/0031* (2013.01); *A61K 9/0053* (2013.01); *A61K 38/23* (2013.01); *A61K 38/29* (2013.01); *A61K 47/548* (2017.08); *A61K 47/64* (2017.08); *A61K 49/0021* (2013.01)

(58) Field of Classification Search
CPC .. A61K 49/0056; A61K 47/548; A61K 47/64; A61K 9/0014; A61K 9/0031; A61K 9/0053; A61K 9/007; A61K 38/23; A61K 38/29; A61K 49/0021; A61K 49/0041; A61K 49/0043; A61K 49/0052; C12Q 1/37; A61P 19/10; C07F 9/65583
See application file for complete search history.

(56) References Cited

U.S. PATENT DOCUMENTS

| | | |
|---|---|---|
| 6,541,454 B1 | 4/2003 | Breuer et al. |
| 8,603,977 B2 | 12/2013 | Gardell et al. |
| 8,815,214 B2 | 8/2014 | Rahopadhye et al. |
| 9,492,508 B2 | 11/2016 | Gardell et al. |
| 2014/0073780 A1 | 3/2014 | Bhushan et al. |

FOREIGN PATENT DOCUMENTS

| | | |
|---|---|---|
| WO | WO 1998/005683 A1 | 2/1998 |
| WO | WO 2011/143406 A2 | 11/2011 |
| WO | WO 2011/143406 A3 | 11/2011 |

OTHER PUBLICATIONS

PCT International Search Report and Written Opinion dated Dec. 3, 2018 issued in PCT/US2018/042132.
PCT International Preliminary Report on Patentability dated Jan. 21, 2020 issued in PCT/US2018/042132.
European Extended Search Report dated Feb. 17, 2021 issued in EP 18835562.2.
Bhushan et al. (2008) "Detection of Breast Cancer Microcalcifications Using a Dual-modality SPECT/NIR Fluorescent Probe" *J. Am. Chem. Soc.* 130(52): 17648-17649.
Dang et al. (2016) "Targeted Delivery Systems for Molecular Therapy in Skeletal Disorders" *Int. J. Mol. Sci.* 17: 428 [15 pages] doi:10.3390/ijms17030428.

(Continued)

*Primary Examiner* — Robert S Cabral
(74) *Attorney, Agent, or Firm* — Tom Hunter; Weaver Austin Villeneuve & Sampson LLP

(57) ABSTRACT

In certain embodiments osteoadsorptive fluorogenic substrates of cathepsin K (or other proteases) are provided. Utilizing a bisphosphonate targeting moiety, the fluorogenic substrates provide effective bone-targeted protease sensor(s). In certain embodiments the "probes" comprise cleavable fluorophore-quencher pair linked by a cathepsin K (or other protease) peptide substrate and tethered to a bisphosphonate. Unlike existing probes that are cleared within a few days in vivo, the probes described herein (e.g., OFS-1) allow for monitoring resorption over the course of longer time periods with a single dose.

21 Claims, 7 Drawing Sheets
Specification includes a Sequence Listing.

(56) References Cited

OTHER PUBLICATIONS

Hirabayashi and Fujisaki (2003) "Bone-Specific Drug Delivery Systems" *Clin Pharmacokinet* 42(15): 1319-1330.
Katsumi et al. (2015) "Molecular Design of Bisphosphonate-Modified Proteins for Efficient Bone Targeting In Vivo" *PLOS One* [15 pages] DOI:10.1371/journal.pone.0135966.
Rudnick-Glick et al. (2016) "Targeted drug delivery of near IR fluorescent doxorubicin-conjugated poly(ethylene glycol) bisphosphonate nanoparticles for diagnosis and therapy of primary and metastatic bone cancer in a mouse model" *J Nanobiotechnol* 14: 80 [11 pages].
Sun et al. (2016) "Fluorescent Bisphosphonate and Carboxyphosphate Probes: A Versatile Imaging Toolkit for Applicationsin Bone Biology and Biomedicine" *Bioconjugate Chem.* 27(2): 329-340 [Abstract only—2 pages] Retrieved from the Internet on Nov. 20, 2018; URL: https://pubs.acs.org/doi/abs/10.1021/acs.bioconjchem.5b00369.
Tseng et al. (2015) "Bisphosphonate-induced differential modulation of immune cell function in gingiva and bone marrow in vivo: Role in osteoclastmediated NK cell activation" *Oncotarget* (www.impactjournals.com/oncotarget/) 6(24): 20002-20025.

OFS-1 activation by Multiple myeloma

A: IVIS - 8228-LUC luciferase activity
B: IVIS – OFS-1 fluorescent signal
C: Micro CT Strong fluorescence was detected at the 8226-LUC grafted sites, even in an early osteoporosis stage

OSTEOADSORPTIVE FLUOROGENIC SUBSTRATE OF CATHEPSIN K FOR IMAGING OSTEOCLAST ACTIVITY AND MIGRATION

CROSS-REFERENCE TO RELATED APPLICATIONS

This application is a US 371 National Phase of PCT/US2018/042132, filed Jul. 13, 2018, which claims benefit of and priority to U.S. Ser. No. 62/533,025, filed Jul. 15, 2017, both of which are incorporated herein by reference in their entirety for all purposes.

STATEMENT OF GOVERNMENTAL SUPPORT

This invention was made with Government support under Grant Numbers DE021982, DE022552, and DE023410, awarded by the National Institutes of Health. The Government has certain rights in the invention.

INCORPORATION BY REFERENCE OF SEQUENCE LISTING PROVIDED AS A TEXT FILE

This application contains references to nucleic acid sequences which have been submitted concurrently herewith as the sequence listing text file "UCLA-P190US_ST25.txt", file size 7.56 kb, created on May 30, 2020, which is incorporated by reference in its entirety pursuant to 37 C.F.R. 1.52(e)(5).

BACKGROUND

Cathepsin K is a cysteine protease produced by osteoclasts and is important for type I collagen degradation in bone resorption (see, e.g., Bromme et al. (1996) *J. Biol. Chem.* 271: 2126-2132; Novinec & Lenarčič (2013) *Biol. Chem.* 394: 1163-1179. It plays a role in the disease process in osteoporosis (see, e.g., Novinec & Lenarčič (2013) *Biol. Chem.* 394: 1163-1179; Le et al. (2015) *Calcif. Tissue Int.* 98: 381-397), osteoarthritis (see, e.g., Novinec & Lenarčič (2013) *Biol. Chem.* 394: 1163-1179; Connor et al. (1009) *Osteoarthrit. & Cartil.* 17: 1236-1243), and rheumatoid arthritis (see, e.g. Novinec & Lenarčič (2013) *Biol. Chem.* 394: 1163-1179). It is also expressed in other cell types and tissues (see, e.g., Bühling et al. (1999) *Am. J Respir. Cell Mol. Biol.* 20: 612-619) and has been found to be expressed in a number of cancers (see, e.g., Littlewood-Evans et al. (1997) *Cancer Res.* 57: 5386-5390). There is some evidence that it plays a role in a number of other diseases including atherosclerosis (see, e.g., Cheng et al. (2011) *Hypertension*, 58: 978-986; Sukhova et al. (1998) *J Clin. Invest.* 102:576-583) and emphysema (see, e.g., Golovatch et al. (2009) *Exp. Lung Res.* 35: 631-645). Detection of cathepsin k activity both in vitro and in vivo can be a powerful strategy for studying the role of cathepsin k in various disease processes and assessing the effectiveness of drugs that affect cathepsin k or the cells that express it.

Several fluorescent probes specifically activated by cathepsin k have been developed and tested in vivo (see, e.g., Jaffer et al. (2007) *Circulation*, 115: 2292-2298; Kozloff et al. (2009) *Bone*, 44: 190-198; Rajopadhye et al. (2014) U.S. Pat. No. 8,815,214 B2). These probes employ the internally quenched fluorescence (IQF) strategy where two self-quenching fluorophores or a fluorophore and a quencher are connected by a linker. In the intact state these molecules have weak fluorescence as the fluorophore is quenched by contact with another fluorophore or via Forster resonance energy transfer (see, e.g. Forster et al. (1948) *Annalen der Physik* 437: 55-75; Jares-Erijman & Jovin (2003) *Nat. Biotechnol.* 21: 1387-1395) to a non-emissive chromophore. Upon cleavage of the linker, the pair of chromophores is separated and the quenching process can no longer occur efficiently. The fluorophore then can emit stronger fluorescence.

These probes can be useful for imaging cathepsin k activity in vivo soon after injection and one example has a half-life in tissue of 36 hours (see, e.g., Rajopadhye et al. (2014) U.S. Pat. No. 8,815,214 B2; Cat K 680 FAST In vivo Imaging Protocol. 1-3 (2017) Available at: http://www.perkinelmer.com/product/cat-k-680-fast-nev11000). However, imaging must be performed within 24 h of injection. Clearance of the probe would be expected to have a significant effect on fluorescent signal strength.

SUMMARY

In certain embodiments osteoadsorptive fluorogenic substrates of cathepsin K (or other proteases) are provided. Utilizing a bisphosphonate targeting moiety, the fluorogenic substrates provide effective bone-targeted protease sensor(s). In certain embodiments the "probes" comprise cleavable fluorophore-quencher pair linked by a cathepsin K (or other protease) peptide substrate and tethered to a bisphosphonate. Unlike existing probes that are cleared within a few days in vivo, the probes described herein (e.g., OFS-1) allow for monitoring resorption over the course of longer time periods with a single dose.

Various embodiments contemplated herein may include, but need not be limited to, one or more of the following:

Embodiment 1: An osteoasorptive fluorogenic probe, said probe comprising a compound according to Formula I:

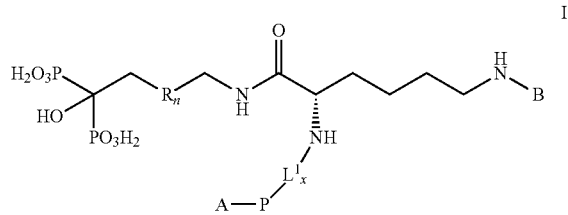

wherein:

R is $CH_2$;

n is 0 to 6;

$L^1$ is a linker comprising 1 to 6 carbons;

x is 0 or 1;

P is a peptide comprising a cleavage site for a protease; and

A is a quencher and B is a fluorophore, or B is a quencher and A is a fluorophore.

Embodiment 2: The probe of embodiment 1, wherein said probe comprises a compound according to Formula II:

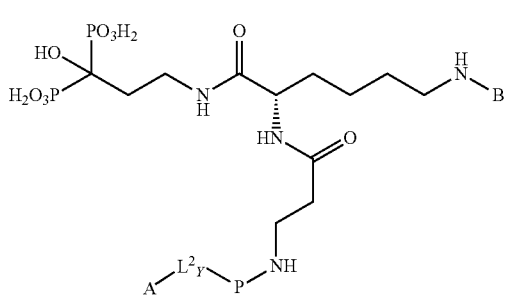

wherein: $L^2$ is selected from the group consisting of a C1-C12 carbon linker, an amino acid, and a peptide; and y is 0 or 1.

Embodiment 3: The probe of embodiment 1, wherein said probe comprises a compound according to Formula III:

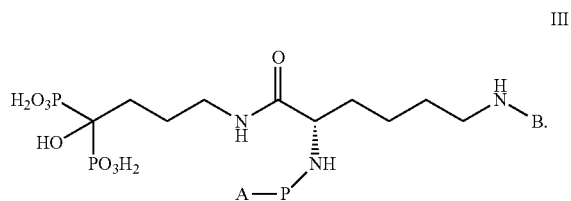

Embodiment 4: The probe according to any one of embodiments 1-3, wherein A is a quencher and B is a fluorophore.

Embodiment 5: The probe according to any one of embodiments 1-4, wherein P ranges in length from about 2 amino acids, or from about 4, or from about 6 amino acids, or from about 8 amino acids up to about 25 amino acids, or up to about 20 amino acids, or up to about 15 amino acids, or up to about 10 amino acids.

Embodiment 6: The probe of embodiment 5, wherein P ranges in length from about 6 amino acid up to about 10 amino acids.

Embodiment 7: The probe according to any one of embodiments 1-6, wherein P comprises a cleavage site for a protease selected from the group consisting of cathepsin K, cathepsin B, cathepsin C, cathepsin D, cathepsin E, cathepsin G, cathepsin L, tartrate-resistant acid protease (TRAP), matrix metalloproteinases (MMP)-2, MMP-8, MMP-9, MMP-10, MMP-12, MMP-13, MMP-14, Kallikreins (hK), hK1, PSA (hK3), hK10, hK15, seriene proteases uPA and uPAR, plasmin, ceruloplasmin (CP), thrombin, trypsin, fibroblast activation protein (FAP), and caspases.

Embodiment 8: The probe of embodiment 7, wherein P comprises an amino acid sequence that is cleaved by cathepsin K.

Embodiment 9: The probe of embodiment 7, wherein P consists of an amino acid sequence that is cleaved by cathepsin K.

Embodiment 10: The probe according to any one of embodiments 1-8, wherein P comprises the amino acid sequence Gly-His-Pro-Gly-Gly-Pro-Gln-Gly (SEQ ID NO:1).

Embodiment 11: The probe according to any one of embodiments 1-8, wherein the amino acid sequence of P consists of the sequence Gly-His-Pro-Gly-Gly-Pro-Gln-Gly (SEQ ID NO: 1).

Embodiment 12: The probe according to any one of embodiments 1-11, wherein said fluorophore is a fluorophore that emits in the visible spectrum.

Embodiment 13: The probe according to any one of embodiments 1-11, wherein said fluorophore is a fluorophore that emits in the near infrared.

Embodiment 14: The probe according to any one of embodiments 1-11, wherein said fluorophore is selected from the group consisting of FAM, BODIPY FL, Oregon Green 488, Rhodamine Green, Oregon Green 514, TET, Cal Gold, BODIPY R6G, Yakima Yellow, JOE, HEX, Cal Orange, BODIPY TMR-X, Quasar-570/Cy3, TAMRA, Rhodamine Red-X, Redmond Red, BODIPY 581/591, Cy3.5, ROX, Cal Red/Texas Red, BODIPY TR-X, BODIPY 630/665-X, Pulsar-650, Quasar-670/Cy5, Cy5.5, ALEXAFLUOR® AF647, ALEXAFLUOR® AF660, ALEXAFLUOR® AF680, ALEXAFLUOR® AF700, ALEXAFLUOR® AF750, ALEXAFLUOR® AF790.

Embodiment 15: The probe of embodiment 14, wherein said fluorophore comprises 5-FAM.

Embodiment 16: The probe of embodiment 14, wherein said fluorophore comprises ALEXAFLUOR® AF647.

Embodiment 17: The probe according to any one of embodiments 1-14, wherein said quencher is selected from the group consisting of BHQ-1, BHQ-3, Dabcyl, QSY 35, BHQ-0, Eclipse, QSY 7, QSY 9, BHQ-2, ElleQuencher, Iowa Black, QSY 21, TAMRA, and Blackberry Quencher BBQ-650.

Embodiment 18: The probe of embodiment 17, wherein said quencher comprises BHQ-1.

Embodiment 19: The probe of embodiment 17, wherein said quencher comprises BHQ-3.

Embodiment 20: The probe according to any one of embodiments 1-19, wherein said probe comprises a fluorophore/quencher pair shown (by an X) in Table 4.

Embodiment 21: The probe of embodiment 20, wherein said fluorophore comprises 5-FAM and said quencher comprises BHQ-1.

Embodiment 22: The probe of embodiment 20, wherein said fluorophore comprises ALEXAFLUOR® AF647 and said quencher comprises BHQ-3.

Embodiment 23: The probe of embodiment 20, wherein said fluorophore comprises 5-FAM and said quencher comprises BHQ-1.

Embodiment 24: The probe of embodiment 1, wherein said probe comprises OFS-1.

Embodiment 25: The probe of embodiment 1, wherein said probe comprises the structure of OFS-1.

Embodiment 26: The probe of embodiment 1, wherein said probe comprises the structure:

Embodiment 27: The probe according to any one of embodiments 1-26, wherein said probe accumulates on a calcium phosphate surface when administered to a mammal in vivo.

Embodiment 28: The probe according to any one of embodiments 1-27, wherein said probe said probe provides a detectable signal in vivo when said peptide is cleaved by a protease.

Embodiment 29: The probe according to any one of embodiments 1-28, wherein said probe, when administered to a mammal in vivo, is taken up by bone.

Embodiment 30: The probe according to any one of embodiments 1-29, wherein said probe has an in vivo tissue half-life of greater than 1.5 days, or greater than 2 days, or greater than 3 days, or greater than 4 days, or greater than 5 days, or greater than 6 days, or greater than 1 week, or greater than 2 weeks, or greater than 3 weeks, or greater than 1 month.

Embodiment 31: A pharmaceutical formulation said formulation comprising: a probe according to any one of embodiments 1-30; and a pharmaceutically acceptable carrier.

Embodiment 32: The formulation of embodiment 31, wherein said formulation is for administration via a modality selected from the group consisting of intraperitoneal administration, topical administration, oral administration, inhalation administration, transdermal administration, subdermal depot administration, and rectal administration.

Embodiment 33: The formulation according to any one of embodiments 31-32, wherein said formulation is a unit dosage formulation.

Embodiment 34: A method of detecting protease activity in vivo in a mammal, said method comprising: administering or causing to be administered to said mammal a probe according to any one of embodiments 1-32, where the peptide in said probe comprises a cleavage site for said protease; and detecting a signal from the fluorophore comprising said probe where said signal indicates that said protease has cleaved said peptide and provides an indication of the activity and/or location of said protease.

Embodiment 35: The method of embodiment 34, wherein said protease activity is at or near a calcium phosphate surface.

Embodiment 36: The method of embodiment 35, wherein said protease activity is at or near a bone surface.

Embodiment 37: The method according to any one of embodiments 34-36, wherein said method comprises detecting and/or localizing a pathology characterized by bone resorption.

Embodiment 38: The method of embodiment 37, wherein the peptide in said probe comprises an amino acid sequence cleaved by cathepsin K and said method comprises detecting and/or localizing a pathology selected from the group consisting of hypocalcemia, hypoparathyroidism, osteoporosis, osteoarthritis, rheumatoid arthritis, multiple myeloma, or osteomyelitis or cancers that metastasize in bone.

Embodiment 39: The method of embodiment 38, wherein a positive signal of from said probe after administration to said mammal is an indicator of the present and/or location of said pathology.

Embodiment 40: The method according to any one of embodiments 34-39, wherein said mammal is a human.

Embodiment 41: The method according to any one of embodiments 34-39, wherein said mammal is a non-human mammal.

Embodiment 42: The method according to any one of embodiments 37-41, wherein said mammal is a mammal suspected of having or being at risk for said pathology.

Embodiment 43: An osteoabsorptive drug delivery vehicle, said vehicle comprising a compound according to Formula IV:

wherein:
R is $CH_2$;
n, x, and y are independently 0 or 1;
$L^1$ is a linker comprising 1 to 6 carbons;
$R^2$ is H or a protecting group; $L^2$ is a linker, wherein said linker is a C1-C12 carbon linker, an amino acid, or a peptide;
P is a peptide comprising a cleavage site for a protease; and
D is a therapeutic moiety wherein said therapeutic moiety is a peptide or small organic molecule.

Embodiment 44: The vehicle of embodiment 43, wherein said vehicle comprises a compound according to Formula V:

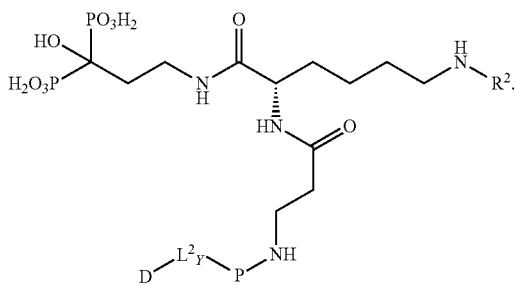

Embodiment 45: The vehicle of embodiment 43, wherein said vehicle comprises a compound according to Formula VI:

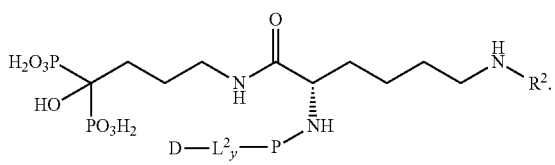

Embodiment 46: The vehicle according to any one of embodiments 43-45, wherein P ranges in length from about 2 amino acids, or from about 4 amino acids, or from about 6 amino acids, or from about 8 amino acids up to about 25 amino acids, or up to about 20 amino acids, or up to about 15 amino acids, or up to about 10 amino acids.

Embodiment 47: The vehicle of embodiment 46, wherein P ranges in length from about 6 amino acid up to about 10 amino acids.

Embodiment 48: The vehicle according to any one of embodiments 43-47, wherein P comprises a cleavage site for a protease selected from the group consisting of cathepsin K, cathepsin B, cathepsin C, cathepsin D, cathepsin E, cathepsin G, cathepsin L, tartrate-resistant acid protease (TRAP), matrix metalloproteinases (MMP)-2, MMP-8, MMP-9, MMP-10, MMP-12, MMP-13, MMP-14, Kallikreins (hK), hK1, PSA (hK3), hK10, hK15, serine proteases uPA and uPAR, plasmin, ceruloplasmin (CP), thrombin, trypsin, fibroblast activation protein (FAP), and caspases.

Embodiment 49: The vehicle of embodiment 48, wherein P comprises an amino acid sequence that is cleaved by cathepsin K.

Embodiment 50: The vehicle of embodiment 48, wherein P consists of an amino acid sequence that is cleaved by cathepsin K.

Embodiment 51: The vehicle according to any one of embodiments 43-49, wherein P comprises the amino acid sequence Gly-His-Pro-Gly-Gly-Pro-Gln-Gly (SEQ ID NO:1).

Embodiment 52: The vehicle according to any one of embodiments 43-49, wherein the amino acid sequence of P consists of the sequence Gly-His-Pro-Gly-Gly-Pro-Gln-Gly (SEQ ID NO:1).

Embodiment 53: The vehicle according to any one of embodiments 43-52, wherein $R^2$ is H.

Embodiment 54: The vehicle according to any one of embodiments 43-52, wherein $R^2$ is a protecting group.

Embodiment 55: The vehicle of embodiment 54, wherein $R^2$ is a protecting group selected from the group consisting of selected from the group consisting of acetyl, amide, 3 to 20 carbon alkyl groups, Fmoc, Tboc, 9-fluoreneacetyl group, 1-fluorenecarboxylic group, 9-florenecarboxylic group, 9-fluorenone-1-carboxylic group, benzyloxycarbonyl, Xanthyl (Xan), Trityl (Trt), 4-methyltrityl (Mtt), 4-methoxytrityl (Mmt), 4-methoxy-2,3,6-trimethyl-benzenesulphonyl (Mtr), Mesitylene-2-sulphonyl (Mts), 4,4-dimethoxybenzhydryl (Mbh), Tosyl (Tos), 2,2,5,7,8-pentamethyl chroman-6-sulphonyl (Pmc), 4-methylbenzyl (MeBzl), 4-methoxybenzyl (MeOBzl), Benzyloxy (BzlO), Benzyl (Bzl), Benzoyl (Bz), 3-nitro-2-pyridinesulphenyl (Npys), 1-(4,4-dimentyl-2,6-diaxocyclohexylidene)ethyl (Dde), 2,6-dichlorobenzyl (2,6-DiCl-Bzl), 2-chlorobenzyloxycarbonyl (2-Cl—Z), 2-bromobenzyloxycarbonyl (2-Br—Z), Benzyloxymethyl (Bom), t-butoxycarbonyl (Boc), cyclohexyloxy (cHxO), t-butoxymethyl (Bum), t-butoxy (tBuO), t-Butyl (tBu), and Trifluoroacetyl (TFA).

Embodiment 56: The vehicle according to any one of embodiments 43-55, wherein D comprises a peptide therapeutic moiety.

Embodiment 57: The vehicle of embodiment 56, wherein D comprises parathyroid hormone or a parathyroid hormone analog.

Embodiment 58: The vehicle of embodiment 57, wherein D comprises a parathyroid hormone analog.

Embodiment 59: The vehicle of embodiment 58, wherein D consists of $PTH_{1-84}$.

Embodiment 60: The vehicle of embodiment 58, wherein D consists of $PTH_{1-34}$ (teriparatide).

Embodiment 61: The vehicle of embodiment 56, wherein D comprises calcitonin.

Embodiment 62: The vehicle according to any one of embodiments 56-61, wherein $L^2$ is absent and D is joined directly to P.

Embodiment 63: The vehicle according to any one of embodiments 56-61, wherein $L^2$ is an amino acid.

Embodiment 64: The vehicle according to any one of embodiments 56-61, wherein $L^2$ is a peptide linker.

Embodiment 65: The vehicle according to any one of embodiments 63-64, wherein $L^2$ is an amino acid or a peptide linker shown in Table 5.

Embodiment 66: The vehicle according to any one of embodiments 43-55, wherein D comprises a small organic molecule (e.g., a drug).

Embodiment 67: The vehicle of embodiment 66, wherein D comprises an antibiotic.

Embodiment 68: The vehicle of embodiment 67, wherein D comprises an antibiotic shown in Table 6.

Embodiment 69: The vehicle of embodiment 66, wherein D comprises an anti-cancer agent.

Embodiment 70: The vehicle of embodiment 69, wherein said anti-cancer agent comprise an agent selected from the group consisting of flourouracil (5-FU), capecitabine, 5-trifluoromethyl-2'-deoxyuridine, methotrexate sodium, raltitrexed, pemetrexed, cytosine Arabinoside, 6-mercaptopurine, azathioprine, 6-thioguanine (6-TG), pentostatin, fludarabine phosphate, cladribine, floxuridine (5-fluoro-2), ribonucleotide reductase inhibitor (RNR), cyclophosphamide, neosar, ifosfamide, thiotepa, 1,3-bis(2-chloroethyl)-1-nitosourea (BCNU), 1,-(2-chloroethyl)-3-cyclohexyl-lnitrosourea, methyl (CCNU), hexamethylmelamine, busulfan, procarbazine HCL, dacarbazine (DTIC), chlorambucil, melphalan, cisplatin, carboplatin, oxaliplatin, bendamustine, carmustine, chloromethine, dacarbazine (DTIC), fotemustine, lomustine, mannosulfan, nedaplatin, nimustine, prednimustine, ranimustine, satraplatin, semustine, streptozocin, temozolomide, treosulfan, triaziquone, triethylene melamine, thioTEPA, triplatin tetranitrate, trofosfamide, uramustine, doxorubicin, daunorubicin citrate, mitoxantrone, actinomycin D, etoposide, topotecan HCL, teniposide (VM-26), irinotecan HCL (CPT-11), camptothecin, belotecan, rubitecan, vincristine, vinblastine sulfate, vinorelbine tartrate, vindesine sulphate, paclitaxel, docetaxel, nanoparticle paclitaxel, abraxane, ixabepilone, larotaxel, ortataxel, tesetaxel, vinflunine, retinoic acid, a retinoic acid derivative, doxirubicin, vinblastine, vincristine, cyclophosphamide, ifosfamide, cisplatin, 5-fluorouracil, a camptothecin derivative, interferon, tamoxifen, and taxol. In certain embodiments the anti-cancer compound is selected from the group consisting of abraxane, doxorubicin, pamidronate disodium, anastrozole, exemestane, cyclophosphamide, epirubicin, toremifene, letrozole, trastuzumab, megestroltamoxifen, paclitaxel, docetaxel, capecitabine, goserelin acetate, and zoledronic acid.

Embodiment 71: The vehicle according to any one of embodiments 66-70, wherein $L^2$ is absent and D is joined directly to P.

Embodiment 72: The vehicle according to any one of embodiments 66-70, wherein $L^2$ is a non-peptide linker.

Embodiment 73: The vehicle of embodiment 72, wherein $L^2$ is a non-peptide linker shown in Table 5.

Embodiment 74: A pharmaceutical formulation said formulation comprising: a vehicle according to any one of embodiments 43-73; and a pharmaceutically acceptable carrier.

Embodiment 75: The formulation of embodiment 74, wherein said formulation is for administration via a modality selected from the group consisting of intraperitoneal administration, topical administration, oral administration, inhalation administration, transdermal administration, subdermal depot administration, and rectal administration.

Embodiment 76: The formulation according to any one of embodiments 74-75, wherein said formulation is a unit dosage formulation.

Embodiment 77: A method of treating a pathology characterized by bone resorption in a mammal, said method comprising: administering or causing to be administered to said mammal, an effective amount of a drug delivery vehicle according to any one of embodiments 43-66, and 69-76, wherein D is selected from the group consisting of parathyroid hormone, a parathyroid hormone analog, calcitonin, a drug that induces bone growth, and an anti-cancer drug.

Embodiment 78: The method of embodiment, wherein said pathology is selected from the group consisting of hypocalcemia, hypoparathyroidism, osteoporosis, osteoarthritis, rheumatoid arthritis, and a cancer.

Embodiment 79: The method of embodiment 78, wherein said pathology is multiple myeloma.

Embodiment 80: The method according to any one of embodiments 77-79, wherein said mammal is a diagnosed for said pathology.

Embodiment 81: The method according to any one of embodiments 77-80, wherein said mammal is a human.

Embodiment 82: The method according to any one of embodiments 77-80, wherein said mammal is a non-human mammal.

Definitions

The term "protease binding site" and "cleavage site" are used interchangeably herein to refer to an amino acid sequence that is recognized and cleaved by a protease. The protease binding site contains a peptide bond that is hydrolyzed by the protease and the amino acid residues joined by this peptide bond are said to form the cleavage site. These amino acids are designated $P_1$ and $P_1'$ for the residues on the amino and carboxyl sides of the hydrolyzed bond respectively.

A fluorophore is a molecule that absorbs light at a characteristic wavelength and then re-emits the light most typically at a characteristic different wavelength. Fluorophores are well known to those of skill in the art and include, but are not limited to rhodamine and rhodamine derivatives, fluorescein and fluorescein derivatives, cyanine and cyanine derivatives, coumarins, chelators with the lanthanide ion series, and the like. A fluorophore is distinguished from a chromophore which absorbs, but does not characteristically re-emit light.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The term also includes variants on the traditional peptide linkage joining the amino acids making up the polypeptide. Preferred "peptides", "polypeptides", and "proteins" are chains of amino acids whose α carbons are linked through peptide bonds. The terminal amino acid at one end of the chain (amino terminal) therefore has a free amino group, while the terminal amino acid at the other end of the chain (carboxy terminal) has a free carboxyl group. As used herein, the term "amino terminus" (abbreviated N-terminus) refers to the free α-amino group on an amino acid at the amino terminal of a peptide or to the α-amino group (imino group when participating in a peptide bond) of an amino acid at any other location within the peptide. Similarly, the term "carboxy terminus" refers to the free carboxyl group on the carboxy terminus of a peptide or the carboxyl group of an amino acid at any other location within the peptide. Peptides also include essentially any polyamino acid including, but not limited to peptide mimetics such as amino acids joined by an ether as opposed to an amide bond.

The polypeptides described herein are preferably written with the amino terminus at the left and the carboxyl terminus at the right.

The term "residue" or "amino acid" as used herein refers to an amino acid that is incorporated into a peptide. The amino acid may be a naturally occurring amino acid and, unless otherwise limited, may encompass known analogs of natural amino acids that can function in a similar manner as naturally occurring amino acids.

As used herein, the phrase "a subject in need thereof" refers to a subject, as described infra, that suffers or is at a risk of suffering (e.g., pre-disposed such as genetically pre-disposed) from the diseases or conditions listed herein.

The terms "subject," "individual," and "patient" may be used interchangeably and refer to a mammal, preferably a human or a non-human primate, but also domesticated mammals (e.g., canine or feline), laboratory mammals (e.g., mouse, rat, rabbit, hamster, guinea pig), and agricultural mammals (e.g., equine, bovine, porcine, ovine). In various embodiments, the subject can be a human (e.g., adult male, adult female, adolescent male, adolescent female, male child, female child) under the care of a physician or other health worker in a hospital, psychiatric care facility, as an outpatient, or other clinical context. In certain embodiments, the subject may not be under the care or prescription of a physician or other health worker.

An "effective amount" refers to an amount effective, at dosages and for periods of time necessary, to achieve the desired therapeutic or prophylactic result. A "therapeutically effective amount" may vary according to factors such as the disease state, age, sex, and weight of the individual, and the ability of the pharmaceutical to elicit a desired response in the individual. A therapeutically effective amount is also one in which any toxic or detrimental effects of a treatment are substantially absent or are outweighed by the therapeutically beneficial effects. In certain embodiments the term "therapeutically effective amount" refers to an amount of an active agent or composition comprising the same that is effective to "treat" a disease or disorder in a mammal (e.g., a patient or a non-human mammal). In one embodiment, a therapeutically effective amount is an amount sufficient to improve at least one symptom associated with a pathology characterized by bone resorption. Illustrative pathologies include, but are not limited to hypocalcemia, hypoparathyroidism, osteoporosis, osteoarthritis, rheumatoid arthritis, osteomyelitis, and certain cancers (e.g., multiple myeloma, bone metastatic breast cancer, and prostate cancer). In certain embodiments, an effective amount is an amount sufficient to prevent advancement or the disease, delay progression, or to cause regression of a disease, or which is capable of reducing symptoms caused by the disease, A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount is less than the therapeutically effective amount.

The terms "treatment," "treating," or "treat" as used herein, refer to actions that produce a desirable effect on the symptoms or pathology of a disease or condition, particularly those that can be effected utilizing the compositions described herein herein, and may include, but are not limited to, even minimal changes or improvements in one or more measurable markers of the disease or condition being treated. Treatments also refers to delaying the onset of, retarding or reversing the progress of, reducing the severity of, or alleviating or preventing either the disease or condition to which the term applies, or one or more symptoms of such disease or condition. "Treatment," "treating," or "treat" does not necessarily indicate complete eradication or cure of the disease or condition, or associated symptoms thereof. In one embodiment, treatment comprises improvement of at least one symptom of a disease being treated. The improvement may be partial or complete. The subject receiving this treatment is any subject in need thereof. Exemplary markers of clinical improvement will be apparent to persons skilled in the art.

The term "mitigating" refers to reduction or elimination of one or more symptoms of that pathology or disease, and/or a reduction in the rate or delay of onset or severity of one or more symptoms of that pathology or disease, and/or the prevention of that pathology or disease.

As used herein, the phrases "improve at least one symptom" or "improve one or more symptoms" or equivalents thereof, refer to the reduction, elimination, or prevention of one or more symptoms of pathology or disease.

The phrase "cause to be administered" refers to the actions taken by a medical professional (e.g., a physician), or a person prescribing and/or controlling medical care of a subject, that control and/or determine, and/or permit the administration of the agent(s)/compound(s) at issue to the subject. Causing to be administered can involve diagnosis and/or determination of an appropriate therapeutic or prophylactic regimen, and/or prescribing particular agent(s)/compounds for a subject. Such prescribing can include, for example, drafting a prescription form, annotating a medical record, and the like.

DETAILED DESCRIPTION

It was desired to extend tissue half-life and improve bone uptake of a fluorogenic substrate of cathepsin K. To accomplish this, the 1,1-bisphosphonate moiety was incorporated into a quenched fluorescent FRET system linked by a peptide sequence cleavable by cathepsin K. Accordingly, in certain embodiments, the structures, preparation, and applications of bone-targeted, FRET-quenched, fluorescent probe activated by the protease enzyme cathepsin K are provided. Osteoabsorptive Fluorogenic Probes.

Figure 1:
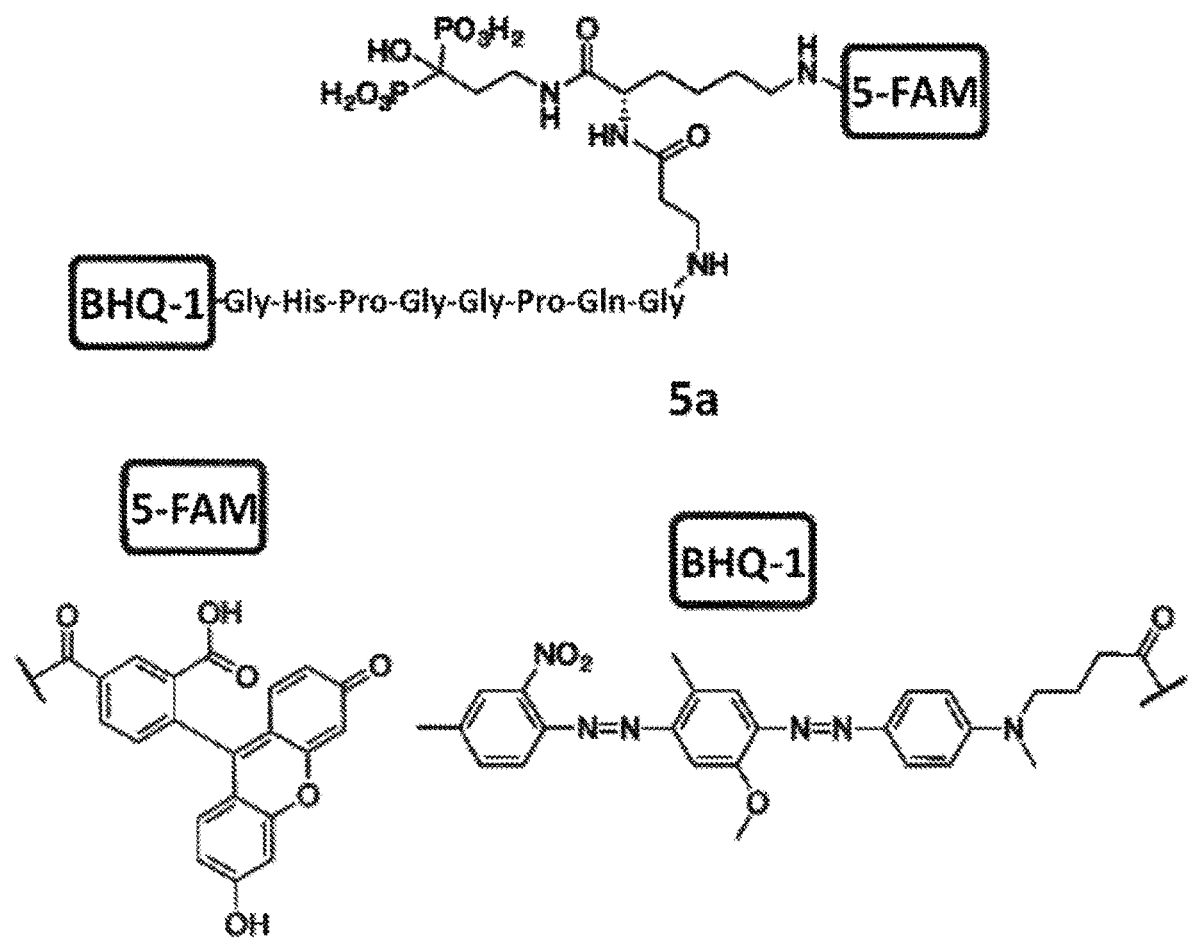
FIG. 1 shows the structure of the OFS-1 probe. While illustrated with 5-FAM (5-carboxyfluorescein) fluorophore and BHQ-1 quencher, it will be recognized that in certain embodiments, the position of the fluorophore and quencher can be reversed and/or different fluorophores and/or quenchers can be utilized. Additionally, while illustrated with the Gly-His-Pro-Gly-Gly-Pro-Gln-Gly (SEQ ID NO:1) cathepsin K substrate, it will be appreciated that other peptides cleavable by cathepsin can be utilized as well as substrates cleavable by other proteases.

One such probe illustrated probe is OFS-1 (see, e.g., FIG. 1), having a Kcat=0.2±0.03 s−1 and a Km=1.7±0.2 μM in aqueous solution at 37° C., pH 5.5. This compound is avidly adsorbed on calcium phosphate substrates. The combination of strong bone binding and protease sensitivity makes this molecules useful as a sentinel probes that remains in place and respond when activated by cathepsin K activity. The system is designed to generate a fluorescent signal when such cleavage occurs.

It will be recognized, however that OFS-1 is illustrative and non-limiting. For example, in certain embodiments, the location of the fluorophore and the quencher can be reversed. While OFS-1 is illustrated with a 5-FAM fluorophore and black hole quencher-1 (BHQ-1) it will be recognized that other combinations of fluorophores and quenchers can be utilized. Additionally variations in the length of the backbone joining the bisphosphonate and the presence of absence of a linker attaching the peptide to the rest of the molecule are contemplated. Accordingly, in certain embodiments, a probe according to Formula I is contemplated:

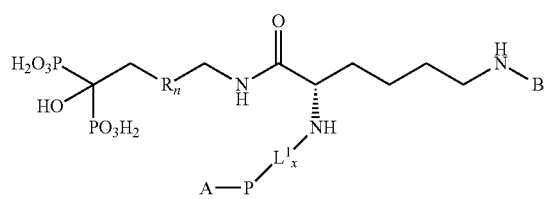

I wherein R is CH$_2$ and n is 0 or 1, or, or 2, or 3, or 4, or 5, or 6, and in certain embodiments n is 0 or 1 (e.g., R is present or absent)), L$^1$ is a linker comprising 1 to 6 carbons which may also be present or absent (e.g., x is 0 or 1), P is a peptide comprising a cleavage site for a protease; and A is a quencher and B is a fluorophore, or B is a quencher and A is a fluorophore. It is noted that A and B are selected to emitting/absorbing wavelengths suitable to create a quenched FRET system.

In certain embodiments the probe is a probe according to Formula I:

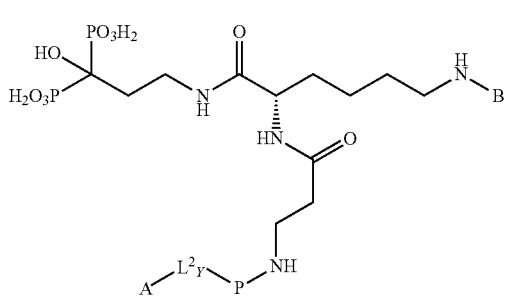

II where L$^2$ is a linker (e.g., a C1-C12 carbon linker, an amino acid, or a peptide 0, and y is 0 or 1.

In certain embodiments the probe is a probe according to Formula III:

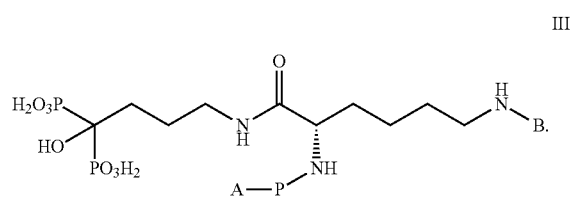

III

In certain embodiments P ranges in length from about 2 amino acids, or from about 4 amino acids, or from about 6 amino acids, or from about 8 amino acids up to about 25 amino acids, or up to about 20 amino acids, or up to about 15 amino acids, or up to about 10 amino acids. In certain embodiments P ranges in length from about 2 amino acids up to about 10 amino acids. In certain embodiments P is about 8 amino acids in length.

In various embodiments peptide P comprises (or consists of) an amino acid sequence that is cleaved by a protease (e.g., a serine protease, a cysteine protease, a threonine protease, an aspartic protease, a glutamic protease, a metalloprotease, an asparagine peptide lyase, and the like). In certain embodiments P comprises or consists of an amino acid sequence that is cleaved by a protease selected from the group consisting of cathepsin K, cathepsin B, cathepsin C, cathepsin D, cathepsin E, cathepsin G, cathepsin L, tartrate-resistant acid protease (TRAP), matrix metalloproteinases (MMP)-2, MMP-8, MMP-9, MMP-10, MMP-12, MMP-13, MMP-14, Kallikreins (hK), hK1, PSA (hK3), hK10, hK15, serine proteases uPA and uPAR, plasmin, ceruloplasmin (CP), thrombin, trypsin, fibroblast activation protein (FAP), and caspases. In certain embodiments P comprises or consists of an amino acid sequence that is cleaved by cathepsin K. In certain embodiments P comprises or consists of the amino acid sequence Gly-His-Pro-Gly-Gly-Pro-Gln-Gly (SEQ ID NO:1).

Protease recognition (cleavage) sites are well known to those of skill in the art. Illustrative, but non-limiting sequences that are cleaved by various proteases are shown in Table 1. In certain embodiments P comprises or consists of an amino acid sequence shown in Table 1.

TABLE 1

Illustrative, but non-limiting, proteases and sequences cleaved by those proteases.

| Protease | Sequence Cleaved by Protease | SEQ ID NO |
|---|---|---|
| Cathepsin K | Gly-His-Pro-Gly-Gly-Pro-Gln-Gly | 1 |
| Cathepsin B | Abz-GIVRAK(Dnp)-OH | 2 |

TABLE 1-continued

Illustrative, but non-limiting, proteases and sequences cleaved by those proteases.

| Protease | Sequence Cleaved by Protease | SEQ ID NO |
|---|---|---|
| Cathepsin C | Gly-Phe-4MβNA | |
| Cathepsin D | N-Acetyl-Arg-Gly-Phe-Phe-Pro | 3 |
| | Acetyl-Gly-Lys-Pro-Ile-Leu-Phe-Phe-Arg-Leu-Lys(DNP)-D-Arg | 4 |
| Cathepsin E | Gly-Ser-Pro-Ala-Phe-Leu-Ala-Lys(Dnp)-D-Arg | 5 |
| Cathepsin G | Ala-Ala-Pro-Phe and | 6 |
| | Ala-Ala-Pro-Met | 7 |
| Cathepsin L | Xaa-Xaa-Xaa-Hydrophobic-Phe-Arg-Xaa-Xaa-Xaa | 8 |
| | Xaa-Xaa-Xaa-Aromatic-Phe-Arg-Xaa-Xaa-Xaa | 9 |
| | Xaa-Xaa-Xaa-Hydrophobic-Arg-Arg-Xaa-Xaa-Xaa | 10 |
| | Xaa-Xaa-Xaa-Aromatic-Arg-Arg-Xaa-Xaa-Xaa | 11 |
| Tartrate-resistant acid protease (TRAP) | | |
| Matrix metalloproteinase-2 (MMP)-2 | HXXX Hy | 12 |
| | Gly-Pro-Leu-Gly-Ile-Ala-Gly-Gln | 13 |
| MMP-8 | | |
| MMP-9 | Pro-Xaa-Xaa-Hydrophobic-(Ser/Thr) | 14 |
| MMP-10 | | |
| MMP-12 | Pro-Leu-Gly-Leu and | 15 |
| | Pro-Ala-Asn-Leu | 16 |
| MMP-13 | Pro-Leu-Gly-Leu and | 15 |
| | Pro-Ala-Asn-Leu | 16 |
| MMP-14 | Pro-Leu-Gly-Leu and | 15 |
| | Pro-Ala-Asn-Leu | 16 |
| Kallikreins (hK) | | |
| hK1 | | |
| PST (hK3) | | |
| hK10 | | |
| hK15 | | |
| Serine proteases | | |
| uPA | | |
| uPAR | | |
| Plasmin | | |
| Ceruloplasmin | | |
| Thrombin | | |
| Trypsin | | |
| Fibroblast activation protein (FAP) | | |
| Caspases | | |

Xaa = any amino acid residue
Hydrophobic = Ala, Val, Leu, Ile, Phe, Trp, Tyr
Aromatic = Phe, Trp, His, Tyr As noted above, in certain embodiments A in Formula I is a quencher, while B is a fluorophore, or conversely, B is a quencher and A is a fluorophore. While OFS-1 utilizes 5-FAM as a fluorophore and BHQ-1® as a quencher, it will be recognized that other fluorophores and quenchers can be utilized. For example, in certain embodiment a far red to near infrared fluorophore (e.g., emission from about 650 nm to about 1200 nm or to about 1400 nm) can be utilized to facilitate in vivo imaging. Illustrative, fluorophores are shown in Table 2.

TABLE 2

Illustrative, but non-limiting, fluorophores for use in the probes described herein.

| Fluorophore | Absorption max (nm) | Emission max (nm) |
|---|---|---|
| BODIPY FL | 502 | 510 |
| FAM | 495 | 520 |
| Oregon Green 488 | 494 | 517 |
| Rhodamine Green | 503 | 528 |
| Oregon Green 514 | 506 | 526 |
| TET | 521 | 536 |
| Cal Gold | 522 | 544 |
| BODIPY R6G | 528 | 547 |
| Yakima Yellow | 526 | 548 |
| JOE | 520 | 548 |
| HEX | 535 | 556 |
| Cal Orange | 540 | 561 |
| BODIPY TMR-X | 544 | 570 |
| Quasar-570/Cy3 | 550 | 570 |
| TAMRA | 555 | 576 |
| Rhodamine Red-X | 560 | 580 |
| Redmond Red | 554 | 590 |
| BODIPY 581/591 | 581 | 591 |
| Cy3.5 | 581 | 596 |
| ROX | 575 | 602 |
| Cal Red/Texas Red | 593 | 613 |
| BODIPY TR-X | 588 | 616 |
| BODIPY 630/665-X | 647 | 665 |
| Pulsar-650 | 460 | 650 |
| Quasar-670/Cy5 | 649 | 670 |
| Cy5.5 | 675 | 694 |
| ALEXA FLUOR ® AF647 | 650 | 665 |
| ALEXA FLUOR ® AF660 | 663 | 690 |
| ALEXA FLUOR ® AF680 | 679 | 702 |
| ALEXA FLUOR ® AF700 | 702 | 723 |
| ALEXA FLUOR ® AF750 | 749 | 775 |
| ALEXA FLUOR ® AF790 | 782 | 805 |

Figure 2:
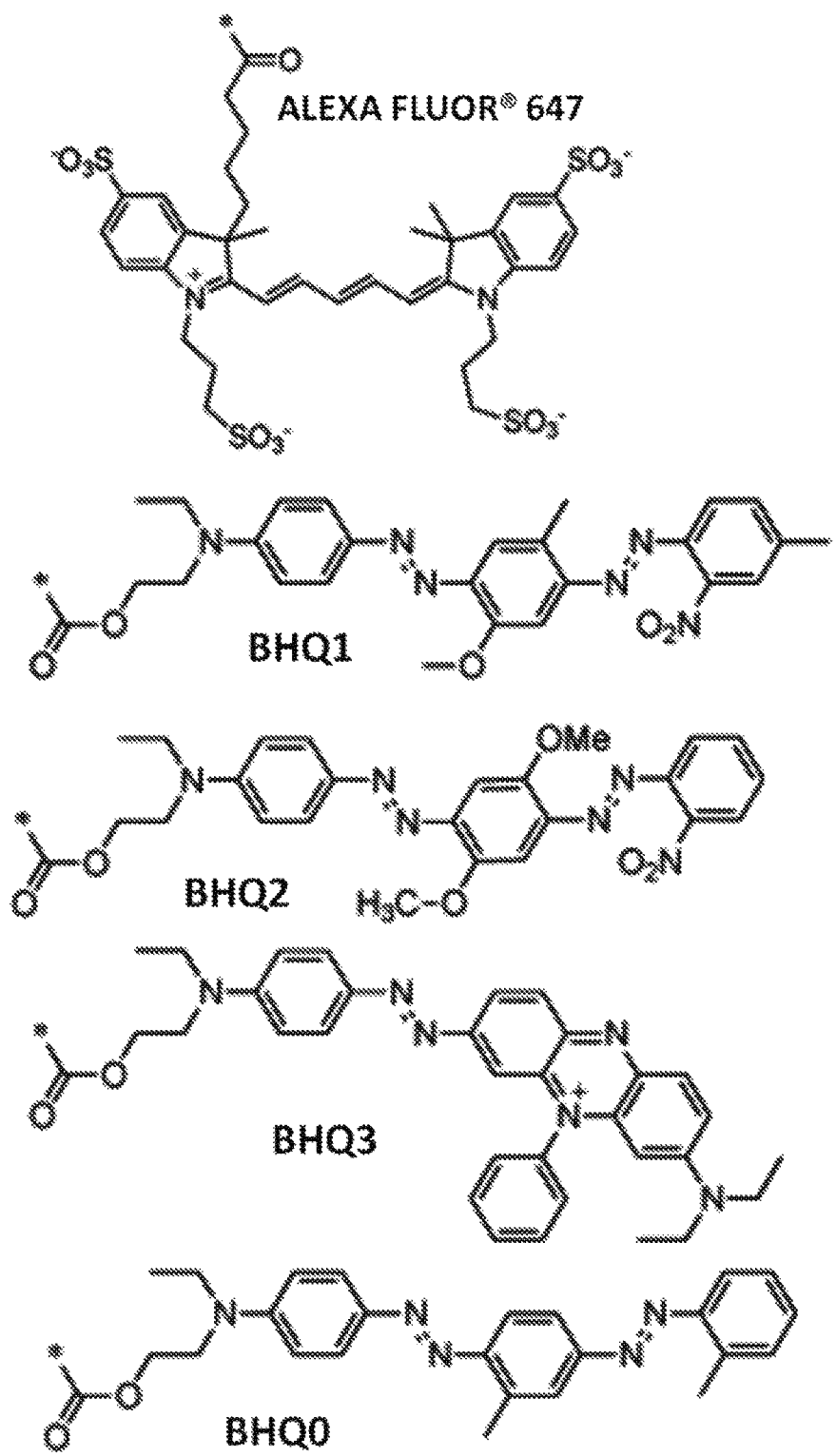
FIG. 2 illustrates the structures of various black hole quenchers (BHQ) and ALEXA FLUOR® 647 (AF647).

Similarly, quenchers are also well known to those of skill in the art. Illustrative quenchers are shown in Table 3 (see also, FIG. 2).

TABLE 3

Illustrative, but non-limiting quenchers.

| Quencher | Absorption max (nm) |
|---|---|
| Dabcyl | 453 |
| QSY 35 | 475 |
| BHQ-0 | 495 |
| Eclipse | 522 |
| BHQ-1 | 534 |
| QSY 7 | 560 |
| QSY 9 | 562 |
| BHQ-2 | 579 |
| ElleQuencher | 630 |
| Iowa Black | 651 |
| QSY 21 | 661 |
| TAMRA | 544 |
| BHQ-3 | 672 |

Methods of selecting fluorophores and quenchers for FRET systems are well known to those of skill in the art. Typically, the fluorophore/quencher pair is selected to produce effective quenching of the fluorophore when the fluorophore are contacting or in close proximity and a detectable signal when the molecules are separated. Thus, a quencher is typically selected that absorbs at, or near, the emission maximum of the fluorophore. Illustrative, but non-limiting combinations of fluorophore and quencher are shown in in Table 4.

TABLE 4

Illustrative fluorophore/quencher pairs.

| Reporter (Fluorophore) | Excitation Max/Emission max (nm) | Quencher / Quenching Range / Quenching Max | | | | | |
|---|---|---|---|---|---|---|---|
| | | BHQ-1 ® 480-580 535 (nm) | BHQ-2 ® 550-650 579 (nm) | BHQ-3 ® 620-730 672 (nm) | ECLIPSE 390-625 522 (nm) | DABCYL 380-550 453 (nm) | TAMRA 470-560 544 (nm) |
| LC ®Cyan500 | 490/500 | X | — | — | — | X | — |
| 6-FAM | 495/520 | X | X | — | — | X | X |
| 5-FAM | 495/520 | X | X | — | — | X | X |
| FITC | 490/525 | X | X | — | — | X | X |
| TET | 521/536 | X | — | — | — | X | X |
| JOE | 522/548 | X | — | — | — | X | X |
| Yakima Yellow | 530/549 | X | X | — | — | X | X |
| HEX | 535/556 | X | X | — | X | X | X |
| Cy3 | 546/563 | — | X | — | X | — | — |
| TAMRA | 564/579 | — | X | — | X | X | — |
| ROX | 576/601 | — | X | — | X | — | X |
| Texas Red | 586/610 | — | X | — | X | — | — |
| LC ®Red610 | 590/610 | — | X | — | X | — | — |
| LC ®Red640 | 625/640 | — | X | X | X | — | — |
| Cy5 | 646/662 | — | X | X | X | — | — |
| Cy5.5 | 683/705 | — | X | X | X | — | X |
| IRD700 | 685/705 | — | X | X | X | — | X |
| AF647 | 650/665 | | | X | | | |

X = effective quenching.

In various embodiments, OFS-1, and it is believed the other probes described herein, gives a fluorescent signal in response to resorptive activity of monocyte-derived human osteoclasts in culture on calcium phosphate coated microwells. Resorbing cells are fluorescently labeled by cleavage and uptake of the probe. The substrate under the cell is labeled as well and increased fluorescence persists after the osteoclast migrates giving a convenient way to track their migration. Multiple myeloma is the most frequent primary malignant neoplasm of the skeletal system and develops debilitating or life-limiting skeletal-related events. It is well known that multiple myeloma pathologically activate osteoclastic bone resorption. When co-cultured with human multiple myeloma cells (8226-LUC), human osteoclasts exhibited significantly increased OFS-1 activation.

As described in the Examples, preliminary experiments in young mice show increased fluorescent signal in maxilla ex vivo in around the site of a tooth extraction. Fluorescent control probe without quencher gave even labeling of the entire maxilla. Separately, OFS-1 was injected to humanized mice carrying 8226-LUC human multiple myeloma cells. Multiple myeloma cells were found engrafted at lumbar and cervical bones as well as femurs and tibia. Strong activation of OFS-1 was detected at multiple myeloma grafted sites. In view of this OFS-1 and the other probes described herein provide promising new imaging reagents for the study of cathepsin k, osteoclasts, and their role in various disease process as wells as for the diagnosis and/or localization of various pathologies characterized by bone resorption.

The foregoing osteoabsorptive fluorogenic probes described herein are illustrative and non-limiting. Using the teachings provided herein, numerous alternative probes comprising, for example, different enzyme substrates, different therapeutic fluorophores and quenchers, and the like will be available to one of skill in the art.

Uses of Probes.

The osteoabsorptive fluorogenic probe, described herein are useful for detecting activity of a protease (e.g., a protease that cleaves the peptide "P" in the probe) in vitro or in vivo. Typically, in vivo, the probes are effective for detecting the activity of the protease (e.g., cathepsin K, cathepsin B, cathepsin C, cathepsin D, cathepsin E, cathepsin G, cathepsin L, tartrate-resistant acid protease (TRAP), matrix metalloproteinases (MMP)-2, MMP-9, MMP-10, MMP-12, MMP-13, MMP-14, etc.) at or near a calcium surface (e.g., the surface of a bone).

In certain embodiments the probes can be effectively utilized to detect pathologies characterized by bone resorption, e.g., as characterized by the presence and activity of cathepsin K. Accordingly, in certain embodiments, the probes (particularly probes in which "P" comprise or consists of an amino acid sequence cleaved by cathepsin K) are useful for detecting and/or localizing a pathology selected from the group consisting of hypocalcemia, hypoparathyroidism, osteoporosis, osteoarthritis, rheumatoid arthritis, osteomyelitis and a cancer (e.g., multiple myeloma, breast cancer, prostate cancer, etc.).

Thus, in certain embodiments, methods of detecting protease activity in vivo in a mammal, are provide where the methods comprise administering or causing to be administered to said mammal an osteoabsorptive fluorogenic probe as described herein where the peptide in the probe comprises a cleavage site for the protease; and detecting a signal from the fluorophore comprising said probe where said signal indicates that said protease has cleaved said peptide and provides an indication of the activity and/or location of the enzyme. In certain embodiments such methods comprise detecting and/or localizing a pathology characterized by bone resorption. Illustrative pathologies include, but are not limited to hypocalcemia, hypoparathyroidism, osteoporosis, osteoarthritis, rheumatoid arthritis, osteomyelitis, and cancer (e.g., multiple myeloma, breast cancer, prostate cancer, etc.). Thus, in certain embodiments, such methods can provide a diagnosis (e.g., in the context of a differential diagnosis) of the pathology and may provide staging of the pathology. In certain embodiments the methods can provide detection/diagnosis of device-associated infections, e.g. titanium bone replacements, and/or other orthopedic implants (e.g., artificial joints, bone screws, and a bone nails, and the like).

In this regard, it is noted that probes comprising a far-red, or a near infrared fluorophore may be more effective for in vivo studies due to the greater tissue penetration depth of far red and NIR light and the reduced tissue autofluorescence at these wavelengths compared to visible light. Additionally, it is noted that effects due to the pH sensitivity of the fluorophore can be reduced by using cyanine based NIR dyes that have minimal pH sensitivity.

Bisphosphonate Targeted Drugs.

In certain embodiments the probes described herein can be effectively modified for the delivery of therapeutic moieties to a tissue comprising calcium (e.g., to a bone surface).

In particular, it is contemplated that the bisphosphonate will target a delivery vehicle comprising the therapeutic moiety to a tissue comprising calcium. The bisphosphonate is coupled to the therapeutic moiety through a peptide comprising an amino acid sequence that is cleaved by a protease at or near the target site (e.g., cathepsin K, cathepsin B, cathepsin C, cathepsin D, cathepsin E, cathepsin G, cathepsin L, tartrate-resistant acid protease (TRAP), matrix metalloproteinases (MMP)-2, MMP-9, MMP-10, MMP-12, MMP-13, MMP-14, etc.) thereby freeing the therapeutic moiety a the target site.

Accordingly, in certain embodiments an osteoabsorptive drug delivery vehicle, is provided where the vehicle comprises a compound according to Formula IV:

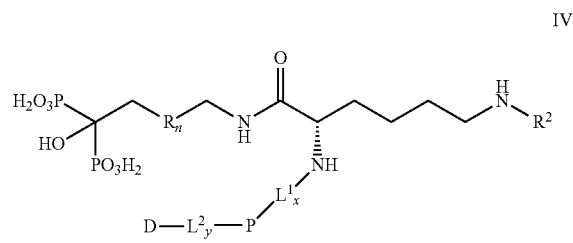

IV where R is $CH_2$, n, x, and y are independently 0 to 6 (e.g., 0, 1, 2, 3, 4, 5, or 6), and in certain embodiments 0 or 1 (e.g., R, $L^1$, and $L^2$ is independently present or absent), $L^1$ is a linker comprising 1 to 6 carbons, $R^2$ is H or a protecting group, $L^2$ is a linker, wherein this linker is a C1-C12 carbon linker, an amino acid, or a peptide, P is a peptide comprising a cleavage site for a protease; and D is a therapeutic moiety wherein said therapeutic moiety is a peptide or small organic molecule.

In certain embodiments $L^1$ is present (e.g., x is 1). In certain embodiments $L^1$ is present and R is absent (e.g., n is 0) and the vehicle comprises a compound according to Formula V:

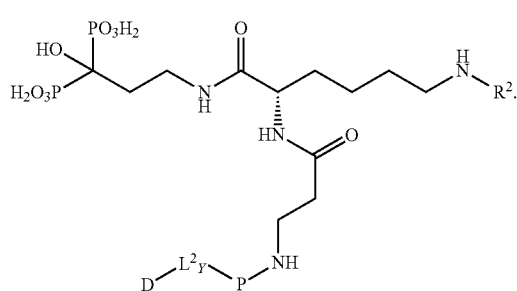

V

In certain embodiments L1 is absent (e.g., x is 0). In certain embodiments R is present (e.g., n is 1). In certain embodiments R is present and $L^1$ is absent and the vehicle comprises a compound according to Formula VI:

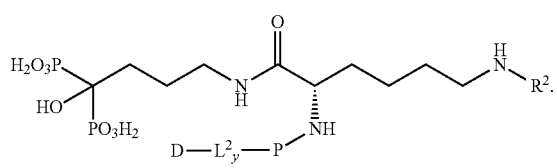

VI

In typical embodiments, P comprise an amino acid sequence as described above. Thus, for example, in certain embodiments, P ranges in length from about 2 amino acids, or from about 4 amino acids, or from about 6 amino acids, or from about 8 amino acids up to about 25 amino acids, or up to about 20 amino acids, or up to about 15 amino acids, or up to about 10 amino acids. In certain embodiments P ranges in length from about 2 amino acids up to about 10 amino acids. In certain embodiments P is about 8 amino acids in length. In certain embodiments P comprises a cleavage site for a protease selected from the group consisting of cathepsin K, cathepsin B, cathepsin C, cathepsin D, cathepsin E, cathepsin G, cathepsin L, tartrate-resistant acid protease (TRAP), matrix metalloproteinases (MMP)-2, MMP-8, MMP-9, MMP-10, MMP-12, MMP-13, MMP-14, Kallikreins (hK), hK1, PSA (hK3), hK10, hK15, seriene proteases uPA and uPAR, plasmin, ceruloplasmin (CP), thrombin, trypsin, fibroblast activation protein (FAP), and caspases. In certain embodiments P comprises or consists of an amino acid sequence that is cleaved by cathepsin K. In certain embodiments P comprises or consists of the amino acid sequence Gly-His-Pro-Gly-Gly-Pro-Gln-Gly (SEQ ID NO:1).

In certain embodiments $R^2$ is H, while in other embodiments, $R^2$ is a protecting group (e.g., a protecting group selected from the group consisting of selected from the group consisting of acetyl, amide, 3 to 20 carbon alkyl groups, Fmoc, Tboc, 9-fluoreneacetyl group, 1-fluorenecarboxylic group, 9-florenecarboxylic group, 9-fluorenone-1-carboxylic group, benzyloxycarbonyl, Xanthyl (Xan), Trityl (Trt), 4-methyltrityl (Mtt), 4-methoxytrityl (Mint), 4-methoxy-2,3,6-trimethyl-benzenesulphonyl (Mtr), Mesitylene-2-sulphonyl (Mts), 4,4-dimethoxybenzhydryl (Mbh), Tosyl (Tos), 2,2,5,7,8-pentamethyl chroman-6-sulphonyl (Pmc), 4-methylbenzyl (MeBzl), 4-methoxybenzyl (MeOBzl), Benzyloxy (BzlO), Benzyl (Bzl), Benzoyl (Bz), 3-nitro-2-pyridinesulphenyl (Npys), 1-(4,4-dimentyl-2,6-diaxocyclohexylidene)ethyl (Dde), 2,6-dichlorobenzyl (2,6-DiCl-Bzl), 2-chlorobenzyloxycarbonyl (2-Cl—Z), 2-bromobenzyloxycarbonyl (2-Br—Z), Benzyloxymethyl (Bom), t-butoxycarbonyl (Boc), cyclohexyloxy (cHxO), t-butoxymethyl (Bum), t-butoxy (tBuO), t-Butyl (tBu), and Trifluoroacetyl (TFA)).

Essentially any therapeutic moiety (D) can be attached to peptide "P". In certain embodiments the therapeutic moiety is attached to P directly, through an amino acid, or through a peptide linker.

In certain embodiments, particularly where the therapeutic moiety "D" comprises a peptide (polypeptide) the therapeutic moiety is readily coupled directly to P, or coupled to P through an amino acid, coupled to P through a peptide linker, or conjugated to P. Where the therapeutic moiety is not a peptide the therapeutic moiety can be conjugated to P. In certain embodiments "P" and the therapeutic moiety are attached directly via naturally occurring reactive groups or the therapeutic moiety and/or the peptide "P" can be functionalized to provide such reactive groups.

In various embodiments the therapeutic moiety "D" is attached to peptide "P" via a linker ($L^2$) which can comprise, inter alia, a peptide, an amino acid, and a non-peptide linker.

In certain embodiments the linker is or comprises a functional group. Functional groups include monofunctional linkers comprising a reactive group as well as multifunctional linkers comprising two or more reactive groups capable of forming a bond with two or more different functional targets (e.g., the therapeutic moiety and the peptide "P"). In some preferred embodiments, the multifunctional linkers are heterobifunctional linkers comprising two or more different reactive groups.

Suitable reactive groups include, but are not limited to thiol (—SH), carboxylate (COOH), carboxyl (—COOH), carbonyl, amine ($NH_2$), hydroxyl (—OH), aldehyde (—CHO), alcohol (ROH), ketone ($R_2CO$), active hydrogen, ester, sulfhydryl (SH), phosphate (—$PO_3$), or photoreactive moieties. Amine reactive groups include, but are not limited to e.g., isothiocyanates, isocyanates, acyl azides, NHS esters, sulfonyl chlorides, aldehydes and glyoxals, epoxides and oxiranes, carbonates, arylating agents, imidoesters, carbodiimides, and anhydrides. Thiol-reactive groups include, but are not limited to e.g., haloacetyl and alkyl halide derivates, maleimides, aziridines, acryloyl derivatives, arylating agents, and thiol-disulfides exchange reagents. Carboxylate reactive groups include, but are not limited to e.g., diazoalkanes and diazoacetyl compounds, such as carbonyldiimidazoles and carbodiimides. Hydroxyl reactive groups include, but are not limited to e.g., epoxides and oxiranes, carbonyldiimidazole, oxidation with periodate, N,N'-disuccinimidyl carbonate or N-hydroxylsuccimidyl chloroformate, enzymatic oxidation, alkyl halogens, and isocyanates. Aldehyde and ketone reactive groups include, but are not limited to e.g., hydrazine derivatives for schiff base formation or reduction amination. Active hydrogen reactive groups include, but are not limited to e.g., diazonium derivatives for mannich condensation and iodination reactions. Photoreactive groups include, but are not limited to e.g., aryl azides and halogenated aryl azides, benzophenones, diazo compounds, and diazirine derivatives.

Other suitable reactive groups and classes of reactions useful for linking the therapeutic moiety "D" to the peptide "P" include those that are well known in the art of bioconjugate chemistry. In certain embodiments classes of reactions available with reactive chelates are those which proceed under relatively mild conditions. These include, but are not limited to, nucleophilic substitutions (e.g., reactions of amines and alcohols with acyl halides, active esters), electrophilic substitutions (e.g., enamine reactions), and additions to carbon-carbon and carbon-heteroatom multiple bonds (e.g., Michael reaction, Diels-Alder addition). These and other useful reactions are discussed in, for example, March (1985) *Advanced Organic Chemistry*, 3rd Ed., John Wiley & Sons, New York, Hermanson (1996) *Bioconjugate Techniques*, Academic Press, San Diego; and Feeney et al. (1982) Modification of Proteins; *Advances in Chemistry Series*, Vol. 198, American Chemical Society, Washington, D.C.

A "linker" or "linking agent" as used herein, is a molecule that is used to join two or more molecules. In certain embodiments the linker is typically capable of forming covalent bonds to both molecule(s) (e.g., the therapeutic moiety "D" and the peptide "P"). Suitable linkers are well known to those of skill in the art and include, but are not limited to, straight or branched-chain carbon linkers, heterocyclic carbon linkers, or peptide linkers. In certain embodiments the linkers can be joined to the constituent amino acids through their side groups (e.g., through a disulfide linkage to cysteine). However, in certain embodiments, the linkers will be joined to the alpha carbon amino and carboxyl groups of the terminal amino acids.

In certain embodiments the linking agent is a heterobifunctional crosslinker comprising two or more different reactive groups that form a heterocyclic ring that can interact with a peptide. For example, a heterobifunctional crosslinker such as cysteine may comprise an amine reactive group and a thiol-reactive group can interact with an aldehyde on a derivatized peptide. Additional combinations of reactive groups suitable for heterobifunctional crosslinkers include, for example, amine- and sulfhydryl reactive groups; carbonyl and sulfhydryl reactive groups; amine and photoreactive groups; sulfhydryl and photoreactive groups; carbonyl and photoreactive groups; carboxylate and photoreactive groups; and arginine and photoreactive groups. In one embodiment, the heterobifunctional crosslinker is SMCC.

Many procedures and linker molecules for attachment of various molecules to peptides or proteins are known (see, e.g., European Patent Application No. 188,256; U.S. Pat. Nos. 4,671,958, 4,659,839, 4,414,148, 4,699,784; 4,680, 338; 4,569,789; and 4,589,071; and Borlinghaus et al. (1987) *Cancer Res.* 47: 4071-4075). Illustrative non-peptide linkers are shown in Table 5.

In certain embodiments where therapeutic moiety "D" is a peptide (polypeptide) the peptide can be fused directly to the therapeutic moiety, fused through an amino acid, or fused through a peptide linker.

In certain embodiments "D" attached to "P" (directly, through an amino acid, or through a peptide linker) is simply synthesized directly using methods of chemical peptide synthesis.

In certain embodiments, particularly where the therapeutic moiety "D" is a large peptide, the fused "D"-"P" can be recombinantly expressed as a fusion protein. Generally this involves creating a DNA sequence that encodes the fusion protein, placing the DNA in an expression cassette under the control of a particular promoter, expressing the protein in a host, isolating the expressed protein and, if required, renaturing the protein.

DNA encoding the fusion proteins can be prepared by any suitable method, including, for example, cloning and restriction of appropriate sequences or direct chemical synthesis by methods such as the phosphotriester method of Narang et al. (1979) *Meth. Enzymol.* 68: 90-99; the phosphodiester method of Brown et al. (1979) *Meth. Enzymol.* 68: 109-151; the diethylphosphoramidite method of Beaucage et al. (1981) *Tetra. Lett.,* 22: 1859-1862; and the solid support method of U.S. Pat. No. 4,458,066.

Chemical synthesis produces a single stranded oligonucleotide. This can be converted into double stranded DNA by hybridization with a complementary sequence or by polymerization with a DNA polymerase using the single strand as a template. One of skill would recognize that while chemical synthesis of DNA is limited to sequences of about 100 bases, longer sequences can be obtained by the ligation of shorter sequences.

Alternatively, subsequences can be cloned and the appropriate subsequences cleaved using appropriate restriction enzymes. The fragments can then be ligated to produce the desired DNA sequence.

In certain embodiments, DNA encoding fusion proteins of the present invention may be cloned using DNA amplification methods such as polymerase chain reaction (PCR). Thus, for example, the therapeutic moiety "D" can PCR amplified, using a sense primer containing the restriction site for NdeI and an antisense primer containing the restriction site for HindIII. This produces a nucleic acid encoding the therapeutic moiety "D" and having terminal restriction sites. Similarly peptide "P" and/or peptide "P"-$L^2$ (where L2 is an amino acid or a peptide linker) can be provided having complementary restriction sites. Ligation of sequences and insertion into a vector produces a vector encoding the fusion protein.

As noted above, while the therapeutic moiety "D" and peptide "P" can be directly joined together, one of skill will appreciate that they can be separated by linker consisting of one or more amino acids. Generally the spacer will have no specific biological activity other than to join the proteins or to preserve some minimum distance or other spatial relationship between them. However, the constituent amino acids of the spacer may be selected to influence some property of the molecule such as the folding, net charge, or hydrophobicity.

The nucleic acid sequences encoding the fusion proteins can be expressed in a variety of host cells, including *E. coli*, other bacterial hosts, yeast, and various higher eukaryotic cells such as the COS, CHO and HeLa cells lines and myeloma cell lines. The recombinant protein gene will be operably linked to appropriate expression control sequences for each host. For *E. coli* this includes a promoter such as the T7, trp, or lambda promoters, a ribosome binding site and preferably a transcription termination signal. For eukaryotic cells, the control sequences will include a promoter and preferably an enhancer derived from immunoglobulin genes, SV40, cytomegalovirus, etc., and a polyadenylation sequence, and may include splice donor and acceptor sequences.

The plasmids can be transferred into the chosen host cell by well-known methods such as calcium chloride transformation for *E. coli* and calcium phosphate treatment or electroporation for mammalian cells. Cells transformed by the plasmids can be selected by resistance to antibiotics conferred by genes contained on the plasmids, such as the amp, gpt, neo and hyg genes.

Once expressed, the recombinant fusion proteins can be purified according to standard procedures of the art, including ammonium sulfate precipitation, affinity columns, column chromatography, gel electrophoresis and the like (see, generally, R. Scopes (1982) *Protein Purification*, Springer-Verlag, N.Y.; Deutscher (1990) *Methods in Enzymology Vol. 182: Guide to Protein Purification.*, Academic Press, Inc. N.Y.). Substantially pure compositions of at least about 90 to 95% homogeneity are preferred, and 98 to 99% or more homogeneity are most preferred for pharmaceutical uses. Once purified, partially or to homogeneity as desired, the polypeptides may then be used therapeutically.

One of skill in the art would recognize that after chemical synthesis, biological expression, or purification, the fusion protein may possess a conformation substantially different than the native conformations of the constituent polypeptides. In this case, it may be necessary to denature and reduce the polypeptide and then to cause the polypeptide to re-fold into the preferred conformation. Methods of reducing and denaturing proteins and inducing re-folding are well known to those of skill in the art (See, Debinski et al. (1993) *J Biol. Chem.*, 268: 14065-14070; Kreitman and Pastan (1993) *Bioconjug. Chem.*, 4: 581-585; and Buchner, et al. (1992) *Anal. Biochem.*, 205: 263-270).

One of skill would recognize that modifications can be made to the fusion proteins without diminishing their biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids placed on either terminus to create conveniently located restriction sites or termination codons.

As indicated above, in various embodiments an amino acid, or a peptide linker is used to join the therapeutic moiety "D" to the peptide "P". In various embodiments the peptide linker is relatively short, typically about 20 amino acids or less or about 15 amino acids or less or about 10 amino acids or less or about 8 amino acids or less or about 5 amino acids or less or about 3 amino acids or less, or is a single amino acid. Suitable illustrative linkers include, but are not limited to PSGSP ((SEQ ID NO:2), ASASA (SEQ ID NO: 3), or GGG. In certain embodiments longer linkers such as (GGGGS)$_3$ (SEQ ID NO:4) can be used. Illustrative peptide linkers and other linkers are shown in Table 5.

TABLE 5

Illustrative peptide and non-peptide linkers.

| Linker | SEQ ID NO: |
|---|---|
| A | |
| R | |
| N | |
| D | |
| B | |
| C | |
| E | |
| Q | |
| Z | |
| G | |
| H | |
| I | |
| L | |
| K | |
| M | |
| F | |
| P | |
| S | |
| T | |
| W | |
| Y | |
| V | |
| G | |
| AAA | |
| GGG | |
| SGG | |
| SAT | |

TABLE 5-continued

Illustrative peptide and non-peptide linkers.

| Linker | SEQ ID NO: |
|---|---|
| PYP | |
| ASA | |
| GGGG | 17 |
| PSPSP | 18 |
| PSPSP | 19 |
| KKKK | 20 |
| RRRR | 21 |
| ASASA | 22 |
| GGSGGS | 23 |
| GGGGS | 24 |
| GGGGS GGGGS | 25 |
| GGGGS GGGGS GGGGS | 26 |
| GGGGS GGGGS GGGGS GGGGS | 27 |
| GGGGS GGGGS GGGGS GGGGS GGGGS | 28 |
| GGGGS GGGGS GGGGS GGGGS GGGGS GGGGS | 29 |
| 2-nitrobenzene or O-nitrobenzyl | |
| Nitropyridyl disulfide | |
| Dioleoylphosphatidylethanolamine (DOPE) | |
| S-acetylmercaptosuccinic acid | |
| 1,4,7,10-tetraa7acydododecane-1,4,7,10-tetracetic acid (DOTA) | |
| β-glucuronide and β-glucuronide variants | |
| Poly(alkylacrylic acid) | |
| Benzene-based linkers (for example: 2,5-Bis(hexyloxy)-1,4-bis[2,5-bis(hexyloxy)-4-formyl-phenylenevinylene]benzene) and like molecules | |
| Disulfide linkages | |
| Poly(amidoamine) or like dendrimers linking multiple target and killing peptides in one molecule | |
| Hydrazone and hydrazone variant linkers | |
| PEG of any chain length | |
| Succinate, formate, acetate butyrate, other like organic acids | |
| Aldols, alcohols, or enols | |
| Peroxides | |
| alkane or alkene groups of any chain length | |
| Variants of any of the above linkers containing halogen or thiol groups | |
| Quaternary-ammonium-salt linkers | |
| Allyl(4-methoxyphenyl)dimethylsilane | |
| 6-(Allyloxycarbonylamino)-1-hexanol | |
| 3-(Allyloxycarbonylamino)-1-propanol | |
| 4-Aminobutyraldehyde diethyl acetal | |
| (E)-N-(2-Aminoethyl)-4-{2-[4-(3-azidopropoxy)phenyl]diazenyl}benzamide hydrochloride | |
| N-(2-Aminoethyl)maleimide trifluoroacetate | |
| Amino-PEG4-alkyne | |
| Benzyl N-(3-hydroxypropyl)carbamate | |
| 4-(Boc-amino)-1-butanol | |
| 4-(Boc-amino)butyl bromide | |
| 2-(Boc-amino)ethanethiol | |
| 2-[2-(Boc-amino)ethoxy]ethoxyacetic acid (dicyclohexylammonium) salt | |
| 2-(Boc-amino)ethyl bromide | |
| 6-(Boc-amino)-1-hexanol | |
| 21-(Boc-amino)-4,7,10,13,16,19-hexaoxaheneicosanoic acid | |
| 6-(Boc-amino)hexyl bromide | |
| 5-(Boc-amino)-1-pentanol | |
| 3-(Boc-amino)-1-propanol | |
| 3-(Boc-amino)propyl bromide | |
| 15-(Boc-amino)-4,7,10,13-tetraoxapentadecanoic acid | |
| N-Boc-1,4-butanediamine | |
| N-Boc-cadaverine | |
| N-Boc-ethanolamine | |
| N-Boc-ethylenediamine | |
| N-Boc-2,2'-(ethylenedioxy)diethylamine | |
| N-Boc-1,6-hexanediamine | |
| N-Boc-1,6-hexanediamine hydrochloride | |
| N-Boc-4-isothiocyanatoaniline | |
| N-Boc-4-isothiocyanatobutylamine | |
| N-Boc-2-isothiocyanatoethylamine | |
| N-Boc-3-isothiocyanatopropylamine | |
| N-Boc-N-methylethylenediamine | |
| N-Boc-m-phenylenediamine | |
| N-Boc-p-phenylenediamine | |

TABLE 5-continued

Illustrative peptide and non-peptide linkers.

| Linker | SEQ ID NO: |
|---|---|
| 2-(4-Boc-1-piperazinyl)acetic acid | |
| N-Boc-1,3-propanediamine | |
| N-Boc-1,3-propanediamine | |
| N-Boc-N'-succinyl-4,7,10-trioxa-1,13-tridecanediamine | |
| N-Boc-4,7,10-trioxa-1,13-tridecanediamine | |
| N-(4-Bromobutyl)phthalimide | |
| 4-Bromobutyric acid | |
| 4-Bromobutyryl chloride purum | |
| 4-Bromobutyryl chloride | |
| N-(2-Bromoethyl)phthalimide | |
| 6-Bromo-1-hexanol | |
| 3-(Bromomethyl)benzoic acid N-succinimidylester | |
| 4-(Bromomethyl)phenyl isothiocyanate | |
| 8-Bromooctanoic acid | |
| 8-Bromo-1-octanol | |
| 4-(2-Bromopropionyl)phenoxyacetic acid | |
| N-(3-Bromopropyl)phthalimide | |
| 4-(tert-Butoxymethyl)benzoic acid | |
| tert-Butyl 2-(4-{[4-(3-azidopropoxy)phenyl]azo}benzamido)ethylcarbamate | |
| 2-[2-(tert-Butyldimethylsilyloxy)ethoxy]ethanamine | |
| tert-Butyl 4-hydroxybutyrate | |
| 4-(2-Chloropropionyl)phenylacetic acid | |
| 1,11-Diamino-3,6,9-trioxaundecane | |
| di-Boc-cystamine | |
| Diethylene glycol monoallyl ether | |
| 3,4-Dihydro-2H-pyran-2-methanol | |
| 4-[(2,4-Dimethoxyphenyl)(Fmoc-amino)methyl]phenoxyacetic acid | |
| 4-(Diphenylhydroxymethyl)benzoic acid | |
| 4-(Fmoc-amino)-1-butanol | |
| 2-(Fmoc-amino)ethanol | |
| 2-[2-(Fmoc-amino)ethoxy]ethylamine hydrochloride | |
| 2-(Fmoc-amino)ethyl bromide | |
| 6-(Fmoc-amino)-1-hexanol | |
| 5-(Fmoc-amino)-1-pentanol | |
| 3-(Fmoc-amino)-1-propanol | |
| 3-(Fmoc-amino)propyl bromide | |
| N-Fmoc-2-bromoethylamine | |
| N-Fmoc-1,4-butanediamine hydrobromide | |
| N-Fmoc-cadaverine hydrobromide | |
| N-Fmoc-ethylenediamine hydrobromide | |
| N-Fmoc-1,6-hexanediamine hydrobromide | |
| N-Fmoc-1,3-propanediamine hydrobromide | |
| N-Fmoc-N"-succinyl-4,7,10-trioxa-1,13-tridecanediamine | |
| (3-Formyl-1-indolyl)acetic acid | |
| 6-Guanidinohexanoic acid | |
| 4-Hydroxybenzyl alcohol | |
| N-(4-Hydroxybutyl)trifluoroacetamide | |
| 4'-Hydroxy-2,4-dimethoxybenzophenone | |
| N-(2-Hydroxyethyl)maleimide | |
| 4-[4-(1-Hydroxyethyl)-2-methoxy-5-nitrophenoxy]butyric acid | |
| N-(2-Hydroxyethyl)trifluoroacetamide | |
| N-(6-Hydroxyhexyl)trifluoroacetamide | |
| 4-Hydroxy-2-methoxybenzaldehyde | |
| 4-Hydroxy-3-methoxybenzyl alcohol | |
| 4-(Hydroxymethyl)benzoic acid | |
| 4-(4-Hydroxymethyl-3-methoxyphenoxy)butyric acid | |
| 4-(Hydroxymethyl)phenoxyacetic acid | |
| 3-(4-Hydroxymethylphenoxy)propionic acid | |
| N-(5-Hydroxypentyl)trifluoroacetamide | |
| 4-(4'-Hydroxyphenylazo)benzoic acid | |
| N-(3-Hydroxypropyl)trifluoroacetamide | |
| 2-Maleimidoethyl mesylate technical | |
| 4-Mercapto-1-butanol | |
| 6-Mercapto-1-hexanol | |
| Phenacyl 4-(bromomethyl)phenylacetate | |
| 4-Sulfamoylbenzoic acid | |
| N-Trityl-1,2-ethanediamine hydrobromide | |
| 4-(Z-Amino)-1-butanol | |
| 6-(Z-Amino)-1-hexanol | |
| 5-(Z-Amino)-1-pentanol | |
| N-Z-1,4-Butanediamine hydrochloride | |
| N-Z-Ethanolamine | |
| N-Z-Ethylenediamine hydrochloride | |
| N-Z-1,6-hexanediamine hydrochloride | |
| N-Z-1,5-pentanediamine hydrochloride | |
| N-Z-1,3-Propanediamine hydrochloride | |
| 1,4-Bis[3-(2-pyridyldithio)propionamido]butane | |
| BMOE (bis-maleimidoethane) | |
| BM(PEG)2 (1,8-bismaleimido-diethyleneglycol) | |
| BM(PEG)3 (1,11-bismaleimido-triethyleneglycol) | |
| DTME (dithio-bis-maleimidoethane) | |
| BMOE (bis-maleimidoethane) | |
| DTME (dithio-bis-maleimidoethane) | |
| Maleimidoacetic acid N-hydroxysuccinimide ester | |
| 4-(N-Maleimidomethyl)cyclohexanecarboxylic acid N-hydroxysuccinimide ester | |
| 4-(N-Maleimidomethyl)cyclohexane-1-carboxylic acid 3-sulfo-N-hydroxysuccinimide ester | |
| 4-(4-Maleimidophenyl)butyric acid N-hydroxysuccinimide ester | |
| 3-(Maleimido)propionic acid N-hydroxysuccinimide ester | |

(All amino-acid-based linkers could be L, D, combinations of L and D forms, β-form, and the like)

In various embodiments the therapeutic moieties (D) in Formulas IV, V, and VI comprise a polypeptide. Illustrative therapeutic polypeptides include, but are not limited to parathyroide hormone or an analog thereof and/or calcitonin and/or an analog thereof. Analogs of parathyroid hormone are well known to those of skill in the art and include, but are not limited to $PTH_{1-84}$, $PTH_{1-34}$ (teriparatide), and the like.

In certain embodiments the therapeutic moiety "D" comprises an anti-cancer compound and the osteoabsorptive vehicle can be effective to deliver the drug to a cancer (e.g., multiple melanoma). Such anti-cancer agents include, but are not limited to alkylating agents (e.g., mechlorethamine (Mustargen), cyclophosphamide (Cytoxan, Neosar), ifosfamide (Ifex), phenylalanine mustard; melphalen (Alkeran), chlorambucol (Leukeran), uracil mustard, estramustine (Emcyt), thiotepa (Thioplex), busulfan (Myerlan), lomustine (CeeNU), carmustine (BiCNU, BCNU), streptozocin (Zanosar), dacarbazine (DTIC-Dome), cis-platinum, cisplatin (Platinol, Platinol AQ), carboplatin (Paraplatin), altretamine (Hexalen), etc.), antimetabolites (e.g. methotrexate (Amethopterin, Folex, Mexate, Rheumatrex), 5-fluoruracil (Adrucil, Efudex, Fluoroplex), floxuridine, 5-fluorodeoxyuridine (FUDR), capecitabine (Xeloda), fludarabine: (Fludara), cytosine arabinoside (Cytaribine, Cytosar, ARA-C), 6-mercaptopurine (Purinethol), 6-thioguanine (Thioguanine), gemcitabine (Gemzar), cladribine (Leustatin), deoxycoformycin; pentostatin (Nipent), etc.), antibiotics (e.g. doxorubicin (Adriamycin, Rubex, Doxil, Daunoxome-liposomal preparation), daunorubicin (Daunomycin, Cerubidine), idarubicin (Idamycin), valrubicin (Valstar), mitoxantrone (Novantrone), dactinomycin (Actinomycin D, Cosmegen), mithramycin, plicamycin (Mithracin), mitomycin C (Mutamycin), bleomycin (Blenoxane), procarbazine (Matulane), etc.), mitotic inhibitors (e.g. paclitaxel (Taxol), docetaxel (Taxotere), vinblatine sulfate (Velban, Velsar, VLB), vincristine sulfate (Oncovin, Vincasar PFS, Vincrex), vinorelbine sulfate (Navelbine), etc.), chromatin function inhibitors (e.g., topotecan (Camptosar), irinotecan (Hycamtin), etoposide (VP-16, VePesid, Toposar), teniposide (VM-26, Vumon), etc.), hormones and hormone inhibitors (e.g. diethylstilbesterol (Stilbesterol, Stilphostrol), estradiol, estrogen, esterified estrogens (Estratab, Menest), estramustine (Emcyt), tamoxifen (Nolvadex), toremifene (Fareston) anastrozole (Arimidex), letrozole (Femara), 17-OH-progesterone, medroxyprogesterone, megestrol acetate (Megace), goserelin (Zoladex), leuprolide (Leupron), testosteraone, methyltestosterone, fluoxmesterone (Android-F, Halotestin), flutamide (Eulexin), bicalutamide (Casodex), nilutamide (Nilandron), etc.), inhibitors of synthesis (e.g., aminoglutethimide (Cytadren), ketoconazole (Nizoral), etc.), immunomodulators (e.g., RITUXIMAB® (Rituxan), trastuzumab (Herceptin), denileukin diftitox (Ontak), levamisole (Ergamisol), *bacillus* Calmette-Guerin, BCG (TheraCys, TICE BCG), interferon alpha-2a, alpha 2b (Roferon-A, Intron A), interleukin-2, aldesleukin (ProLeukin), etc.) and other agents such as 1-aspariginase (Fispar, Kidrolase), pegaspasgase (Oncaspar), hydroxyurea (Hydrea, Doxia), leucovorin (Welicovorin), mitotane (Lysodren), porfimer (Photofrin), tretinoin (Veasnoid), and the like.

In certain embodiments the therapeutic moiety "D" comprises an antibiotic. Illustrative antibiotics include, but are not limited to those listed in Table 6.

TABLE 6

Illustrative antibiotics for use in the drug delivery vehicles described herein.

| Class | Generic Name | BRAND NAME |
|---|---|---|
| Aminoglycosides | Amikacin | AMIKIN ® |
| | Gentamicin | GARAMYCIN ® |
| | Kanamycin | KANTREX ® |
| | Neomycin | |
| | Netilmicin | NETROMYCIN ® |
| | Streptomycin | |
| | Tobramycin | NEBCIN ® |
| | Paromomycin | HUMATIN ® |
| Carbacephem | | |
| | Loracarbef | LORABID ® |
| Carbapenems | | |
| | Ertapenem | INVANZ ® |
| | Doripenem | FINIBAX ® |
| | Imipenem/ Cilastatin | PRIMAXIN ® |
| | Meropenem | MERREM ® |
| Cephalosporins (First generation) | | |
| | Cefadroxil | DURICEF ® |
| | Cefazolin | ANCEF ® |
| | Cefalotin or Cefalothin | KEFLIN ® |
| | Cefalexin | KEFLEX ® |
| Cephalosporins (Second generation) | | |
| | Cefaclor | CECLOR ® |
| | Cefamandole | MANDOLE ® |
| | Cefoxitin | MEFOXIN ® |
| | Cefprozil | CEFZIL ® |
| | Cefuroxime | CEFTIN, ZINNAT ® |
| Cephalosporins (Third generation) | | |
| | Cefixime | SUPRAX ® |
| | Cefdinir | OMNICEF ® |
| | Cefditoren | SPECTRACEF ® |
| | Cefoperazone | CEFOBID ® |
| | Cefotaxime | CLAFORAN ® |
| | Cefpodoxime | |
| | Ceftazidime | FORTAZ ® |
| | Ceftibuten | CEDAX ® |

TABLE 6-continued

Illustrative antibiotics for use in the drug delivery vehicles described herein.

| Class | Generic Name | BRAND NAME |
|---|---|---|
| | Ceftizoxime | |
| Cephalosporins (Fourth generation) | Ceftriaxone | ROCEPHIN ® |
| Cephalosporins (Fifth generation) | Cefepime | MAXIPIME ® |
| | Ceftobiprole | |
| Glycopeptides | | |
| | Teicoplanin | |
| | Vancomycin | VANCOCIN ® |
| | Dalbavancin | |
| Macrolides | | |
| | Azithromycin | Zithromax |
| | Clarithromycin | Biaxin |
| | Dirithromycin | |
| | Erythromycin | Erythocin, Erythroped |
| | Roxithromycin | |
| | Troleandomycin | |
| | Telithromycin | Ketek |
| Monobactams | | |
| | Aztreonam | |
| Penicillins | | |
| | Amoxicillin | NOVAMOX ®, AMOXIL ® |
| | Ampicillin | |
| | Azlocillin | |
| | Carbenicillin | |
| | Cloxacillin | |
| | Dicloxacillin | |
| | Flucloxacillin | FLOXAPEN ® |
| | Mezlocillin | |
| | Meticillin | |
| | Nafcillin | |
| | Oxacillin | |
| | Penicillin | |
| | Piperacillin | |
| | Ticarcillin | |
| Polypeptides | | |
| | Bacitracin | |
| | Colistin | |
| | Polymyxin B | |
| Quinolones | | |
| | Mafenide | |
| | Prontosil (archaic) | |
| | Sulfacetamide | |
| | Sulfamethizole | |
| | Sulfanilimide (archaic) | |
| | Sulfasalazine | |
| | Sulfisoxazole | |
| | Trimethoprim | BACTRIM ® |
| | Trimethoprim-Sulfamethoxazole (Cotrimoxazole) (TMP-SMX) | |
| Tetracyclines | | |
| | Demeclocycline | |
| | Doxycycline | VIBRAMYCIN ® |
| | Minocycline | MINOCIN ® |
| | Oxytetracycline | TERRACIN ® |
| | Tetracycline | SUMYCIN ® |

TABLE 6-continued

Illustrative antibiotics for use in the drug delivery vehicles described herein.

| Class | Generic Name | BRAND NAME |
|---|---|---|
| Natural products | | |
| | Antimicrobial herbal extracts | |
| | Essential oils | |
| | Farnesol | |
| | Licorice root extracts | |
| | Glycyrrhizol A | |
| | Glycyrrhizol B | |
| | 6,8-diisoprenyl-5,7,4'-trihydroxyiso-flavone | |
| Others | | |
| | Arsphenamine | SALVARSAN ® |
| | Chloramphenicol | CHLOROMYCETIN ® |
| | Clindamycin | CLEOCIN ® |
| | Lincomycin | |
| | Ethambutol | |
| | Fosfomycin | |
| | Fusidic acid | FUCIDIN ® |
| | Furazolidone | |
| | Isoniazid | |
| | Linezolid | ZYVOX ® |
| | Tedizolid | |
| | Metronidazole | FLAGYL ® |
| | Mupirocin | BACTROBAN ® |
| | Nitrofurantoin | MACRODANTIN ® MACROBID ® |
| | Platensimycin | |
| | Pyrazinamide | |
| | Quinupristin/Dalfopristin | SYNCERCID ® |
| | Rifampin or Rifampicin | |
| | Tinidazole | |
| | Artemisinin | |
| | Fidaxomicin | |
| Antifungals | | |
| | Amphotericin B | |
| | Anidulafungin | |
| | Caspofungin acetate | |
| | Clotrimazole | |
| | Fluconazole | |
| | Flucytosine | |
| | Griseofulvin | |
| | Itraconazole | |
| | Ketoconazole | |
| | Micafungin | |
| | Miconazole | |
| | Nystatin | |
| | Pentamidine | |
| | Posaconazole | |
| | Terbinafine | |
| | Voriconazole | |
| Antimycobiotics | | |
| | Aminosalicylic Acid | |
| | Capreomycin | |
| | Clofazimine | |
| | Cycloserine | |
| | Ethionamide | |
| | Rifabutin | |
| | Rifapentine | |
| Antivirals | | |
| | Abacavir | |
| | Acyclovir | |
| | Adefovir | |

TABLE 6-continued

Illustrative antibiotics for use in the drug delivery vehicles described herein.

| Class | Generic Name | BRAND NAME |
|---|---|---|
| | Amantadine | |
| | Atazanavir | |
| | Cidofovir | |
| | Darunavir | |
| | Didanosine | |
| | Docosanol | |
| | Efavirenz | |
| | Emtricitabine | |
| | Enfuvirtide | |
| | Entecavir | |
| | Etravirine | |
| | Famciclovir | |
| | Fomivirsen | |
| | Fosamprenavir | |
| | Foscarnet | |
| | Ganciclovir | |
| | Idoxuridine | |
| | Indinavir | |
| | Interferon alpha | |
| | Lamivudine | |
| | Lopinavir/ritonavir | |
| | Maraviroc | |
| | Nelfinavir | |
| | Nevirapine | |
| | Oseltamivir | |
| | Penciclovir | |
| | Peramivir | |
| | Raltegravir | |
| | Ribavirin | |
| | Rimantadine | |
| | Ritonavir | |
| | Saquinavir | |
| | Stavudine | |
| | Telbivudine | |
| | Tenofovir | |
| | Tipranavir | |
| | Trifluridine | |
| | Valacyclovir | |
| | Valganciclovir | |
| | Zanamivir | |
| | Zidovudine | |
| Anti-parasitics | | |
| | Albendazole | |
| | Artesunate | |
| | Atovaquone | |
| | Bephenium hydroxynaphthoate | |
| | Chloroquine | |
| | Dapsone | |
| | Diethyl-carbamazine | |
| | Diloxanide furoate | |
| | Eflornithine | |
| | Emetine HCl | |
| | Furazolidone | |
| | Ivermectin | |
| | Lindane | |
| | Mebendazole | |
| | Mefloquine | |
| | Melarsoprol | |
| | Miltefosine | |
| | Niclosamide | |
| | Nifurtimox | |
| | Nitazoxanide | |
| | Oxamniquine | |
| | Paromomycin | |
| | Permethrin | |
| | Piperazine | |
| | Praziquantel | |
| | Primaquine | |
| | Pyrantel pamoate | |
| | Pyrimethamine | |
| | Proguanil | |

TABLE 6-continued

Illustrative antibiotics for use in the
drug delivery vehicles described herein.

| Class | Generic Name | BRAND NAME |
|---|---|---|
| | Quinacrine HCl | |
| | Quinidine | |
| | Quinine | |
| | Sodium | |
| | Stibogluconate | |
| | Spiramycin | |
| | Thiabendazole | |
| | Tinidazole | |

The foregoing osteoabsorptive drug delivery vehicles are illustrative and non-limiting. Using the teachings provided herein, numerous alternative vehicles, comprising, for example, different enzyme substrates, different therapeutic moieties, and the like will be available to one of skill in the art.

Pharmaceutical Formulations.

In certain embodiments, the osteoabsorptive fluorogenic probes are administered to a mammal to detect activity of a protease (e.g., cathepsin K) and/or to detect and/or to quantify, and/or to localize the protease activity, and/or to detect and/or quantify, and/or to localize a pathology characterized by bone resorption. Similarly, in certain embodiments the osteoabsorptive drug delivery vehicle are administered to a mammal to deliver/localize a therapeutic moiety to a target site (e.g., to a tissue comprising calcium). In certain embodiments the drug delivery is used to treat a pathology characterized by bone resorption (e.g., hypocalcemia, hypoparathyroidism, osteoporosis, osteoarthritis, rheumatoid arthritis, and certain cancers (e.g., multiple myeloma)).

The osteoabsorptive fluorogenic probes and/or osteoabsorptive drug delivery vehicles described herein can be administered in the "native" form or, if desired, in the form of salts, esters, amides, derivatives, and the like, provided the salt, ester, amide, or derivative is suitable pharmacologically, e.g., effective in the present method(s). Salts, esters, amides, and other derivatives of the osteoabsorptive fluorogenic probes and/or osteoabsorptive drug delivery vehicles can be prepared using standard procedures known to those skilled in the art of synthetic organic chemistry and described, for example, by March (1992) *Advanced Organic Chemistry; Reactions, Mechanisms and Structure,* 4th Ed. N.Y. Wiley-Interscience.

Methods of formulating such derivatives are known to those of skill in the art. For example, a pharmaceutically acceptable salt can be prepared for any compound described herein having a functionality capable of forming a salt (e.g., such as a carboxylic acid functionality of the compounds described herein). A pharmaceutically acceptable salt is any salt that retains the activity of the parent compound and does not impart any deleterious or untoward effect on the subject to which it is administered and in the context in which it is administered.

Methods of pharmaceutically formulating the compounds described herein as salts, esters, amides, and the like are well known to those of skill in the art. For example, salts can be prepared from the free base using conventional methodology that typically involves reaction with a suitable acid. Generally, the base form of the drug is dissolved in a polar organic solvent such as methanol or ethanol and the acid is added thereto. The resulting salt either precipitates or can be brought out of solution by addition of a less polar solvent.

Suitable acids for preparing acid addition salts include, but are not limited to both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt can be reconverted to the free base by treatment with a suitable base. Certain particularly preferred acid addition salts of the compounds described herein can include halide salts, such as may be prepared using hydrochloric or hydrobromic acids. Conversely, preparation of basic salts of the osteoabsorptive fluorogenic probes and/or osteoabsorptive drug delivery vehicles described herein can be prepared in a similar manner using a pharmaceutically acceptable base such as sodium hydroxide, potassium hydroxide, ammonium hydroxide, calcium hydroxide, trimethylamine, or the like. In certain embodiments basic salts include alkali metal salts, e.g., the sodium salt, and copper salts.

For the preparation of salt forms of basic drugs, the pKa of the counterion is preferably at least about 2 pH units lower than the pKa of the drug. Similarly, for the preparation of salt forms of acidic drugs, the pKa of the counterion is preferably at least about 2 pH units higher than the pKa of the drug. This permits the counterion to bring the solution's pH to a level lower than the $pH_{max}$ to reach the salt plateau, at which the solubility of salt prevails over the solubility of free acid or base. The generalized rule of difference in pKa units of the ionizable group in the active pharmaceutical ingredient (API) and in the acid or base is meant to make the proton transfer energetically favorable. When the pKa of the API and counterion are not significantly different, a solid complex may form but may rapidly disproportionate (e.g., break down into the individual entities of drug and counterion) in an aqueous environment.

In various embodiments, the counterion is a pharmaceutically acceptable counterion. Suitable anionic salt forms include, but are not limited to acetate, benzoate, benzylate, bitartrate, bromide, carbonate, chloride, citrate, edetate, edisylate, estolate, formate, fumarate, gluceptate, gluconate, hydrobromide, hydrochloride, iodide, lactate, lactobionate, malate, maleate, mandelate, mesylate, methyl bromide, methyl sulfate, mucate, napsylate, nitrate, pamoate (embonate), phosphate and diphosphate, salicylate and disalicylate, stearate, succinate, sulfate, tartrate, tosylate, triethiodide, valerate, and the like, while suitable cationic salt forms include, but are not limited to aluminum, benzathine, calcium, ethylene diamine, lysine, magnesium, meglumine, potassium, procaine, sodium, tromethamine, zinc, and the like.

Preparation of esters typically involves functionalization of hydroxyl and/or carboxyl groups that are present within the molecular structure of the active agent (e.g., osteoabsorptive fluorogenic probes and/or osteoabsorptive drug delivery vehicles). In certain embodiments, the esters are typically acyl-substituted derivatives of free alcohol groups, e.g., moieties that are derived from carboxylic acids of the formula RCOOH where R is alky, and preferably is lower alkyl. Esters can be reconverted to the free acids, if desired, by using conventional hydrogenolysis or hydrolysis procedures.

Amides can also be prepared using techniques known to those skilled in the art or described in the pertinent literature. For example, amides may be prepared from esters, using suitable amine reactants, or they may be prepared from an anhydride or an acid chloride by reaction with ammonia or a lower alkyl amine.

In various embodiments, the compounds identified herein are useful for parenteral, topical, oral, nasal (or otherwise inhaled), rectal, or local administration, such as by aerosol or transdermally, for prophylactic and/or therapeutic treatment of one or more of the pathologies/indications described herein (e.g., amyloidogenic pathologies).

The active agent(s) described herein (e.g., osteoabsorptive fluorogenic probes and/or osteoabsorptive drug delivery vehicles) can also be combined with a pharmaceutically acceptable carrier (excipient) to form a pharmacological composition. Pharmaceutically acceptable carriers can contain one or more physiologically acceptable compound(s) that act, for example, to stabilize the composition or to increase or decrease the absorption of the osteoabsorptive fluorogenic probes and/or osteoabsorptive drug delivery vehicles. Physiologically acceptable compounds can include, for example, carbohydrates, such as glucose, sucrose, or dextrans, antioxidants, such as ascorbic acid or glutathione, chelating agents, low molecular weight proteins, protection and uptake enhancers such as lipids, compositions that reduce the clearance or hydrolysis of the osteoabsorptive fluorogenic probes and/or osteoabsorptive drug delivery vehicles, or excipients or other stabilizers and/or buffers.

Other physiologically acceptable compounds, particularly of use in the preparation of tablets, capsules, gel caps, and the like include, but are not limited to binders, diluent/fillers, disentegrants, lubricants, suspending agents, and the like.

In certain embodiments, to manufacture an oral dosage form (e.g., a tablet), an excipient (e.g., lactose, sucrose, starch, mannitol, etc.), an optional disintegrator (e.g., calcium carbonate, carboxymethylcellulose calcium, sodium starch glycollate, crospovidone etc.), a binder (e.g., alphastarch, gum arabic, microcrystalline cellulose, carboxymethylcellulose, polyvinylpyrrolidone, hydroxypropylcellulose, cyclodextrin, etc.), and an optional lubricant (e.g., talc, magnesium stearate, polyethylene glycol 6000, etc.), for instance, are added to the active component or components (e.g., osteoabsorptive fluorogenic probes and/or osteoabsorptive drug delivery vehicles) and the resulting composition is compressed. Where necessary the compressed product is coated, e.g., known methods for masking the taste or for enteric dissolution or sustained release. Suitable coating materials include, but are not limited to ethyl-cellulose, hydroxymethylcellulose, polyoxyethylene glycol, cellulose acetate phthalate, hydroxypropylmethylcellulose phthalate, and Eudragit (Rohm & Haas, Germany; methacrylic-acrylic copolymer).

Other physiologically acceptable compounds include wetting agents, emulsifying agents, dispersing agents or preservatives that are particularly useful for preventing the growth or action of microorganisms. Various preservatives are well known and include, for example, phenol and ascorbic acid. One skilled in the art would appreciate that the choice of pharmaceutically acceptable carrier(s), including a physiologically acceptable compound depends, for example, on the route of administration of the osteoabsorptive fluorogenic probes and/or osteoabsorptive drug delivery vehicles described herein and on the particular physio-chemical characteristics of the osteoabsorptive fluorogenic probes and/or osteoabsorptive drug delivery vehicles.

In certain embodiments, the excipients are sterile and generally free of undesirable matter. These compositions can be sterilized by conventional, well-known sterilization techniques. For various oral dosage form excipients such as tablets and capsules sterility is not required. The USP/NF standard is usually sufficient.

The pharmaceutical compositions can be administered in a variety of unit dosage forms depending upon the method of administration. Suitable unit dosage forms, include, but are not limited to powders, tablets, pills, capsules, lozenges, suppositories, patches, nasal sprays, injectable, implantable sustained-release formulations, mucoadherent films, topical varnishes, lipid complexes, etc.

Pharmaceutical compositions comprising the osteoabsorptive fluorogenic probes and/or osteoabsorptive drug delivery vehicles described herein can be manufactured by means of conventional mixing, dissolving, granulating, dragee-making, levigating, emulsifying, encapsulating, entrapping or lyophilizing processes. Pharmaceutical compositions can be formulated in a conventional manner using one or more physiologically acceptable carriers, diluents, excipients or auxiliaries that facilitate processing of the osteoabsorptive fluorogenic probes and/or osteoabsorptive drug delivery vehicles into preparations that can be used pharmaceutically. Proper formulation is dependent upon the route of administration chosen.

Systemic formulations include, but are not limited to, those designed for administration by injection, e.g., subcutaneous, intravenous, intramuscular, intrathecal or intraperitoneal injection, as well as those designed for transdermal, transmucosal oral or pulmonary administration. For injection, the osteoabsorptive fluorogenic probes and/or osteoabsorptive drug delivery vehicles described herein can be formulated in aqueous solutions, preferably in physiologically compatible buffers such as Hanks solution, Ringer's solution, or physiological saline buffer and/or in certain emulsion formulations. The solution can contain formulatory agents such as suspending, stabilizing and/or dispersing agents. In certain embodiments, the osteoabsorptive fluorogenic probes and/or osteoabsorptive drug delivery vehicles can be provided in powder form for constitution with a suitable vehicle, e.g., sterile pyrogen-free water, before use. For transmucosal administration, penetrants appropriate to the barrier to be permeated can be used in the formulation. Such penetrants are generally known in the art.

For oral administration, the compounds can be readily formulated by combining the osteoabsorptive fluorogenic probes and/or osteoabsorptive drug delivery vehicles with pharmaceutically acceptable carriers well known in the art. Such carriers enable the compounds described herein to be formulated as tablets, pills, dragees, capsules, liquids, gels, syrups, slurries, suspensions and the like, for oral ingestion by a patient to be treated. For oral solid formulations such as, for example, powders, capsules and tablets, suitable excipients include fillers such as sugars, such as lactose, sucrose, mannitol and sorbitol; cellulose preparations such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP); granulating agents; and binding agents. If desired, disintegrating agents may be added, such as the cross-linked polyvinylpyrrolidone, agar, or alginic acid or a salt thereof such as sodium alginate. If desired, solid dosage forms may be sugar-coated or enteric-coated using standard techniques.

For oral liquid preparations such as, for example, suspensions, elixirs and solutions, suitable carriers, excipients or diluents include water, glycols, oils, alcohols, etc. Additionally, flavoring agents, preservatives, coloring agents and the like can be added. For buccal administration, the compositions may take the form of tablets, lozenges, etc. formulated in conventional manner.

For administration by inhalation, the osteoabsorptive fluorogenic probes and/or osteoabsorptive drug delivery vehicles described herein are conveniently delivered in the form of an aerosol spray from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

In various embodiments, the osteoabsorptive fluorogenic probes and/or osteoabsorptive drug delivery vehicles described herein can be formulated in rectal or vaginal compositions such as suppositories or retention enemas, e.g., containing conventional suppository bases such as cocoa butter or other glycerides.

In addition to the formulations described previously, the osteoabsorptive fluorogenic probes and/or osteoabsorptive drug delivery vehicles may also be formulated as a depot preparation. Such long acting formulations can be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Alternatively, other pharmaceutical delivery systems can be employed. Liposomes and emulsions are well known examples of delivery vehicles that may be used to protect and deliver pharmaceutically active compounds. Certain organic solvents such as dimethylsulfoxide also can be employed, although usually at the cost of greater toxicity. Additionally, the compounds may be delivered using a sustained-release system, such as semipermeable matrices of solid polymers containing the therapeutic agent. Various uses of sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

In certain embodiments, the osteoabsorptive fluorogenic probes and/or osteoabsorptive drug delivery vehicles and/or formulations described herein are administered orally. This is readily accomplished by the use of tablets, caplets, lozenges, liquids, and the like.

In certain embodiments, the osteoabsorptive fluorogenic probes and/or osteoabsorptive drug delivery vehicles and/or formulations described herein are administered systemically (e.g., orally, or as an injectable) in accordance with standard methods well known to those of skill in the art. In other embodiments, the agents can also be delivered through the skin using conventional transdermal drug delivery systems, e.g., transdermal "patches" wherein the compound(s) and/or formulations described herein are typically contained within a laminated structure that serves as a drug delivery device to be affixed to the skin. In such a structure, the drug composition is typically contained in a layer, or "reservoir," underlying an upper backing layer. It will be appreciated that the term "reservoir" in this context refers to a quantity of "active ingredient(s)" that is ultimately available for delivery to the surface of the skin. Thus, for example, the "reservoir" may include the active ingredient(s) in an adhesive on a backing layer of the patch, or in any of a variety of different matrix formulations known to those of skill in the art. The patch may contain a single reservoir, or it may contain multiple reservoirs.

In one illustrative embodiment, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are present as separate and distinct layers, with the adhesive underlying the reservoir which, in this case, may be either a polymeric matrix as described above, or it may be a liquid or hydrogel reservoir, or may take some other form. The backing layer in these laminates, which serves as the upper surface of the device, preferably functions as a primary structural element of the "patch" and provides the device with much of its flexibility. The material selected for the backing layer is preferably substantially impermeable to the osteoabsorptive fluorogenic probes and/or osteoabsorptive drug delivery vehicles and any other materials that are present.

In certain embodiments, one or more osteoabsorptive fluorogenic probes and/or osteoabsorptive drug delivery vehicles described herein can be provided as a "concentrate", e.g., in a storage container (e.g., in a premeasured volume) ready for dilution, or in a soluble capsule ready for addition to a volume of water, alcohol, hydrogen peroxide, or other diluent.

In certain embodiments, the osteoabsorptive fluorogenic probes and/or osteoabsorptive drug delivery vehicles described herein are suitable for oral administration. In various embodiments, the compound(s) in the oral compositions can be either coated or non-coated. The preparation of enteric-coated particles is disclosed for example in U.S. Pat. Nos. 4,786,505 and 4,853,230.

In various embodiments, compositions contemplated herein typically comprise one or more of the various osteoabsorptive fluorogenic probes and/or osteoabsorptive drug delivery vehicles described herein in an effective amount to achieve a pharmacological effect or therapeutic improvement without undue adverse side effects. Illustrative pharmacological effects or therapeutic improvements include, but are not limited to a reduction or cessation in the rate of bone resorption at one or more locations, an increase in bone density, a reduction in tumor volume, a reduction in arthritic pathology, and the like.

In various embodiments, the typical daily dose of osteoabsorptive fluorogenic probes and/or osteoabsorptive drug delivery vehicles varies and will depend on various factors such as the individual requirements of the patients and the disease to be diagnosed and/or treated. In general, the daily dose of compounds can be in the range of 1-1,000 mg or 1-800 mg, or 1-600 mg, or 1-500 mg, or 1-400 mg. In one illustrative embodiment a standard approximate amount of the osteoabsorptive fluorogenic probes and/or osteoabsorptive drug delivery vehicles described above present in the composition can be typically about 1 to 1,000 mg, more preferably about 5 to 500 mg, and most preferably about 10 to 100 mg. In certain embodiments the probes are administered only once, or for follow-up as required. In certain embodiments the osteoabsorptive drug delivery vehicles are administered once a day, in certain embodiments, administered twice a day, in certain embodiments, administered 3 times/day, and in certain embodiments, administered 4, or 6, or 6 or 7, or 8 times/day.

In certain embodiments the active ingredients (osteoabsorptive fluorogenic probes and/or osteoabsorptive drug delivery vehicles) are formulated in a single oral dosage form containing all active ingredients. Such oral formulations include solid and liquid forms. It is noted that solid formulations typically provide improved stability as compared to liquid formulations and can often afford better patient compliance.

In one illustrative embodiment, the one or more of the osteoabsorptive fluorogenic probes and/or osteoabsorptive drug delivery vehicles described herein are formulated in a single solid dosage form such as single- or multi-layered tablets, suspension tablets, effervescent tablets, powder, pellets, granules or capsules comprising multiple beads as well as a capsule within a capsule or a double chambered capsule. In another embodiment, the osteoabsorptive fluorogenic probes and/or osteoabsorptive drug delivery vehicles described herein may be formulated in a single liquid dosage form such as suspension containing all active ingredients or dry suspension to be reconstituted prior to use.

In certain embodiments, the osteoabsorptive fluorogenic probes and/or osteoabsorptive drug delivery vehicles are formulated as enteric-coated delayed-release granules or as granules coated with non-enteric time-dependent release polymers in order to avoid contact with the gastric juice. Non-limiting examples of suitable pH-dependent enteric-coated polymers are: cellulose acetate phthalate, hydroxypropylmethylcellulose phthalate, polyvinylacetate phthalate, methacrylic acid copolymer, shellac, hydroxypropylmethylcellulose succinate, cellulose acetate trimellitate, and mixtures of any of the foregoing. A suitable commercially available enteric material, for example, is sold under the trademark EUDRAGIT L 100-55®. This coating can be spray coated onto a substrate.

Illustrative non-enteric-coated time-dependent release polymers include, for example, one or more polymers that swell in the stomach via the absorption of water from the gastric fluid, thereby increasing the size of the particles to create thick coating layer. The time-dependent release coating generally possesses erosion and/or diffusion properties that are independent of the pH of the external aqueous medium. Thus, the active ingredient is slowly released from the particles by diffusion or following slow erosion of the particles in the stomach.

Illustrative non-enteric time-dependent release coatings are for example: film-forming compounds such as cellulosic derivatives, such as methylcellulose, hydroxypropyl methylcellulose (HPMC), hydroxyethylcellulose, and/or acrylic polymers including the non-enteric forms of the EUDRAGIT® brand polymers. Other film-forming materials can be used alone or in combination with each other or with the ones listed above. These other film forming materials generally include, for example, poly(vinylpyrrolidone), Zein, poly(ethylene glycol), poly(ethylene oxide), poly(vinyl alcohol), poly(vinyl acetate), and ethyl cellulose, as well as other pharmaceutically acceptable hydrophilic and hydrophobic film-forming materials. These film-forming materials may be applied to the substrate cores using water as the vehicle or, alternatively, a solvent system. Hydro-alcoholic systems may also be employed to serve as a vehicle for film formation.

Other materials suitable for making the time-dependent release coating of the compounds described herein include, by way of example and without limitation, water soluble polysaccharide gums such as carrageenan, fucoidan, gum ghatti, tragacanth, arabinogalactan, pectin, and xanthan; water-soluble salts of polysaccharide gums such as sodium alginate, sodium tragacanthin, and sodium gum ghattate; water-soluble hydroxyalkylcellulose wherein the alkyl member is straight or branched of 1 to 7 carbons such as hydroxymethylcellulose, hydroxyethylcellulose, and hydroxypropylcellulose; synthetic water-soluble cellulose-based lamina formers such as methyl cellulose and its hydroxyalkyl methylcellulose cellulose derivatives such as a member selected from the group consisting of hydroxyethyl methylcellulose, hydroxypropyl methylcellulose, and hydroxybutyl methylcellulose; other cellulose polymers such as sodium carboxymethylcellulose; and other materials known to those of ordinary skill in the art. Other lamina forming materials that can be used for this purpose include, but are not limited to poly(vinylpyrrolidone), polyvinylalcohol, polyethylene oxide, a blend of gelatin and polyvinylpyrrolidone, gelatin, glucose, saccharides, povidone, copovidone, poly(vinylpyrrolidone)-poly(vinyl acetate) copolymer.

While the osteoabsorptive fluorogenic probes and/or osteoabsorptive drug delivery vehicles and methods of use thereof are described herein with respect to use in humans, they are also suitable for animal, e.g., veterinary use. Thus certain illustrative organisms include, but are not limited to humans, non-human primates, canines, equines, felines, porcines, ungulates, largomorphs, and the like.

The foregoing formulations and administration methods are intended to be illustrative and not limiting. It will be appreciated that, using the teaching provided herein, other suitable formulations and modes of administration can be readily devised.

Kits.

In various embodiments the agents described herein (osteoabsorptive fluorogenic probes and/or osteoabsorptive drug delivery vehicles) can be provided in kits. In certain embodiments the kits comprise the osteoabsorptive fluorogenic probes and/or osteoabsorptive drug delivery vehicles described herein enclosed in multiple or single dose containers. In certain embodiments the kits can comprises component parts that can be assembled for use. For example, an osteoabsorptive fluorogenic probe and/or osteoabsorptive drug delivery vehicle in lyophilized form and a suitable diluent may be provided as separated components for combination prior to use. In certain embodiments a kit may include an active osteoabsorptive fluorogenic probes and/or osteoabsorptive drug delivery vehicles and a second therapeutic agent for co-administration. The active agent and second therapeutic agent may be provided as separate component parts. A kit may include a plurality of containers, each container holding one or more unit dose of the osteoabsorptive fluorogenic probes and/or osteoabsorptive drug delivery vehicles. The containers are preferably adapted for the desired mode of administration, including, but not limited to tablets, gel capsules, sustained-release capsules, and the like for oral administration; depot products, pre-filled syringes, ampules, vials, and the like for parenteral administration; and patches, medipads, creams, and the like for topical administration, e.g., as described herein.

In certain embodiments the kits can further comprise instructional/informational materials. In certain embodiments the informational material(s) indicate that the administering of the compositions can result in adverse reactions including but not limited to allergic reactions such as, for example, anaphylaxis. The informational material can indicate that allergic reactions may exhibit only as mild pruritic rashes or may be severe and include erythroderma, vasculitis, anaphylaxis, Steven-Johnson syndrome, and the like. In certain embodiments the informational material(s) may indicate that anaphylaxis can be fatal and may occur when any foreign substance is introduced into the body. In certain embodiments the informational material may indicate that these allergic reactions can manifest themselves as urticaria or a rash and develop into lethal systemic reactions and can occur soon after exposure such as, for example, within 10 minutes. The informational material can further indicate that an allergic reaction may cause a subject to experience paresthesia, hypotension, laryngeal edema, mental status changes, facial or pharyngeal angioedema, airway obstruction, bronchospasm, urticaria and pruritus, serum sickness, arthritis, allergic nephritis, glomerulonephritis, temporal arthritis, eosinophilia, or a combination thereof.

While the instructional materials typically comprise written or printed materials they are not limited to such. Any medium capable of storing such instructions and communicating them to an end user is contemplated herein. Such media include, but are not limited to electronic storage media (e.g., magnetic discs, tapes, cartridges, chips), optical media (e.g., CD ROM), and the like. Such media may include addresses to internet sites that provide such instructional materials.

In some embodiments, the kits can comprise one or more packaging materials such as, for example, a box, bottle, tube, vial, container, sprayer, insufflator, intravenous (IV.) bag, envelope, and the like, and at least one unit dosage form of an agent comprising active agent(s) described herein and a packaging material. In some embodiments, the kits also include instructions for using the composition as prophylactic, therapeutic, or ameliorative treatment for the disease of concern.

EXAMPLES

The following examples are offered to illustrate, but not to limit the claimed invention.

Example 1

Synthesis and Characterization of an Osteoadsorptive Fluorogenic Substrate of Cathepsin K In this example, we describe the synthesis and application of a bone-targeted fluorescent probe (OFS-1) activated by the protease enzyme cathepsin K. The probe employs the internally quenched fluorescence (IQF) strategy and is a fluorogenic substrate of cathepsin K with $K_{cat}=0.2\pm0.03$ s$^{-1}$ and $K_m=1.7\pm0.2$ μM in solution at 37° C., pH 5.5. Bone targeting is accomplished by functionalization with an α-hydroxy bisphosphonate group and the compound is found to adsorb on calcium phosphate substrates. The combination of strong bone binding and protease sensitivity makes these molecules useful as sentinel probes that remain in place and respond when activated by cathepsin K. OFS-1 has been shown to give a fluorescent signal in response to resorptive activity of monocyte-derived human osteoclasts in culture on calcium phosphate coated microwells. Resorbing cells are fluorescently labeled by cleavage and uptake of the probe. The substrate under the cell is labeled as well and increased fluorescence persists after the osteoclast migrates giving a convenient way to track their migration. Preliminary experiments in young mice show increased fluorescent signal in maxilla ex vivo in around the site of a tooth extraction. Fluorescent control probe without quencher gave even labeling of the entire maxilla. OFS-1 is a promising new imaging reagent for the study of cathepsin k, osteoclasts, and their role in various disease process.

Also reported herein is the synthetic route to a second, far-red emitting probe that is believed to be even more effective for in vivo studies due to the greater tissue penetration depth of NIR light and the reduced tissue autofluorescence at these wavelengths compared to visible light. Additionally, effects due to the pH sensitivity of the fluorophore are believed to be greatly reduced by using cyanine based NIR dyes that have little pH sensitivity.

The use of bisphosphonate targeting for drug delivery to osteoclastic resorption sites and activation by proteases is also described. Additionally, application to imaging (detection of) early bone disease, including multiple myeloma, is disclosed.

Figure 8:
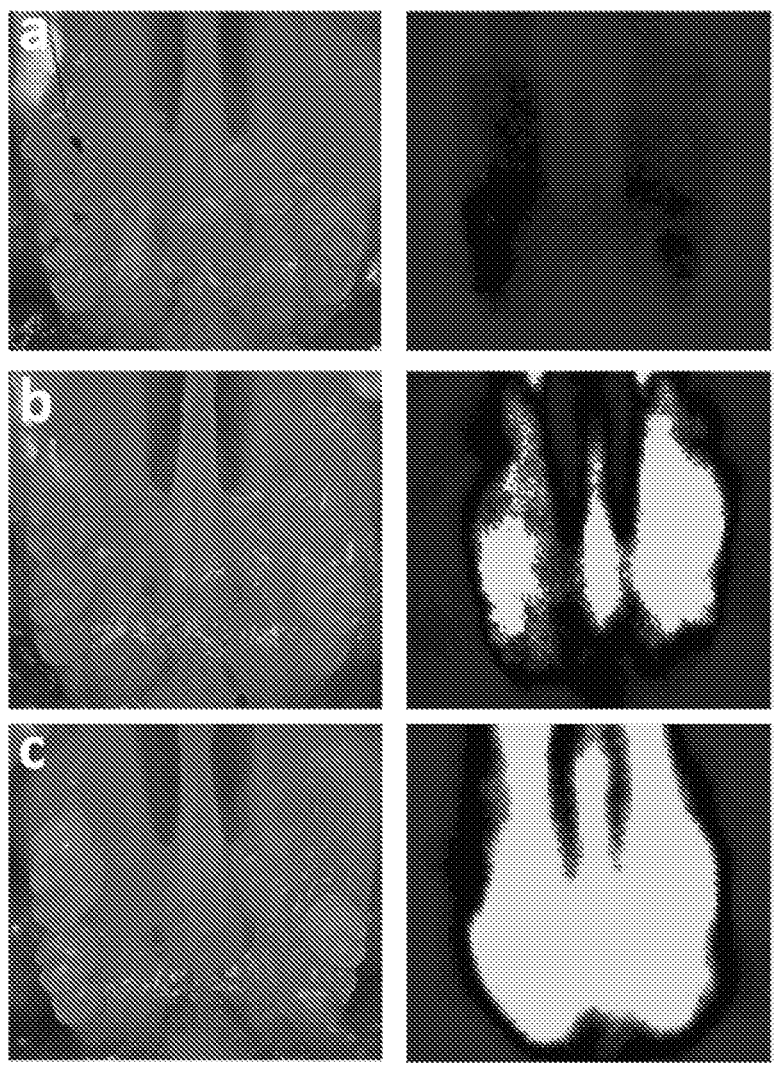
FIG. 8, panels a-c, show White light (left) and fluorescence (right) images of mice after tooth extraction. Panel a) Vehicle control; Panel b) OFS-1 (5a) 5 nMol/mouse; Panel c) Positive control (4a) 5 nMol/mouse FIG. 9, panels a-c, illustrates OFS-1 activation by multiple myeloma in humanized mice. 8226-LUC human multiple myeloma cells were injected to humanized BLT mice. Engrafting of 8226-LUC cells were confirmed by the luciferase activity Panel A) OFS-1 activity was detected by fluorescent signal, which was localized at the multiple myeloma (8226-LUC) engrafted site (panel B). MicroCT analysis indicated that OFS-1 signal was in the relatively early multiple myeloma lesion without detrimental osteolysis.
Figure 9:
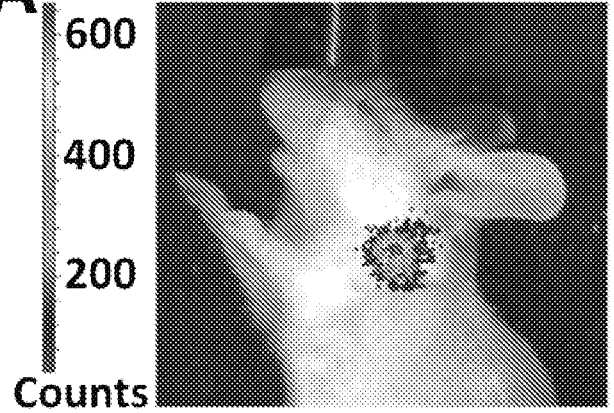
Figure 9:
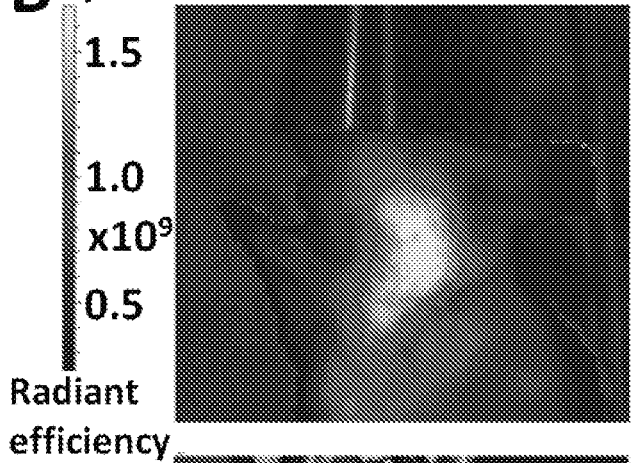
Figure 9:
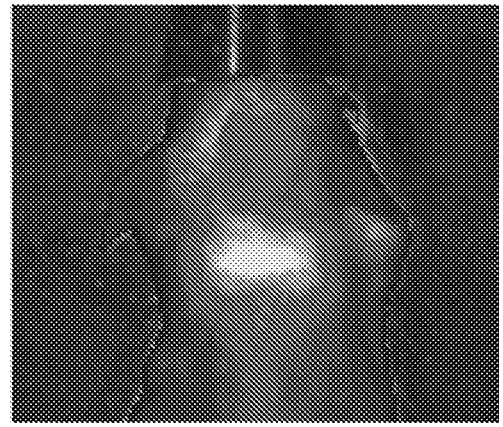
Figure 9:
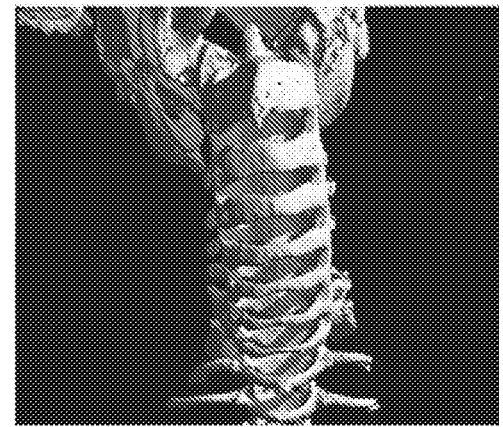

In particular, herein we report the first bone-targeted protease sensor. The compound employs the bisphosphonate compound pamidronate as the targeting moiety and 5-carboxyfluorescein (5-FAM) and Black Hole Quencher-1 (BHQ-1) as the fluorophore-quencher pair. The linker incorporates the known cathepsin k-selective sequence HPGGPQ (Lecaille et al. (2003) *Biochem. J.* 375:307-312). The compound has been shown persist on a calcium phosphate surface after washing and to be cleavable by cathepsin k both in solution and adsorbed. It is useful as a sentinel probe for bone resorption, remaining adsorbed on bone and giving a persistent record of osteoclast activity and migration on a calcium phosphate surface and showing a response to increased resorptive activity in mice caused by tooth extraction. (FIG. 8).

Materials and Methods

Figure 7:
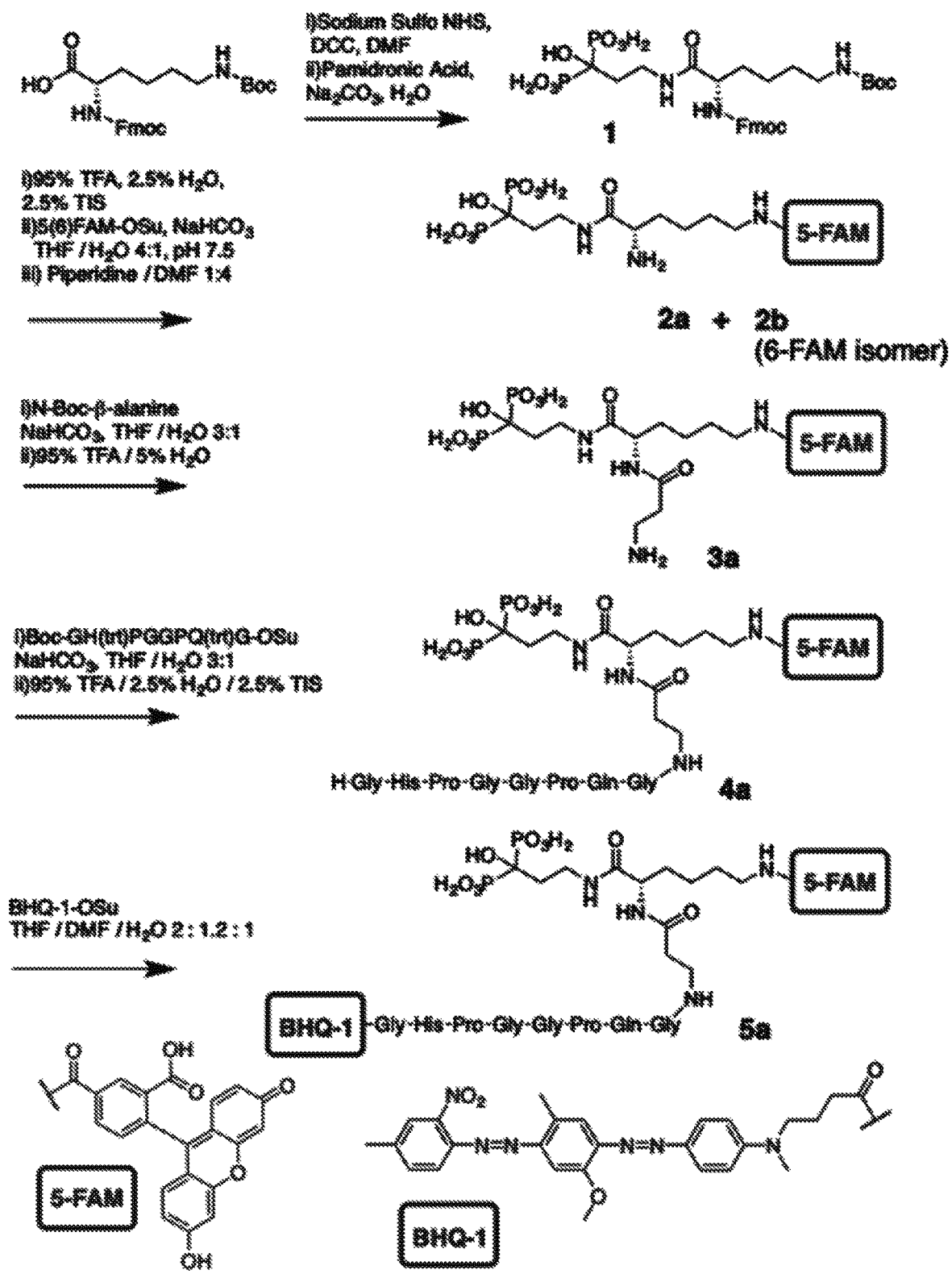
FIG. 7 illustrates Scheme 1: Synthesis of OFS-1.

Synthesis Carboxyfluorescein Probe (see, Scheme 1, FIG. 7).

Synthesis scheme 1 for a carboxyfluoresceine probe is shown in FIG. 7 which illustrates the structures of the compounds referenced below.

3-($N_α$-Fmoc-$N_ε$-Boc-(L)-lysineamido)-1-hydroxy-propane-1,1-diyl)bis(phosphonic acid) (1)

$N_α$-Fmoc-$N_ε$-Boc-(L)-lysine (117.2 mg, 0.25 mmol) was dissolved in DMF (625 μl). N-hydroxysulfosuccinimide sodium salt (65.3 mg, 0.3 mmol) was added and the mixture sonicated to give a white suspension. Dicyclohexycarbodiimide (51.6 mg, 0.25 mmol) was added and the mixture was stirred for 2 h. Reaction was monitored by TLC (100% ethyl acetate, visualized with short wave UV) starting material spot at RF 0.2-0.5 is diminished and product at RF=0 is major spot. Mass spectrometry (ESI, negative mode) showed major peak corresponding to activated ester (Predicted: 644.2 found: 644.7). Reaction mix was centrifuged and the supernatant was collected and added at room temperature to a 0.3 M solution of the sodium salt of (3-amino-1-hydroxypropane-1,1-diyl)bis(phosphonic acid) (Pamidronic acid) adjusted to pH to 7.5 with $Na_2CO_3$. Gas was evolved and white precipitate formed after several minutes. Solid was separated from the supernatant by centrifugation, then 140 μl of acetic acid was added causing a white precipitate to form. The precipitate was collected by centrifugation and washed with water (2 ml) and EtOAc (2×2 ml). Solid was dried in vacuum and a mixture of TFA, water, and triisopropylsilane (95:2.5:2.5) was and stirred for 3 h at room temperature. Solvents were removed and residue was used without further purification. $^1$H NMR (400 MHz, Deuterium Oxide) δ 7.84-7.66 (m, 2H), 7.66-7.43 (m, 2H), 7.43-7.14 (m, 4H), 4.71-4.46 (m, 3H), 4.45-4.26 (m, 1H), 4.13 (s, 1H), 3.90-3.67 (m, 1H), 3.47-3.11 (m, 2H), 2.81 (t, J=7.7 Hz, 2H), 2.11-1.78 (m, 2H), 1.63-1.30 (m, 2H), 1.19-0.85 (m, 2H). $^{31}$P NMR (162 MHz, Deuterium Oxide) δ 17.81. MS (ESI−) m/z: 585.3 [M−H]$^-$ calc. for $C_{24}H_{32}N_3O_{10}P_2^-$: 584.2

(S)-5-((5-amino-6-((3-hydroxy-3,3-diphosphonopropyl)amino)-6-oxohexyl)carbamoyl)-2-(6-hydroxy-3-oxo-3H-xanthen-9-yl)benzoic acid (2a) and (S)-4-((5-amino-6-((3-hydroxy-3,3-diphosphonopropyl)amino)-6-oxohexyl)carbamoyl)-2-(6-hydroxy-3-oxo-3H-xanthen-9-yl)benzoic acid (2b)

Compound 1 (10 mg, 17.1 µmol) was suspended in water (0.45 ml) and THF (0.34 ml). 5(6) Carboxyfluorescein succinimidyl ester (12.1 mg, 25.6 µmol) dissolved in 0.90 ml of THF was added. Reaction mix was stirred overnight and then solvents were removed in vacuum and the crude material was suspended in DMF (0.8 ml) and treated with piperidine (0.2 ml) and stirred for 2 h at room temperature. ESI Mass spec. showed appearance of a new peak at m/z=720.2. Solvent was removed and the residue was dissolved in water (20 ml) and 100 µl of acetic acid was added and the aqueous phase was extracted with ethyl acetate (3×20 ml). Aqueous phase was evaporated in vacuum and 2 ml of water was added giving an orange suspension. pH was adjusted to 7.5 with triethylamine to dissolve solids. Compound was purified by HPLC (10×250 mm Phenomenix Luna Cis column) using 0.1M tetramethylammonium bicarbonate buffers containing 10% and 70% methanol (A and B respectively). The gradient giving the best separation and speed was as follows: 0-1 min, 100% A; 1-3 min, 0-20% B; 3-6 min, 20% B; 6-14 min, 20-100% B. Peak retention times for the two isomers were 8.7 and 12 min. Isomers were collected separately and then coevaporated twice with water to remove buffer salts. Amounts of each isomer were determined by UV absorbance (PBS Buffer, pH 7.4, ε=73,000 at 493 nm assumed) Yield: 5-FAM isomer (2a): 4.96 µmol, 6-FAM isomer (2b): 1.95 µmol. (41% combined yield). MS (ESI−) m/z: 5 isomer: 720.3 [M−H]$^-$ 6 isomer: 720.4 [M−H]$^-$ calc. for $C_{30}H_{32}N_3O_{14}P_2^-$: 720.1

(S)-4-((5-(3-aminopropanamido)-6-((3-hydroxy-3,3-diphosphonopropyl)amino)-6-oxohexyl)carbamoyl)-2-(6-hydroxy-3-oxo-3H-xanthen-9-yl)benzoic acid (3a)

14 µl of water was added to compound 2a (4.96 µmol) giving an orange solution. 34 µl of THF was added. Compound was still soluble. 9.2 µl of saturated sodium bicarbonate solution was added. N-Boc-β-alanine succinimidyl ester solution in THF (0.3 M, 33.6 µl, 10.1 µmol) was added. The reaction mixture was two phases after addition. Mixture was stirred vigorously overnight in a sealed 1 ml vial. Reaction mixture was checked by mass spectrometry, starting material was not found, peak for product was detected: MS (ESI−) m/z: 891 [M−H]$^-$ calc. for $C_{38}H_{45}N_4O_{17}P_2^-$: 891.2. Solvents were evaporated in vacuum. 10 µl of water then 200 µl of TFA was added giving a clear light yellow-green solution. Vial was shaken and left for 1 hr. Reaction was checked by mass spec. Starting material was not detected. Solvents were removed and residue was dissolved in 400 µl of 0.1M triethylammonium bicarbonate (TEAB) buffer with 10% MeOH by addition of 8 µl of neat Et$_3$N giving an orange solution for HPLC injection. Compound was purified by reverse-phase HPLC (10×250 mm Phenomenix Luna Cis column) using 0.1M TEAB pH 7.5 buffers containing 10% and 70% methanol (A and B respectively). Gradient was as follows: 0-1 min, 100% A; 1-11 min, 0-100% B. Target eluted with a retention time of 8 min. Product fractions were evaporated then coevaporated twice with water to remove buffer salts. Amount was determined by UV absorbance (PBS Buffer, pH 7.4, ε=73,000 at 493 nm assumed). Yield: 3.23 µmol, 65% MS (ESI−) m/z: 791.3 [M−H]$^-$ calc. for $C_{33}H_{38}N_4O_{15}P_2^-$: 791.2.

Boc-GH(Trt)PGGPQ(Trt)G-OSu (P1)

Protected peptide Boc-GH(Trt)PGGPQ(Trt)G-OH (8.33 mg, 6.46 µmol) was treated with 0.25 M triethylamine solution in anhydrous DMF (78 µl, 16.2 µmol) then 0.25 M TSTU solution in anhydrous DMF (28.3 µl, 7.1 µmol). Mass spec. taken at 25 min showed succinimidyl ester as major peak. Solvent was removed in vacuum and residue was used immediately in the following step without purification. MS (ESI+) m/z: 1387.7 [M+H]$^+$ calc. for $C_{76}H_{83}N_{12}O_{14}^+$: 1387.6.

(4a)

Compound 3a (3.23 µmol) was transferred to a 1 ml vial by washing with water and evaporation in vacuum. 33 µl of water was added to the vial and 3a dissolved with shaking. 8.3 µl of saturated NaHCO$_3$ followed by 33 µl of THF. Activated peptide P1 was dissolved in 66 µl of THF and added. The reaction was left overnight. Solvents were removed by evaporation and residue was treated with 400 µl of 95:2.5:2.5 TFA:H$_2$O:Triisopropylsilane (TIS) solution. After 1 h, the reaction was checked by mass spec. and the target mass was detected. Solvents were removed under vacuum. The residue was dissolved in 500 µl of 0.1M TEAB in 10% MeOH with addition of 30 µl of Et$_3$N. Compound was purified by reverse-phase HPLC (10×250 mm Phenomenix Luna Cis column) using 0.1M TEAB pH 7.5 buffers containing 10% and 70% methanol (A and B respectively). Gradient was as follows: 0-3 min, 100% A; 3-23 min, 0-100% B. Individual fractions were checked by mass spec., fractions containing product were combined and evaporated then coevaporated twice with water. Amount was determined by UV absorbance (PBS Buffer, pH 7.4, ε=73,000 at 493 nm assumed). Yield: 1.28 µmol, 40% from 3a. MS (ESI−) m/z: 1478.6 [M−H]$^-$, 738.9 [M−2H]$^{2-}$. Calculated for $C_{62}H_{77}N_{15}O_{24}P_2^-$: 1478.5, $C_{62}H_{76}N_{15}O_{24}P_2^{2-}$: 738.7.

(5a)

To compound 4a (1.07 µmol) in a 1 ml vial was added 20 µl of water and 4 µl of saturated NaHCO$_3$. 49.8 µl (2.14 µmol) of 0.042 M black hole quencher-1 succinimidyl ester (BHQ-1 SE, Biosearch Technologies) in 2:1 THF:DMF was added. Reaction was stirred overnight. Solvents were removed and 200 µl of 50 mM NH$_4$OAc buffer with 5% Acetonitrile was added. The target compound was isolated by HPLC (4.6×250 mm Phenomenix Luna Cis column) using 50 mM ammonium acetate buffers adjusted to pH 7.0-7.4 containing 5% and 70% acetonitrile (A and B respectively). Gradient was as follows: 0-3 min, 100% A; 3-13 min, 0-100% B. Target eluted with a retention time of 14.8 min. Product fractions were combined and evaporated. Amount was determined by UV absorbance (PBS Buffer, pH 7.4, ε=34,660 at 534 nm estimated by addition of BHQ-1 and carboxyfluorescein extinction coefficients). Yield 0.348 µmol, 33%. MS (ESI−) m/z: calculated for $C_{62}H_{78}N_{15}O_{24}P_2^-$: 1964.7, 1965.7, 1966.7, 1967.7 found: 1964.6, 1965.6, 1966.5, 1967.5 [M−H]$^-$ calculated for $C_{62}H_{77}N_{15}O_{24}P_2^{2-}$: 982.8, found 982.5 [M−2H]$^{2-}$ Synthesis Far Red Probe (Alendronate-Based)

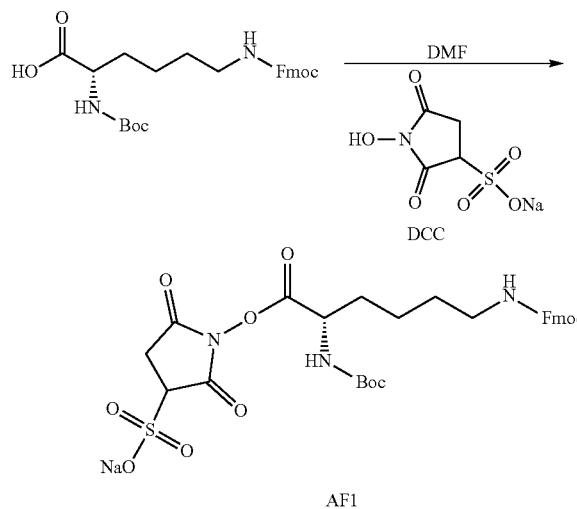

sodium 1-((N$_\epsilon$-(((9H-fluoren-9-yl)methoxy)carbonyl)-N$_\alpha$-(tert-butoxycarbonyl)-L-lysyl)oxy)-2,5-dioxopyrrolidine-3-sulfonate (AF1)

N$_\alpha$-Fmoc-NE-Boc-L-lysine (117.15 mg, 0.25 mmol) was dissolved in 625 µl of DMF and 1-Hydroxy-2,5-dioxopyrrolidine-3-sulfonic acid sodium salt (65.1 mg, 0.3) mmol was added and sonicated to form a fine suspension. DCC (51.55 mg, 0.25 mmol) was added and the mixture was stirred at room temperature for 50 min and centrifuged to remove solids. Reaction was checked by TLC in ethyl acetate (product RF=0) Solution of 1 was used without further purification.

AF1 solution in DMF (313 µl, 0.125 mmol) was added and the mixture stirred overnight at room temperature. The reaction mixture was diluted with 10 ml of 10:1 THF:Water and centrifuged. Supernatent was collected and solids were washed with 10:1 THF water (2×10 ml). Combined supernatant and washings were concentrated by evaporation to approximately 5 ml then diluted with 40 ml of water to give a cloudy suspension that was acidified by addition of 300 µl of acetic acid and extracted with ethyl acetate (3×20 ml). Aqueous phase was evaporated to dryness.

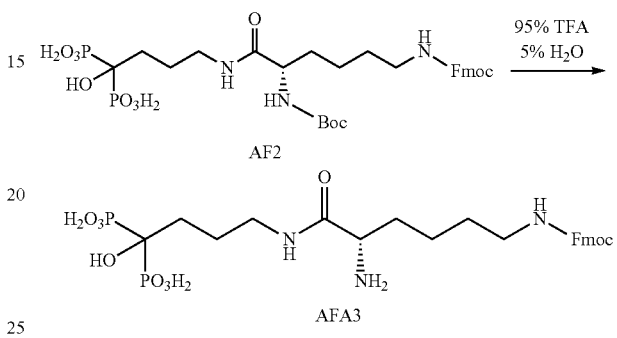

(S)-(4-(6-((((9H-fluoren-9-yl)methoxy)carbonyl)amino)-2-aminohexanamido)-1-hydroxybutane-1,1-diyl)bis(phosphonic acid) (AF3)

Half of the material from the previous step was dissolved in 95:5 TFA/Water and stirred for 1.5 h then evaporated to dryness in vacuo then coevaporated with water then 2:1 THF/water. The residue was then dissolved in 35% THF in water to make 10 ml of solution for quantification. A 5 µl

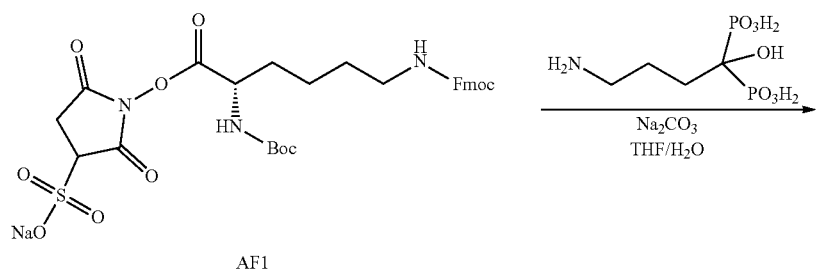

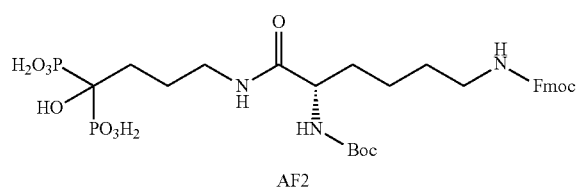

(S)-(4-(6-((((9H-fluoren-9-yl)methoxy)carbonyl)amino)-2-((tert-butoxycarbonyl)amino)hexanamido)-1-hydroxybutane-1,1-diyl)bis(phosphonic acid) (2)

Alendronate monosodium salt trihydrate (122 mg, 0.38 mmol) was suspended in water (1.25 ml) and pH adjusted to 7.8 with Na$_2$CO$_3$ giving a clear solution. Crude compound portion of the sample was spiked with 5 µl of 1 µM N$_\alpha$-Fmoc-N$_\epsilon$-Boc-L-lysine and analyzed by reverse phase HPLC (Shodex Asahipak ODP-50 4D column; buffer system: aqueous 50 mM triethylammonium bicarbonate, pH 9, A: 5% acetonitrile, B: 75% acetonitrile; gradient: 1 ml/min 0-3 min 0% B, 3-13 min 0 to 100% B). Yield 14.4 µmol, 23.1% from protected lysine.

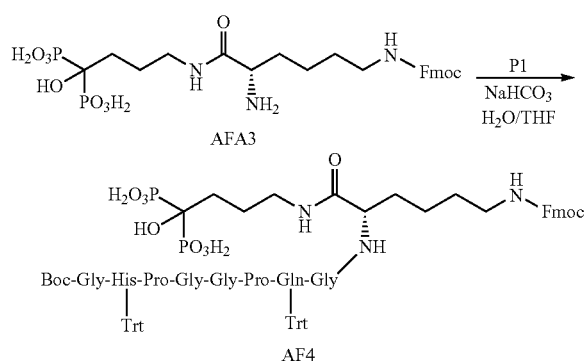

Compound AF4

Custom synthesized peptide Boc-GH(Trt)PGGPQ(Trt)G-OH (12.9 mg, 10 µmol) was dissolved in 0.25 M Triethylamine in DMF (100 µl) and 44 µl of freshly prepared 0.25 M N,N,N'N'-Tetramethyl-O—(N-succinimidyl)uronium tetrafluoroborate (TSTU) solution was added. After 20 min, succinimidyl activated peptide was detected by mass spectrometry (Positive mode, calculated: 1387.6 (M+H), 1409.6 (M+Na) found: M/Z=1387.8, 1409.6) solvents were removed in vacuum and dissolved in 25 µl of DMF. 3 (5 µmol) was dissolved in 50 µl of THF and 17 µl of saturated sodium bicarbonate. Activated peptide solution was added to the solution of 3 and precipitation was observed. 10 µl of water and 25 µl of THF were added, mostly dissolving the precipitate. After stirring overnight at room temperature, LCMS showed incomplete conversion of 3 to the product, so another portion of activated peptide was prepared as described above and dissolved in 25 µl of THF. The reaction mix was evaporated and dissolved in 25 µl of THF and 16.7 µl of water and the peptide solution was added. This time no precipitation was observed. After stirring 24 h at room temperature, only a trace of starting material 3 was detected. The target was isolated by HPLC (Shodex Asahipak ODP-50 4D column; buffer system: aqueous 50 mM triethylammonium bicarbonate, pH 9, A: 5% acetonitrile, B: 75% acetonitrile; gradient: 1 ml/min 0-3 min 0% B, 3-13 min 0 to 100% B).

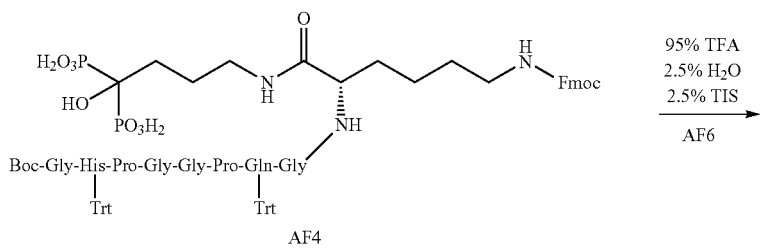

Compound AF5.

Entire quantity of AF4 was treated with 95% TFA, 2.5% water, 2.5% Triisopropylsilane for 1.5 h at room temperature before evaporation in vacuo and coevaporation with THF. Target was quantified by absorbance of the Fmoc protecting group at 300 nm. Yield: 0.917 µmol, 18.3% from 3.

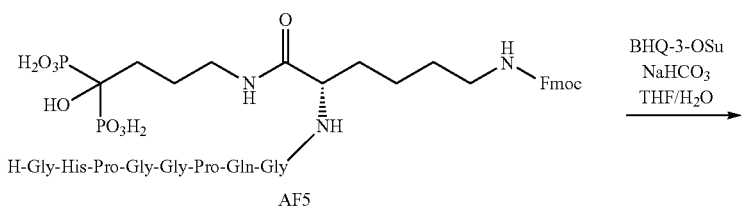

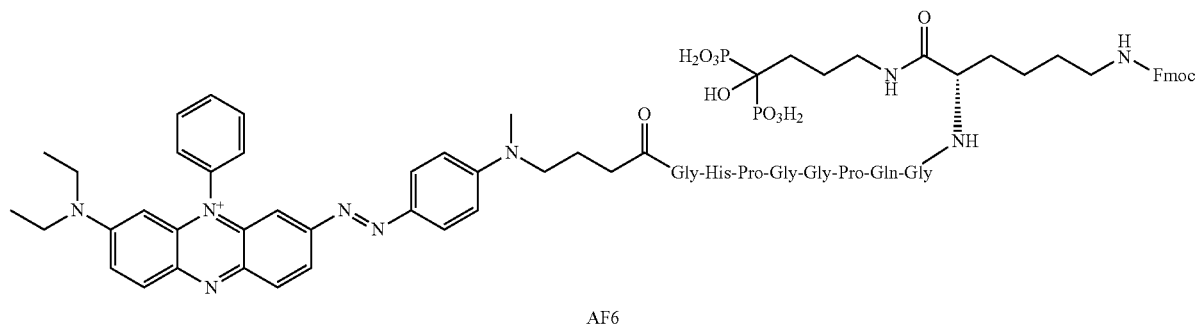

AF6

Compound AF6.

Compound AF5 (0.917 μmol) was dissolved in 50 μl of THF and 28 μl of water. 3.1 μl of saturated sodium bicarbonate was added. BHQ 3 succinimidyl ester (1.45 mg, 2.2 μmol) in 29 μl of DMF and the mixture was stirred overnight.

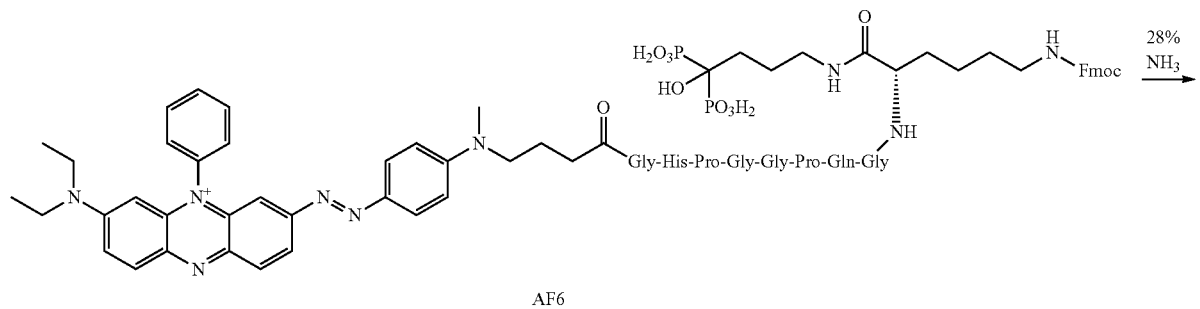

AF6

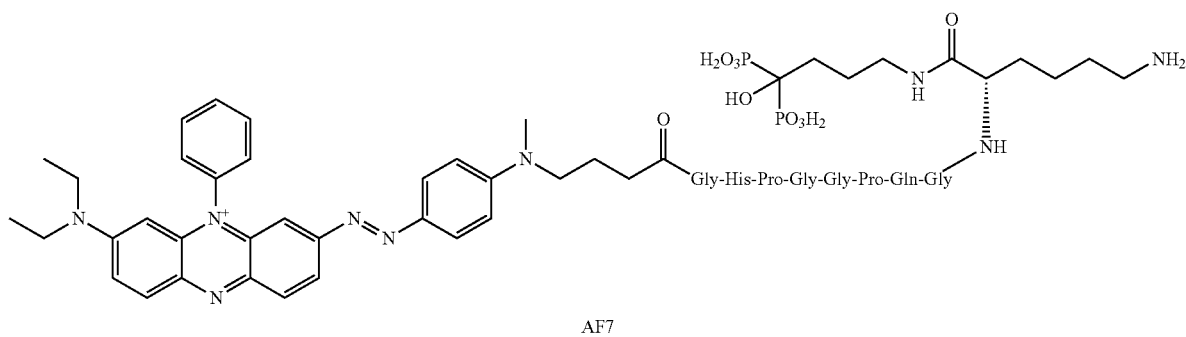

AF7

Compound AF7

Entire amount of compound 6 (<1.58 μMol) was treated with 500 μl of 28% aqueous ammonia and stirred at room temperature for 2 hours and evaporated in vacuum. Solid was dissolved in 200 μl of 1% aqueous TFA. The crude product was purified by HPLC (Shodex Asahipak ODP-50 4D column; Buffer system: aqueous 1% TFA, A: 5% acetonitrile, B: 75% acetonitrile; gradient: 1 ml/min. 0-1 min. 20% B, 1-17 min. 0 to 100% B). Yield: 513 nMol, 32.4% from compound 5.

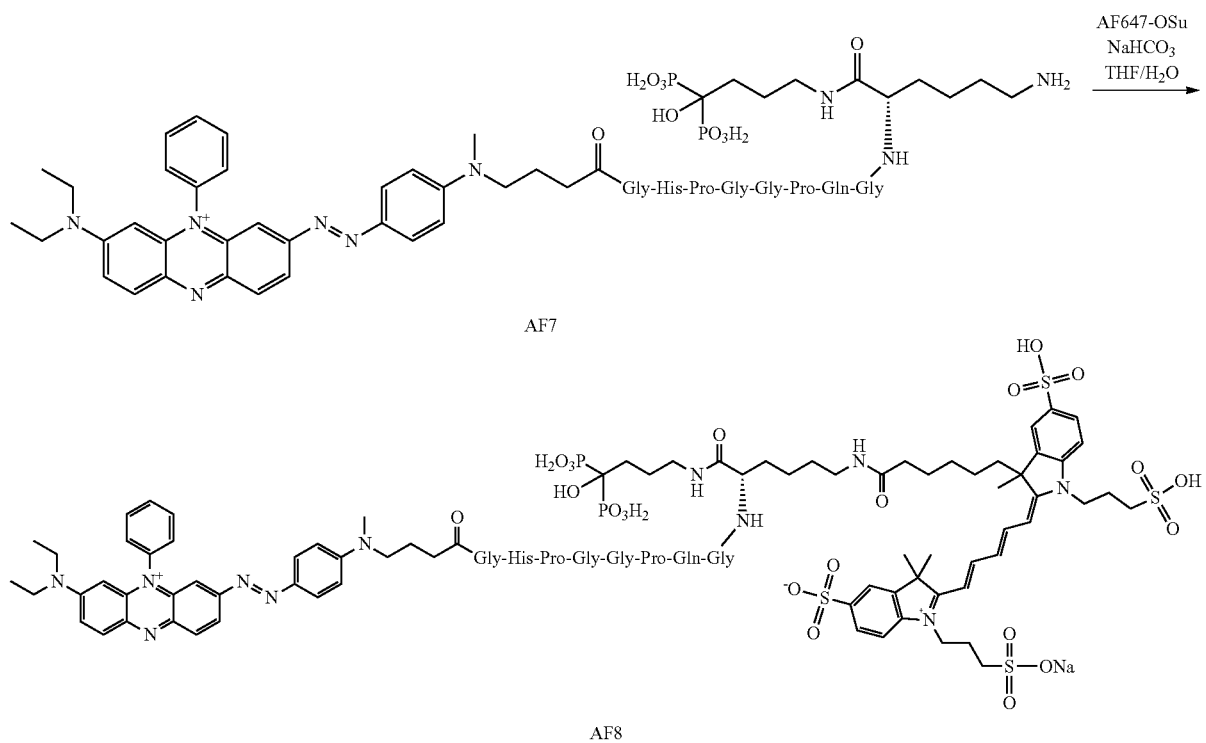

AF7

AF8

Compound AF8

AF647 carboxylic acid triethylamine salt (1.0 mg, 866 nMol) was dissolved in 31.2 µl of 0.25 M triethylamine in DMF and treated with 4.2 µl of 0.25 M N,N,N'N'-Tetramethyl-O—(N-succinimidyl)uronium tetrafluoroborate (TSTU) DMF solution. After 30 min, solvent was removed in vacuum. Compound 7 (433 nmol determined by absorbance at 260 nm, ε=13,000 for BHQ) was dissolved in 5.6 µl of 1% aqueous TFA followed by 30.4 µl of THF and 4 µl of saturated sodium bicarbonate. Black precipitate formed upon addition of sodium bicarbonate. Activated AF647 was dissolved in 40 µl of 2:1 THF/water and this solution was added to suspension of compound AF7. 20 µl of additional 2:1 THF/water was used to wash the remainder of AF 647 into the vial. After stirring overnight, supernatant was removed from the reaction mixture and the remaining solids washed with 200 µl of 70% acetonitrile with 1% TFA then 200 µl of water. 200 µl of water was added, then 1 µl of triethylamine. The solids dissolved completely to give a deep blue solution. Target was isolated by HPLC (Shodex Asahipak ODP-50 4D column; buffer system: aqueous 50 mM triethylammonium bicarbonate, pH 9, A: 5% acetonitrile, B: 75% acetonitrile; gradient: 1 ml/min. 0-3 min 0% B, 3-13 min 0 to 100% B). Retention time: 5.3 min.

Compound AF7 was dissolved in 25 µl of THF and 14 µl of water. 1.6 µl of saturated NaHCO₃ was added followed by 2 equivalents of AF 647 succinimidyl ester in DMF. Target was isolated by HPLC (Shodex Asahipak ODP-50 4D column; buffer system: aqueous 50 mM triethylammonium ticarbonate, pH 9, A: 5% tcetonitrile, B: 75% acetonitrile; gradient: 1 ml/min 0-3 min. 0% B, 3-13 min 0 to 100% B).

Reagent Sources:

Dicyclohexycarbodiimide, α-Fmoc-ε-Boc Lysine and 5(6) Carboxyfluorescein were purchased from Sigma Aldrich. N-hydroxysulfosuccinimide sodium salt was purchased from Chem Impex. Anhydrous N,N-dimethylformamide and tetrahydrofuran was purchased from EMD Millipore and used without further drying. Ethyl Acetate was purchased from VWR. Pamidronic Acid was provided courtesy of Novartis. Sodium Carbonate and Sodium Bicarbonate were purchased from Fisher Scientific. Custom synthesized peptide, Boc-GH(trt)PGGPQ(trt)G (SEQ ID NO:30), was purchased from CHI Scientific.

Enzyme Studies

Kinetic parameters $K_{cat}$ and $K_m$ were determined from initial rates at 37° C. and pH 5.5 in a buffer consisting of 50 mM sodium acetate buffer with 2.5 mM EDTA, 1 mM DTT and 0.01% TRITON X-100®. Enzyme concentration was 2.5 nM, substrate concentration ranged from 0.0781 to 2.50 µM. Fluorescence measurements were done every 1 min using a Biotek Synergy H₄ plate reader with black Corning 3720 96-well plates. Parameters were determined using a Lineweaver-Burke plot. Fluorescence calibration was obtained using compound 9a at concentrations between 0.00977 and 2.5 µM. Background fluorescence was estimated using intact 10a at concentrations ranging from 0.0781 to 2.50 µM.

Cathepsin K was prepared by activation of procathepsin K purchased from Enzo Life Sciences. Activation was carried out by adding 32.5 µM, pH 3.5 sodium acetate buffer in a 1:2 ratio to as-received proenzyme solution and leaving at 21° C. for 30 min before dilution with assay buffer. Solutions of activated enzyme were stored on ice and used within 10 min. Buffers were prepared in house according to concentrations provided by Enzo Life Sciences.

Results

Synthesis

USC FRET was synthesized in ten steps from α-Fmoc-ε-Boc Lysine, using a purchased custom synthesized peptide, carboxyfluorescein, and Black Hole Quencher-1 (BHQ-1). All amide bond couplings were carried out in water/organic solvent mixtures to ensure solubility of bisphosphonate compounds. The overall yield from α-Fmoc-ε-Boc Lysine was 2.9%. The synthesis makes use of succinimidyl esters of the fluorophore and quencher and the route would be compatible with many pairs of commercially available chromophores to cover a range of emission wavelengths into the near infrared (Johansson (2006) *Meth. Mol. Biol.* 335: 17-29; Peng et al. (2009) *Anal. Biochem.* 388:220-228).

Enzyme Studies $K_{cat}$ and $K_m$ values for cleavage of USC FRET in solution at 37° C. and pH 5.5 were found to be $K_{cat}$=0.2±0.03 s$^{-1}$ and $K_m$=1.7±0.2 μM respectively. $K_{cat}$ is lower and $K_m$ is higher than values found in literature for the substrate Abz-HPGGPQ-EDN2Ph, (0.5±0.03 s$^{-1}$ and 1.2±0.2) (Lecaille et al. (2003) *Biochem. J* 375:307-312) indicating that OFS-1 is cleaved by cathepsin K albeit at a slower rate than reported for Abz-HPGGPQ-EDN2Ph.

Discussion

Figure 3:
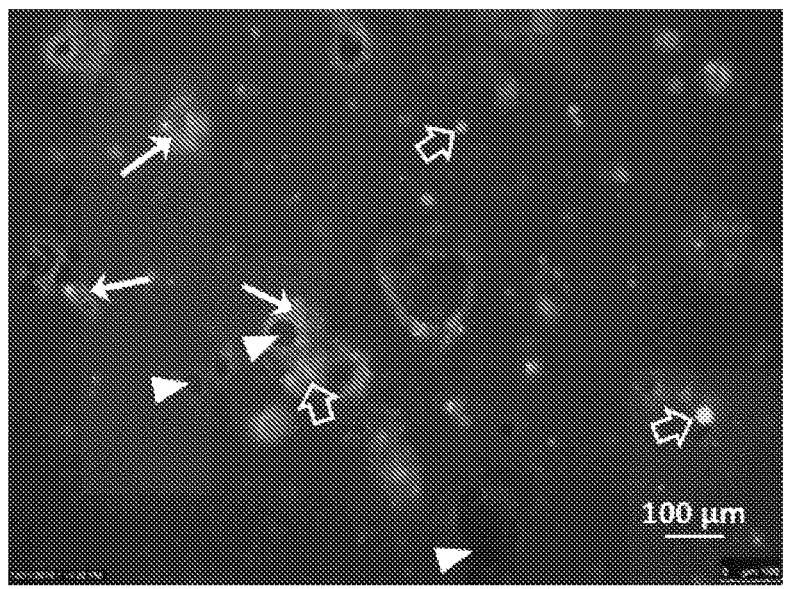
FIG. 3 shows HA coated plate preadsorbed with OFS-1. 7 h after seeding of osteoclasts. Indicated bright areas (solid arrows) correspond to regions of resorptive activity with remaining $Ca_3(PO_4)_2$. Dark holes (white triangles) are areas where $Ca_3(PO_4)_2$ layer has been dissolved away. Hollow arrows indicate fluorescent cells presumed to have uptaken OFS-1 and or its cleavage product.
Figure 4:
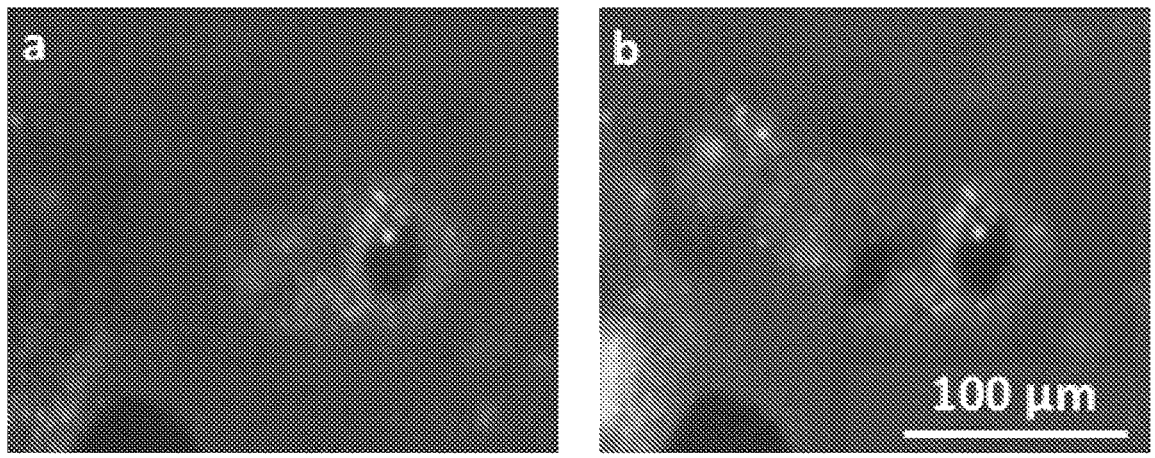
FIG. 4, panels a-b, shows still images extracted from time lapses video. Panel a) After osteoclast seeding initial resorption pit, cell, and surrounding probe activation are visible. Panel b) 7 h after first image. Osteoclast has migrated to the left end of the frame leaving a trail of activated probe and a new pit behind.
Figure 5:
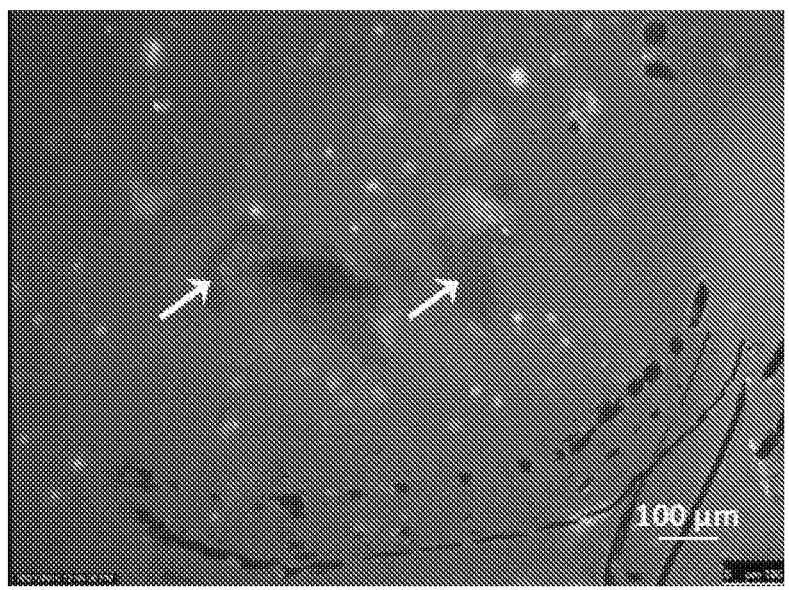
FIG. 5 shows that after osteoclast seeding, dark areas indicated are due to carboxyfluorescein pH sensitivity to acidic environment within the osteoclast sealing zone and can be seen moving rapidly in the time lapse videos.
Figure 6:
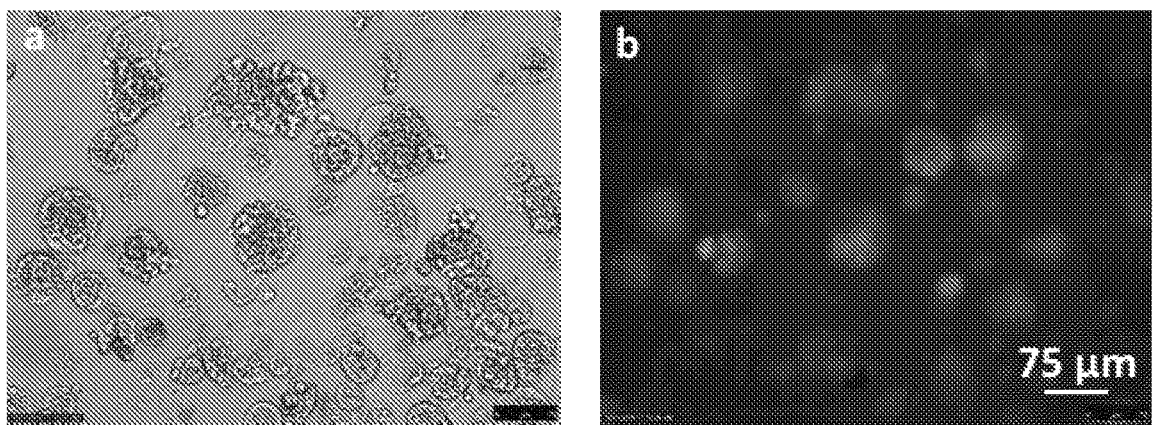
FIG. 6. Panel a) White light bright field image of floating cells from OFS-1 coated microwells. Panel b) Fluorescence microscope image of same cells.

Timelapse videos obtained after seeding osteoclast cells onto calcium phosphate coated microwells (Corning Osteoassay plates) preadsorbed with USC FRET-1 showed increased fluorescence around cells that were actively resorbing hydroxyapatite (HA), but little fluorescence was observed in areas where the calcium phosphate layer had been dissolved away completely (see, e.g., FIG. 3). We attribute this to a lack of calcium phosphate for the probe to bind to. In several cases, osteoclasts can be seen migrating on the surface without completely dissolving the calcium phosphate and leaving a trail of enhanced fluorescence in their wake (see, e.g., FIG. 4). This is how the probe is presumed to function in vivo, by fluorescently labeling any regions exposed to osteoclast resorptive activity. The areas of the substrate unaffected by osteoclast activity exhibit weak, even fluorescence as a result of incomplete quenching in the intact probe. Another phenomenon observed in all videos was a transient decrease in fluorescence within the boundaries of the osteoclast sealing zone, seen as rapidly moving dark areas around the cells (see, e.g., FIG. 5). This effect was expected and results from the pH sensitivity of carboxyfluorescein. The pH under an active osteoclast has been reported to be as low as 4.5 (Teitelbaum (2000) *Science,* 289(5484): 1504-1508). Carboxyfluorescein cyclizes to a nonfluorescent form when protonated and has a pKa of approximately 6.5 (Han & Burgess (2010) *Chem. Rev.* 110: 2709-2728; Massou et al. (2000) *Biochem. Educ.* 28:171-173). Thus fluorescent intensity is decreased. This is further evidence that the probe is exposed to the sub-osteoclast environment as intended. Another phenomenon observed in the timelapses was concentrated fluorescent intensity in cells themselves, both attached and detached from the substrate. Fluorescent, free-floating cells can be seen in the videos as well as in still images of the supernatant taken from the microwells (FIG. 6). This is evidence that the probe is being uptaken by the osteoclasts as has been seen with other fluorescently-labeled bisphosphonates in vitro and in vivo (Thompson et al. (2006) *Mol. Pharmacol.* 69: 1624-1632; Kashemirov et al. (2008) *Bioconjug. Chem.* 19: 2308-2310; Tseng et al. (2015) *Oncotarget* 6: 20002-20025; Coxon et al. (2008) *Bone* 42: 848-860; Vermeer et al. (2013) *Bone,* 57: 242-251; Roelofs et al. (2010) *J Bone Miner. Res.* 25: 606-616).

This probe could be used in vitro as a way of determining whether osteoclasts are secreting cathepsin k and can be used to track their migration on mineral substrates, even when the mineral layer is not fully resorbed. Since it can easily be applied to calcium mineral substrates at room temperature, OFS-1 is more convenient and physiologically relevant than the traditional approach to measuring osteoclast migration on glass with gold nanoparticles (Owens & Chambers (1993) *Biochem. Biophys. Res.* 195: 1401-1407).

With the successful development of OFS-1, we have designed and are preparing a far-red version of the probe employing the same peptide sequence and linker with ALEXA FLUOR® 647 (AF647) as the fluorophore and Black Hole Quencher-3 (BHQ-3) as the quencher.

Additionally, we this strategy can be extended for use in drug delivery targeting areas of bone resorption. Employing protease-cleavable linkers between a bisphosphonate and a drug, specific, local delivery to sites of osteolysis can be achievable. An example of this approach is targeting antimicrobial agents to sites of osteomyelitis by using a substrate of cathepsin K to respond to the increased osteoclast activity around the infected site or a specific substrate of a bacterial protease or a protease expressed in human immune cells. Another compelling possibility is the targeting of anti-cancer drugs to sites of bone metastasis using a linker cleaved by cathepsin K or other enzymes. Drugs that retain their activity despite functionalization with a short peptide fragment left over after cleavage would be preferred. Macromolecular drugs such as biologics would be expected to tolerate this since they are large relative to the linker. In various embodiments small molecule drugs are believed to work as well. A linker that cleaves completely from the drug such as self-immolative linker can also be used to release an intact parent drug.

CONCLUSION

A new fluorescent "sentinel" probe, OFS-1, for studying osteoclast behavior and cathepsin K activity on the surface of bone has been developed and demonstrated in vitro and in vivo. It has been shown to be activated by purified cathepsin K, by human monocyte-derived osteoclasts, and in vivo in mice. The mineral affinity of OFS-1 allows it to accumulate on a calcium phosphate surface and leave a lasting fluorescent signal in response to osteoclast activity. In vivo experiments show that the probe shows enhanced signal in response to tooth extraction, which is known to locally increase osteoclast activity.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. An osteoasorptive fluorogenic probe, said probe comprising a compound according to Formula I:

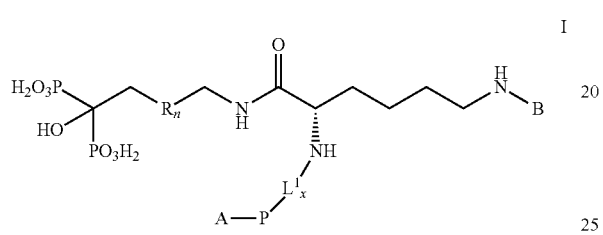

wherein:

R is CH$_2$;

n is 0 to 6;

L$^1$ is a linker comprising 1 to 6 carbons;

x is 0 or 1;

P is a peptide comprising a cleavage site for a protease; and

A is a quencher and B is a fluorophore, or B is a quencher and A is a fluorophore; and A is attached directly to P or A is attached to P through a linker.

2. The probe of claim 1, wherein said probe comprises a compound according to Formula II:

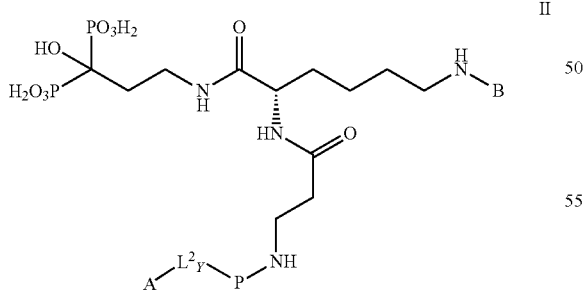

wherein:

L$^2$ is selected from the group consisting of a C1-C12 carbon linker, an amino acid, and a peptide; and y is 0 or 1.

3. The probe of claim 1, wherein said probe comprises a compound according to Formula III:

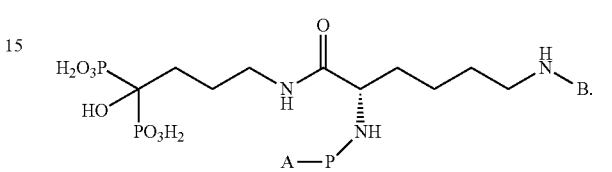

4. The probe of claim 1, wherein A is a quencher and B is a fluorophore.

5. The probe of claim 1, wherein P ranges in length from about 6 amino acid up to about 10 amino acids.

6. The probe of claim 1, wherein P comprises a cleavage site for a protease selected from the group consisting of cathepsin K, cathepsin B, cathepsin C, cathepsin D, cathepsin E, cathepsin G, cathepsin L, tartrate-resistant acid protease (TRAP), matrix metalloproteinases (MMP)-2, MMP-8, MMP-9, MMP-10, MMP-12, MMP-13, MMP-14, Kallikreins (hK), hK1, PSA (hK3), hK10, hK15, seriene proteases uPA and uPAR, plasmin, ceruloplasmin (CP), thrombin, trypsin, fibroblast activation protein (FAP), and caspases.

7. The probe of claim 1, wherein P comprises the amino acid sequence Gly-His-Pro-Gly-Gly-Pro-Gln-Gly (SEQ ID NO:1).

8. The probe of claim 1, wherein:

said fluorophore is a fluorophore that emits in the visible spectrum or in the near infrared; and/or said fluorophore is selected from the group consisting of FAM, BODIPY FL, Oregon Green 488, Rhodamine Green, Oregon Green 514, TET, Cal Gold, BODIPY R6G, Yakima Yellow, JOE, HEX, Cal Orange, BODIPY TMR-X, Quasar-570/Cy3, TAMRA, Rhodamine Red-X, Redmond Red, BODIPY 581/591, Cy3.5, ROX, Cal Red/Texas Red, BODIPY TR-X, BODIPY 630/665-X, Pulsar-650, Quasar-670/Cy5, Cy5.5, ALEXAFLUOR® AF647, ALEXAFLUOR® AF660, ALEXAFLUOR® AF680, ALEXAFLUOR® AF700, ALEXAFLUOR® AF750, ALEXAFLUOR® AF790.

9. The probe of claim 1, wherein said fluorophore comprises 5-FAM or ALEXAFLUOR® AF647.

10. The probe of claim 1, wherein:

said quencher is selected from the group consisting of BHQ-1, BHQ-3, Dabcyl, QSY 35, BHQ-0, Eclipse, QSY 7, QSY 9, BHQ-2, ElleQuencher, Iowa Black, QSY 21, TAMRA, and Blackberry Quencher BBQ-650; or said quencher comprises BHQ-1; or said quencher comprises BHQ-3.

11. The probe of claim 1, wherein:

said probe comprises a fluorophore/quencher pair shown (by an X) in Table 4; or said fluorophore comprises 5-FAM and said quencher comprises BHQ-1; or
said fluorophore comprises ALEXAFLUOR® AF647 and said quencher comprises BHQ-3; or
said fluorophore comprises 5-FAM and said quencher comprises BHQ-1.

12. The probe of claim 1, wherein said probe comprises the structure:

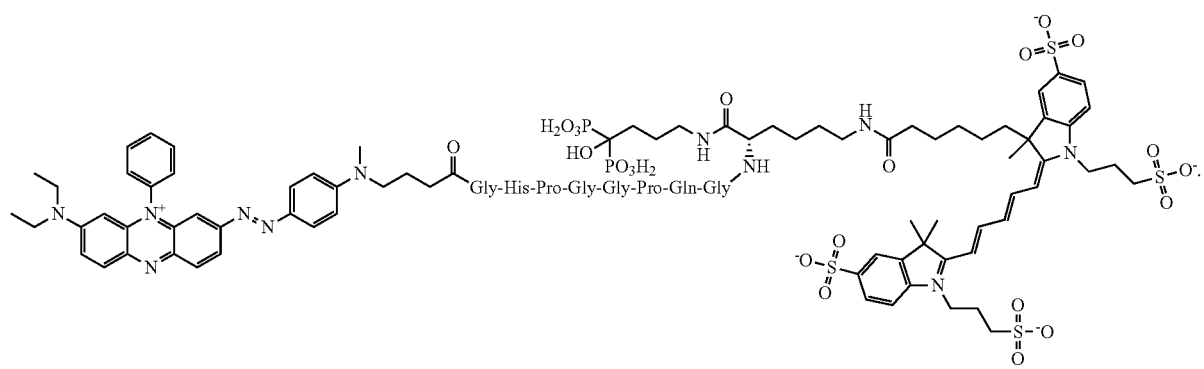

13. The probe of claim 1, wherein:
said probe accumulates on a calcium phosphate surface when administered to a mammal in vivo;
said probe said probe provides a detectable signal in vivo when said peptide is cleaved by a protease; and
said probe, when administered to a mammal in vivo, is taken up by bone.

14. A pharmaceutical formulation said formulation comprising:
a probe of claim 1; and
a pharmaceutically acceptable carrier.

15. A method of detecting protease activity in vivo in a mammal, said method comprising:
administering or causing to be administered to said mammal a probe of claim 1, where the peptide in said probe comprises a cleavage site for said protease; and
detecting a signal from the fluorophore comprising said probe where said signal indicates that said protease has cleaved said peptide and provides an indication of the activity and/or location of said protease.

16. An osteoabsorptive drug delivery vehicle, said vehicle comprising a compound according to Formula IV:

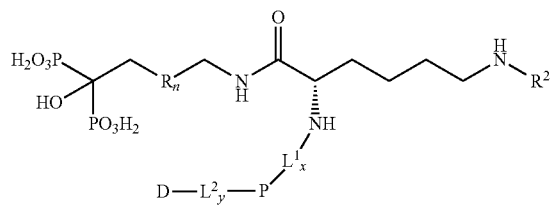

wherein:
R is $CH_2$;
n, x, and y are independently 0 or 1;
$L^1$ is a linker comprising 1 to 6 carbons;
$R^2$ is H or a protecting group;
$L^2$ is a linker, wherein said linker is a C1-C12 carbon linker, an amino acid, or a peptide;
P is a peptide comprising a cleavage site for a protease; and
D is a therapeutic moiety wherein said therapeutic moiety is a peptide or small organic molecule.

17. The vehicle of claim 16, wherein said vehicle comprises a compound according to Formula V:

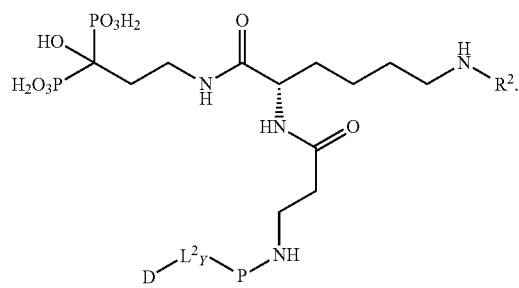

18. The vehicle of claim 16, wherein said vehicle comprises a compound according to Formula VI:

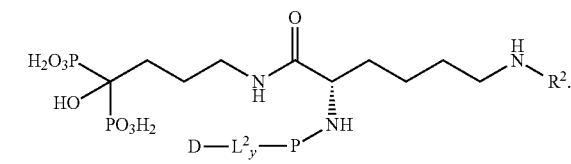

19. The vehicle of claim 16, wherein:
D comprises a small organic molecule; or
D comprises an antibiotic; or
D comprises an antibiotic shown in Table 6; or
D comprises an anti-cancer agent; or
D comprises an anti-cancer agent selected from the group consisting of flourouracil (5-FU), capecitabine, 5-trifluoromethyl-2'-deoxyuridine, methotrexate sodium, raltitrexed, pemetrexed, cytosine Arabinoside, 6-mercaptopurine, azathioprine, 6-thioguanine (6-TG), pentostatin, fludarabine phosphate, cladribine, floxuridine (5-fluoro-2), ribonucleotide reductase inhibitor (RNR), cyclophosphamide, neosar, ifosfamide, thiotepa, 1,3- bis(2-chloroethyl)-1-nitosourea (BCNU), 1,-(2-chloroethyl)-3-cyclohexyl-lnitrosourea, methyl (CCNU), hexamethylmelamine, busulfan, procarbazine HCL, dacarbazine (DTIC), chlorambucil, melphalan, cisplatin, carboplatin, oxaliplatin, bendamustine, carmustine, chloromethine, dacarbazine (DTIC), fotemustine, lomustine, mannosulfan, nedaplatin, nimustine, prednimustine, ranimustine, satraplatin, semustine, streptozocin, temozolomide, treosulfan, triaziquone, triethylene melamine, thioTEPA, triplatin tetranitrate, trofosfamide, uramustine, doxorubicin, daunorubicin citrate, mitoxantrone, actinomycin D, etoposide, topotecan HCL, teniposide (VM-26), irinotecan HCL (CPT-11), camptothecin, belotecan, rubitecan, vincristine, vinblastine sulfate, vinorelbine tartrate, vindesine sulphate, paclitaxel, docetaxel, nanoparticle paclitaxel, abraxane, ixabepilone, larotaxel, ortataxel, tesetaxel, vinflunine, retinoic acid, a retinoic acid derivative, doxirubicin, vinblastine, vincristine, cyclophosphamide, ifosfamide, cisplatin, 5-fluorouracil, a camptothecin derivative, interferon, tamoxifen, and taxol.

20. A pharmaceutical formulation said formulation comprising:
a vehicle of claim 16; and
a pharmaceutically acceptable carrier.

21. A method of treating a pathology characterized by bone resorption in a mammal, said method comprising:
administering or causing to be administered to said mammal, an effective amount of a drug delivery vehicle of claim 16, wherein D is selected from the group consisting of parathyroid hormone, a parathyroid hormone analog, calcitonin, a drug that induces bone growth, and an anti-cancer drug.

* * * * *

SEQUENCE LISTING

<160> NUMBER OF SEQ ID NOS: 30

<210> SEQ ID NO 1
<211> LENGTH: 8

```
<212> TYPE: PRT
<213> ORGANISM: Artificial
<220> FEATURE:
<223> OTHER INFORMATION: Protease substrate

<400> SEQUENCE: 1

Gly His Pro Gly Gly Pro Gln Gly
1               5

<210> SEQ ID NO 2
<211> LENGTH: 6
<212> TYPE: PRT
<213> ORGANISM: Artificial
<220> FEATURE:
<223> OTHER INFORMATION: Protease substrate
<220> FEATURE:
<221> NAME/KEY: misc_feature
<222> LOCATION: (6)..(6)
<223> OTHER INFORMATION: Xaa is N alpha, N
      epsilon-Bis(2,4-dinitrophenyl)-L-lysine

<400> SEQUENCE: 2

Gly Ile Val Arg Ala Xaa
1               5

<210> SEQ ID NO 3
<211> LENGTH: 5
<212> TYPE: PRT
<213> ORGANISM: Artificial
<220> FEATURE:
<223> OTHER INFORMATION: Protease substrate

<400> SEQUENCE: 3

Arg Gly Phe Phe Pro
1               5

<210> SEQ ID NO 4
<211> LENGTH: 11
<212> TYPE: PRT
<213> ORGANISM: Artificial
<220> FEATURE:
<223> OTHER INFORMATION: Protease substrate
<220> FEATURE:
<221> NAME/KEY: misc_feature
<222> LOCATION: (10)..(10)
<223> OTHER INFORMATION: N alpha, N
      epsilon-Bis(2,4-dinitrophenyl)-L-lysine
<220> FEATURE:
<221> NAME/KEY: misc_feature
<222> LOCATION: (11)..(11)
<223> OTHER INFORMATION: Xaa is D-arginine

<400> SEQUENCE: 4

Gly Lys Pro Ile Leu Phe Phe Arg Leu Xaa Xaa
1               5                   10

<210> SEQ ID NO 5
<211> LENGTH: 9
<212> TYPE: PRT
<213> ORGANISM: Artificial
<220> FEATURE:
<223> OTHER INFORMATION: Protease substrate
<220> FEATURE:
<221> NAME/KEY: misc_feature
<222> LOCATION: (8)..(8)
<223> OTHER INFORMATION: Xaa is N alpha, N
      epsilon-Bis(2,4-dinitrophenyl)-L-lysine
<220> FEATURE:
<221> NAME/KEY: misc_feature
<222> LOCATION: (9)..(9)
<223> OTHER INFORMATION: Xaa is D-arginine
```

-continued

```
<400> SEQUENCE: 5

Gly Ser Pro Ala Phe Leu Ala Xaa Xaa
1               5

<210> SEQ ID NO 6
<211> LENGTH: 4
<212> TYPE: PRT
<213> ORGANISM: Artificial
<220> FEATURE:
<223> OTHER INFORMATION: Protease substrate

<400> SEQUENCE: 6

Ala Ala Pro Phe
1

<210> SEQ ID NO 7
<211> LENGTH: 4
<212> TYPE: PRT
<213> ORGANISM: Artificial
<220> FEATURE:
<223> OTHER INFORMATION: Protease substrate

<400> SEQUENCE: 7

Ala Ala Pro Met
1

<210> SEQ ID NO 8
<211> LENGTH: 9
<212> TYPE: PRT
<213> ORGANISM: Artificial
<220> FEATURE:
<223> OTHER INFORMATION: Protease substrate
<220> FEATURE:
<221> NAME/KEY: misc_feature
<222> LOCATION: (1)..(3)
<223> OTHER INFORMATION: Xaa is any amino acid
<220> FEATURE:
<221> NAME/KEY: misc_feature
<222> LOCATION: (4)..(4)
<223> OTHER INFORMATION: Xaa is Ala, Val, Leu, Ile, Phe, Trp, or Tyr
<220> FEATURE:
<221> NAME/KEY: misc_feature
<222> LOCATION: (7)..(9)
<223> OTHER INFORMATION: Xaa is any amino acid

<400> SEQUENCE: 8

Xaa Xaa Xaa Xaa Phe Arg Xaa Xaa Xaa
1               5

<210> SEQ ID NO 9
<211> LENGTH: 9
<212> TYPE: PRT
<213> ORGANISM: Artificial
<220> FEATURE:
<223> OTHER INFORMATION: Protease substrate
<220> FEATURE:
<221> NAME/KEY: misc_feature
<222> LOCATION: (1)..(3)
<223> OTHER INFORMATION: Xaa is any amino acid
<220> FEATURE:
<221> NAME/KEY: misc_feature
<222> LOCATION: (4)..(4)
<223> OTHER INFORMATION: Xaa is Phe, Trp, His, or Tyr
<220> FEATURE:
<221> NAME/KEY: misc_feature
<222> LOCATION: (7)..(9)
<223> OTHER INFORMATION: Xaa is any amino acid

<400> SEQUENCE: 9
```

Xaa Xaa Xaa Xaa Phe Arg Xaa Xaa Xaa
1               5

<210> SEQ ID NO 10
<211> LENGTH: 9
<212> TYPE: PRT
<213> ORGANISM: Artificial
<220> FEATURE:
<223> OTHER INFORMATION: Protease substrate
<220> FEATURE:
<221> NAME/KEY: misc_feature
<222> LOCATION: (1)..(3)
<223> OTHER INFORMATION: Xaa is any amino acid
<220> FEATURE:
<221> NAME/KEY: misc_feature
<222> LOCATION: (4)..(4)
<223> OTHER INFORMATION: Xaa is Ala, Val, Leu, Ile, Phe, Trp, or Tyr
<220> FEATURE:
<221> NAME/KEY: misc_feature
<222> LOCATION: (7)..(9)
<223> OTHER INFORMATION: Xaa is any amino acid

<400> SEQUENCE: 10

Xaa Xaa Xaa Xaa Arg Arg Xaa Xaa Xaa
1               5

<210> SEQ ID NO 11
<211> LENGTH: 9
<212> TYPE: PRT
<213> ORGANISM: Artificial
<220> FEATURE:
<223> OTHER INFORMATION: Protease substrate
<220> FEATURE:
<221> NAME/KEY: misc_feature
<222> LOCATION: (1)..(3)
<223> OTHER INFORMATION: Xaa is any amino acid
<220> FEATURE:
<221> NAME/KEY: misc_feature
<222> LOCATION: (4)..(4)
<223> OTHER INFORMATION: Xaa is Phe, Trp, His, or Tyr
<220> FEATURE:
<221> NAME/KEY: misc_feature
<222> LOCATION: (7)..(9)
<223> OTHER INFORMATION: Xaa is any amino acid

<400> SEQUENCE: 11

Xaa Xaa Xaa Xaa Arg Arg Xaa Xaa Xaa
1               5

<210> SEQ ID NO 12
<211> LENGTH: 4
<212> TYPE: PRT
<213> ORGANISM: Artificial
<220> FEATURE:
<223> OTHER INFORMATION: Protease substrate
<220> FEATURE:
<221> NAME/KEY: misc_feature
<222> LOCATION: (2)..(4)
<223> OTHER INFORMATION: Xaa is any amino acid

<400> SEQUENCE: 12

His Xaa Xaa Xaa
1

<210> SEQ ID NO 13
<211> LENGTH: 8
<212> TYPE: PRT
<213> ORGANISM: Artificial
<220> FEATURE:
<223> OTHER INFORMATION: Protease substrate

<400> SEQUENCE: 13

```
Gly Pro Leu Gly Ile Ala Gly Gln
1               5

<210> SEQ ID NO 14
<211> LENGTH: 5
<212> TYPE: PRT
<213> ORGANISM: Artificial
<220> FEATURE:
<223> OTHER INFORMATION: Protease substrate
<220> FEATURE:
<221> NAME/KEY: misc_feature
<222> LOCATION: (2)..(3)
<223> OTHER INFORMATION: Xaa is any amino acid
<220> FEATURE:
<221> NAME/KEY: misc_feature
<222> LOCATION: (4)..(4)
<223> OTHER INFORMATION: Xaa is Ala, Val, Leu, Ile, Phe, Trp, or Tyr
<220> FEATURE:
<221> NAME/KEY: misc_feature
<222> LOCATION: (5)..(5)
<223> OTHER INFORMATION: Xaa is Ser or Thr

<400> SEQUENCE: 14

Pro Xaa Xaa Xaa Xaa
1               5

<210> SEQ ID NO 15
<211> LENGTH: 4
<212> TYPE: PRT
<213> ORGANISM: Artificial
<220> FEATURE:
<223> OTHER INFORMATION: Protease substrate

<400> SEQUENCE: 15

Pro Leu Gly Leu
1

<210> SEQ ID NO 16
<211> LENGTH: 4
<212> TYPE: PRT
<213> ORGANISM: Artificial
<220> FEATURE:
<223> OTHER INFORMATION: Protease substrate

<400> SEQUENCE: 16

Pro Ala Asn Leu
1

<210> SEQ ID NO 17
<211> LENGTH: 4
<212> TYPE: PRT
<213> ORGANISM: Artificial
<220> FEATURE:
<223> OTHER INFORMATION: Peptide linker

<400> SEQUENCE: 17

Gly Gly Gly Gly
1

<210> SEQ ID NO 18
<211> LENGTH: 5
<212> TYPE: PRT
<213> ORGANISM: Artificial
<220> FEATURE:
<223> OTHER INFORMATION: Peptide linker

<400> SEQUENCE: 18

Pro Ser Pro Ser Pro
```

```
1               5

<210> SEQ ID NO 19
<211> LENGTH: 5
<212> TYPE: PRT
<213> ORGANISM: Artificial
<220> FEATURE:
<223> OTHER INFORMATION: Peptide linker

<400> SEQUENCE: 19

Pro Ser Pro Ser Pro
1               5

<210> SEQ ID NO 20
<211> LENGTH: 4
<212> TYPE: PRT
<213> ORGANISM: Artificial
<220> FEATURE:
<223> OTHER INFORMATION: Peptide linker

<400> SEQUENCE: 20

Lys Lys Lys Lys
1

<210> SEQ ID NO 21
<211> LENGTH: 4
<212> TYPE: PRT
<213> ORGANISM: Artificial
<220> FEATURE:
<223> OTHER INFORMATION: Peptide linker

<400> SEQUENCE: 21

Arg Arg Arg Arg
1

<210> SEQ ID NO 22
<211> LENGTH: 5
<212> TYPE: PRT
<213> ORGANISM: Artificial
<220> FEATURE:
<223> OTHER INFORMATION: Peptide linker

<400> SEQUENCE: 22

Ala Ser Ala Ser Ala
1               5

<210> SEQ ID NO 23
<211> LENGTH: 6
<212> TYPE: PRT
<213> ORGANISM: Artificial
<220> FEATURE:
<223> OTHER INFORMATION: Peptide linker

<400> SEQUENCE: 23

Gly Gly Ser Gly Gly Ser
1               5

<210> SEQ ID NO 24
<211> LENGTH: 5
<212> TYPE: PRT
<213> ORGANISM: Artificial
<220> FEATURE:
<223> OTHER INFORMATION: Peptide linker

<400> SEQUENCE: 24

Gly Gly Gly Gly Ser
1               5
```

```
<210> SEQ ID NO 25
<211> LENGTH: 10
<212> TYPE: PRT
<213> ORGANISM: Artificial
<220> FEATURE:
<223> OTHER INFORMATION: Peptide linker

<400> SEQUENCE: 25

Gly Gly Gly Gly Ser Gly Gly Gly Gly Ser
1               5                   10

<210> SEQ ID NO 26
<211> LENGTH: 15
<212> TYPE: PRT
<213> ORGANISM: Artificial
<220> FEATURE:
<223> OTHER INFORMATION: Peptide linker

<400> SEQUENCE: 26

Gly Gly Gly Gly Ser Gly Gly Gly Gly Ser Gly Gly Gly Gly Ser
1               5                   10                  15

<210> SEQ ID NO 27
<211> LENGTH: 20
<212> TYPE: PRT
<213> ORGANISM: Artificial
<220> FEATURE:
<223> OTHER INFORMATION: Peptide linker

<400> SEQUENCE: 27

Gly Gly Gly Gly Ser Gly Gly Gly Gly Ser Gly Gly Gly Gly Ser Gly
1               5                   10                  15

Gly Gly Gly Ser
            20

<210> SEQ ID NO 28
<211> LENGTH: 25
<212> TYPE: PRT
<213> ORGANISM: Artificial
<220> FEATURE:
<223> OTHER INFORMATION: Peptide linker

<400> SEQUENCE: 28

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 29
<211> LENGTH: 30
<212> TYPE: PRT
<213> ORGANISM: Artificial
<220> FEATURE:
<223> OTHER INFORMATION: Peptide linker

<400> SEQUENCE: 29

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 30
<211> LENGTH: 8
<212> TYPE: PRT
```

```
<213> ORGANISM: Artificial
<220> FEATURE:
<223> OTHER INFORMATION: Synthetic peptide

<400> SEQUENCE: 30

Gly His Pro Gly Gly Pro Gln Gly
1               5
```